United States Patent
Makriyannis et al.

(10) Patent No.: US 8,853,205 B2
(45) Date of Patent: *Oct. 7, 2014

(54) HETEROPYRROLE ANALOGS ACTING ON CANNABINOID RECEPTORS

(75) Inventors: Alexandros Makriyannis, Watertown, MA (US); Venkata Kiran Vemuri, Boston, MA (US)

(73) Assignee: University of Connecticut, Farmington, CT (US)

( * ) Notice: Subject to any disclaimer, the term of this patent is extended or adjusted under 35 U.S.C. 154(b) by 460 days.

This patent is subject to a terminal disclaimer.

(21) Appl. No.: 13/202,499

(22) PCT Filed: Feb. 19, 2009

(86) PCT No.: PCT/US2009/001054
§ 371 (c)(1),
(2), (4) Date: Nov. 11, 2011

(87) PCT Pub. No.: WO2010/104488
PCT Pub. Date: Sep. 16, 2010

(65) Prior Publication Data
US 2012/0046280 A1    Feb. 23, 2012

Related U.S. Application Data

(63) Continuation-in-part of application No. 11/813,546, filed as application No. PCT/US2006/000720 on Jan. 10, 2006, now Pat. No. 8,084,451.

(60) Provisional application No. 60/642,544, filed on Jan. 10, 2005.

(51) Int. Cl.
C07D 231/14 (2006.01)
C07D 233/90 (2006.01)
C07D 409/04 (2006.01)
C07D 405/12 (2006.01)
C07D 401/10 (2006.01)

(52) U.S. Cl.
CPC ............ C07D 231/14 (2013.01); C07D 401/10 (2013.01); C07D 409/04 (2013.01); C07D 405/12 (2013.01); C07D 233/90 (2013.01)
USPC .................. 514/227.8; 514/235.8; 514/236.5; 514/318; 514/326; 514/406; 544/139; 544/140; 544/406; 546/187; 546/211; 548/365.7

(58) Field of Classification Search
None
See application file for complete search history.

(56) References Cited

U.S. PATENT DOCUMENTS

| | | | |
|---|---|---|---|
| 4,256,727 A | 3/1981 | Triplett et al. | |
| 4,732,900 A | 3/1988 | Weber et al. | |
| 5,155,124 A | 10/1992 | Kimata et al. | |
| 5,208,231 A | 5/1993 | Kimata et al. | |
| 5,462,960 A * | 10/1995 | Barth et al. ................. 514/406 |
| 6,432,984 B1 | 8/2002 | Barth et al. | |
| 6,509,367 B1 | 1/2003 | Martin et al. | |
| 7,119,108 B1 | 10/2006 | Makriyannis et al. | |
| 7,393,842 B2 | 7/2008 | Makriyannis et al. | |
| 7,745,440 B2 | 6/2010 | Makriyannis et al. | |
| 7,872,006 B2 | 1/2011 | Moritani et al. | |
| 8,084,451 B2 * | 12/2011 | Makriyannis et al. ........ 514/241 |
| 2004/0192667 A1 | 9/2004 | Makriyannis et al. | |
| 2004/0248956 A1 | 12/2004 | Hagmann et al. | |

FOREIGN PATENT DOCUMENTS

| | | |
|---|---|---|
| EP | 0576357 A1 | 12/1993 |
| EP | 0656354 A1 | 6/1995 |
| EP | 0658546 A1 | 6/1995 |
| FR | 2758723 A1 | 7/1998 |
| FR | 2856683 A1 | 12/2004 |
| WO | 9719063 A1 | 5/1997 |
| WO | 9721682 A1 | 6/1997 |
| WO | 2005000820 | 1/2005 |
| WO | 2006067443 | 6/2006 |
| WO | 2006074445 A2 | 7/2006 |
| WO | 2007061948 A2 | 5/2007 |

OTHER PUBLICATIONS

Fan, H. et al., "Analogs of JHU75528, a PET ligand for imaging of cerebral cannabinoid receptors (CB1): Development of ligands with optimized lipophilicity and binding affinity." European Journal of Medicinal Chemistry, 44, pp. 593-609, 2009.
European Search Report dated Jun. 28, 2012.
Notification of Transmittal, the International Search Report and Written Opinion of the International Searching Authority for PCT/US2009/001054 dated Sep. 14, 2009.
International Preliminary Report on Patentability for PCT/US2009/001054 dated Aug. 23, 2011.
Howlett A.C. et al. "Azido- and isothiocyanato-substituted aryl pyrazoles bind covalently to the CB1 cannabinoid receptor and impair signal transduction", Journal of Neurochemistry, Wiley Interscience, New York, NY, US, vol. 74, No. 5, Jan. 1, 2000, 2174-2181.

(Continued)

Primary Examiner — Kamal Saeed
(74) Attorney, Agent, or Firm — Alix, Yale & Ristas, LLP

(57) ABSTRACT

Disclosed are biologically active hetero pyrrole analogs such as imidazoles, thiazoles, oxazoles and pyrazoles capable of interacting with the CB1 and/or CB2 cannabinoid receptors. Aspects disclose hetero pyrrole analogs acting as CB1 and/or CB 1 receptor antagonists, having selectivity for the CB 1 or CB2 receptor, acting as neutral antagonists, acting preferentially on CB 1 receptors located in the peripheral nervous system, and/or acting as nitric oxide donors. Pharmaceutical preparations employing the disclosed analogs and methods of administering therapeutically effective amounts of the disclosed analogs to provide a physiological effect are also disclosed.

20 Claims, 2 Drawing Sheets

(56) References Cited

OTHER PUBLICATIONS

Lange J.H.M. et al. "Bioisosteric replacements of the pyrazole moiety of rimonabant: synthesis, biological properties, and molecular modeling investigations of thiazoles, triazoles, and imidazoles as potent and selective CB1 cannabinoid receptor antagonists", Journal of Medicinal Chemistry, American Chemical Society, US, vol. 48, Jan. 1, 2005, 1823-1838.

Jarbe T. U.; Lemay B. J.; Vemuri V. K.; Vadivel S. K.; Zvonok A.; Makriyannis A. Central mediation and differential blockade by cannabinergics of the discriminative stimulus effects of the cannabinoid CB(1) receptor antagonist rimonabant in rats. Psychopharmacology (Berl). 2011 DOI 10.1007/s00213-011-2226-3).

Cluny N. L.; Chambers A. P.; Vemuri V. K.; Wood J. T.; Eller L. K.; Freni C.; Reimer R. A.; Makriyannis A.; Sharkey K. A. The neutral cannabinoid CB receptor antagonist AM4113 regulates body weight through changes in energy intake in the rat. Pharmacol Biochem Behav. 2011, 97, (3), 537-43.

Randall P. A.; Vemuri V. K.; Segovia K. N.; Torres E. F.; Hosmer S.; Nunes E. J.; Santerre J. L.; Makriyannis A. Salamone J. D. The novel cannabinoid CB1 antagonist AM6545 suppresses food intake and food-reinforced behavior. Pharmacol Biochem Behav. 2010, 97, (1), 179-84.

Jarbe T. U.; LeMay B. J.; Olszewska T.; Vemuri V. K.; Wood J. T.; Makriyannis A. Intrinsic effects of AM4113, a putative neutral CB1 receptor selective antagonist, on open-field behaviors in rats. Pharmacol Biochem Behav. 2008, 91, (1), 84-90.

Hodge J.; Bow J. P.; Plyler K. S.; Vemuri V. K.; Wisniecki A.; Salamone J. D.; Makriyannis A.; McLaughlin P. J. The cannabinoid CB1 receptor inverse agonist AM 251 and antagonist AM 4113 produce similar effects on the behavioral satiety sequence in rats. Behav Brain Res. 2008, 193, (2), 298-305.

Bergman J.; Delatte M. S.; Paronis C. A.; Vemuri K.; Thakur G. A.; Makriyannis A. Some effects of CB1 antagonists with inverse agonist and neutral biochemical properties. Physiol Behav. 2008, 93, (4-5), 666-70.

Sink K. S.; Vemuri V. K.; Wood J.; Makriyannis A.; Salamone J. D. Oral bioavailability of the novel cannabinoid CB1 antagonist AM6527: effects on foodreinforced behavior and comparisons with AM4113. Pharmacol Biochem Behav. 2009, 91, (3), 303-6.

Cluny N. L.; Vemuri V. K.; Chambers A. P.; Limebeer C. L.; Bedard H.; Wood J. T.; Lutz B.; Zimmer A.; Parker L. A.; Makriyannis A.; Sharkey K. A. A novel peripherally restricted cannabinoid receptor antagonist, AM6545, reduces food intake and body weight, but does not cause malaise, in rodents. Br J Pharmacol. 2010, 161, (3), 629-42.

Limebeer C. L.; Vemuri V. K.; Bedard H.; Lang S. T.; Ossenkopp K. P.; Makriyannis A.; Parker L. A. Inverse agonism of cannabinoid CB1 receptors potentiates LiCl-induced nausea in the conditioned gaping model in rats. Br J Pharmacol. 2010, 161, (2), 336-49.

Tam J.; Vemuri V. K.; Liu J.; Batkai S.; Mukhopadhyay B.; Godlewski G.; Osei-Hyiaman D.; Ohnuma S.; Ambudkar S. V.; Pickel J.; Makriyannis A.; Kunos G. Peripheral CB1 cannabinoid receptor blockade improves cardiometabolic risk in mouse models of obesity. J Clin Invest. 2010, 120, (8), 2953-66.

Sink K. S.; Segovia K. N.; Collins L. E; Markus E. J.; Vemuri V. K.; Makriyannis A.; Salamone J. D. The CB1 inverse agonist AM251, but not the CB1 antagonist AM4113, enhances retention of contextual fear conditioning in rats. Pharmacol Biochem Behav. 2010, 95, (4), 479-84.

Sink K. S.; Segovia K. N.; Sink J.; Randall P. A.; Collins L. E.; Correa M.; Markus E. J.; Vemuri V. K.; Makriyannis A.; Salamone J. D. Potential anxiogenic effects of cannabinoid CB1 receptor antagonists/inverse agonists in rats: comparisons between AM4113, AM251, and the benzodiazepine inverse agonist FG-7142. Eur Neuropsychopharmacol. 2010, 20, (2), 112-22.

Storr M. A.; Bashashati M.; Hirota C.; Vemuri V. K.; Keenan C. M.; Duncan M.; Lutz B.; Mackie K.; Makriyannis A.; Macnaughton W. K.; Sharkey K. A. Differential effects of CB(1) neutral antagonists and inverse agonists on gastrointestinal motility in mice. Neurogastroenterol Motil. 2010, 22, (7), 787-96, e223.

Chambers A. P.; Vemuri V. K.; Peng Y.; Wood J. T.; Olszewska T.; Pittman Q. J.; Makriyannis A.; Sharkey K. A.; A neutral CB1 receptor antagonist reduces weight gain in rat. Am J Physiol Regul Integr Comp Physiol. 2007, 293, (6), R2185-93.

Sink K. S.; McLaughlin P. J.; Wood J. A.; Brown C.; Fan P.; Vemuri V. K.; Peng Y.; Olszewska T.; Thakur G. A.; Makriyannis A.; Parker L. A.; Salamone J. D. The novel cannabinoid CB1 receptor neutral antagonist AM4113 suppresses food intake and food-reinforced behavior but does not induce signs of nausea in rats. Neuropsychopharmacology. 2008, 33, (4), 946-55.

\* cited by examiner

HETEROPYRROLE ANALOGS ACTING ON CANNABINOID RECEPTORS

CROSS REFERENCE TO RELATED APPLICATIONS

The present application is a continuation-in-part of U.S. patent application Ser. No. 11/813,546, filed Sep. 16, 2008, which claims the benefit of PCT/US2006/000720, filed Jan. 10, 2006, which claims the benefit of U.S. Provisional Application No. 60/642,544, filed Jan. 10, 2005, and claims the benefit of PCT/US2009/001054, filed Feb. 19, 2009, the contents of each of which are incorporated herein by reference in their entirety.

STATEMENT REGARDING FEDERALLY SPONSORED RESEARCH OR DEVELOPMENT

This invention was made with Government support under Grant No. DA7215 awarded by the National Institute on Drug Abuse. The Government may have certain rights in the invention.

FIELD OF THE INVENTION

The present invention relates generally to biologically active hetero pyrrole analogs such as imidazoles, thiazoles, oxazoles and pyrazoles capable of interacting with the CB1 and/or the CB2 cannabinoid receptors, including neutral antagonists, inverse-agonists and partial agonists. Another aspect of the invention is concerned with such compounds having a range of useful applications including use of certain neutral antagonists, inverse-agonists and partial agonists to treat medical conditions with no or substantially reduced incidence of side-effects. Other aspects of the invention are concerned with new and improved hetero pyrrole analogs acting as neutral antagonists, inverse-agonists and partial agonists selective for the CB1 and/or the CB2 receptors and use of these new and improved hetero pyrrole analogs as peripherally acting or centrally acting compounds. Also, aspects of the invention are concerned with all isotopic variations of these compounds, combination therapy and pharmaceutical preparations and compositions employing the inventive analogs and methods of administering therapeutically effective amounts of the inventive analogs to provide a physiological effect.

BACKGROUND OF THE INVENTION

Marijuana (*Cannabis sativa*) and derivatives have been used for medicinal and recreational purposes. The major active constituent extracted from *Cannabis sativa* is the classical cannabinoid $\Delta^9$-Tetrahydrocannabinol ($\Delta^9$-THC). The effects of such cannabinoids are due to an interaction with specific high-affinity receptors. Presently, two cannabinoid receptors have been characterized: CB1, a central receptor found in the mammalian brain and a number of other sites in peripheral tissues; and CB2, a peripheral receptor found principally in cells related to the immune system. The CB1 receptor is believed to mediate the psychoactive properties associated with classical cannabinoids. Characterization of these receptors has been made possible by the development of specific synthetic ligands such as the agonists WIN 55212-2 and CP 55,940.

In addition to acting at the cannabinoid receptors, cannabinoids such as $\Delta^9$-THC also affect cellular membranes, thereby producing undesirable side effects such as drowsiness, impairment of monoamine oxidase function and impairment of non-receptor mediated brain function. The addictive and psychotropic properties of some cannabinoids also limit their therapeutic value.

International Publication number WO 03/007887 A2 to Finke et al describes imidazole derivatives alleged to have binding affinity for the central cannabinoid receptor. International Publication number WO 03/027076 A2 to Kruse et al also describes some imidazole derivatives alleged to have binding affinity for cannabinoid receptors.

SUMMARY OF THE INVENTION

Figure 1B:
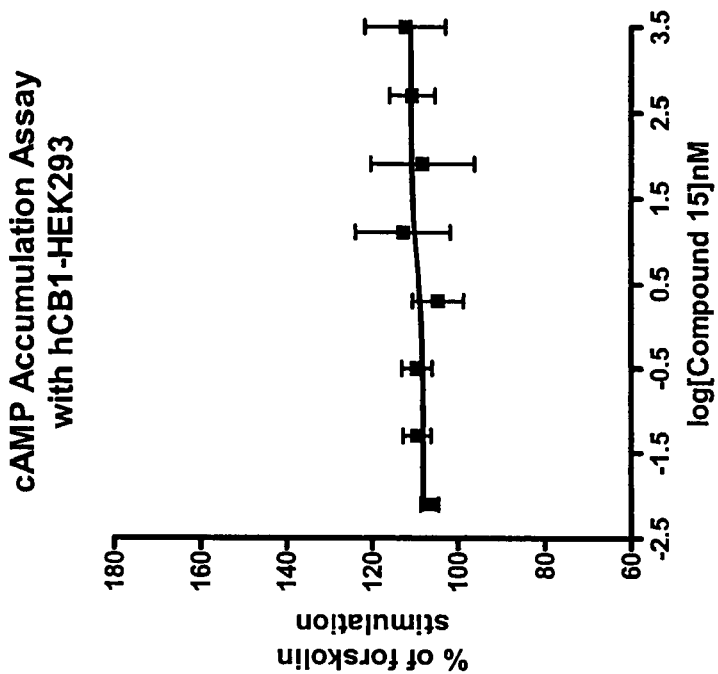
FIGS. 1A-1B are graphs showing cAMP accumulation with hCB1-HEK292 cells (Compound 2 and 15)

Briefly stated, one embodiment of the invention is concerned with new and improved cannabimimetic (cannabinoid like) imidazole analogs. The inventive cannabimimetic imidazole ligands of this embodiment can be represented by general formula I and their enantiomers, diastereomers, geometric isomers, racemates, tautomers, rotamers, atropisomers, metabolites, in vivo hydrolysable esters, N-oxides, salts, solvates, hydrates, polymorphic forms (crystalline or amorphous) or pro-drugs:

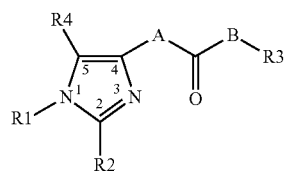

A comprises a direct bond, O, or —(CH$_2$)$_l$N(R5)
B comprises a direct bond, O, N(R5), —(CH$_2$)$_l$— or —NH—SO$_2$—R5 is hydrogen, OH, alkyl or substituted alkyl and
l is an integer from 0 to 3.
In a variation of formula I, R1 and R2 each independently comprise —(CH$_2$)$_n$—Z.
n is an integer from 0 to about 7.
Z comprises H, halogen, CF$_3$, CF$_2$H, N$_3$, NCS, CN, NO$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, O-aroyl, O(CH$_2$)$_j$OX$_3$, O(CH$_2$)$_j$NX$_1$X$_2$, alkyl-CN, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO2-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, aryl, NO$_2$, NO, (CH$_2$)$_m$CN, hydroxyloweralkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$ wherein $X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or $-CX_9=CHX_{10}$ wherein $X_9$ and $X_{10}$ each independently comprise H or alkyl Wherein m is an integer from 0 to 7 j is an integer from 0 to about 6, or k is an integer from 0 to about 2

In a variation of formula I, R1 and R2 each independently comprise $-(CH_2)_n-Z$.

n is an integer from 0 to about 7.

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the $-(CH_2)_n-$ group and the Z group can be any available ring carbon atom or any available ring nitrogen atom.

In a variation of formula I, R1 and R2 each independently comprise $-(CH_2)_n-Z$.

n is an integer from 0 to about 7.

Z comprises a 5 member unsaturated ring having 0 to 4 independently selected heteroatoms as ring members, a substituted 5 member unsaturated ring having 0 to 4 independently selected heteroatoms as ring members, a 6 member aromatic ring having 0 to 5 independently selected heteroatoms as ring members or a substituted 6 member aromatic ring having 0 to 5 independently selected heteroatoms; and wherein the connecting point between the $-(CH_2)_n-$ group and the Z group can be any available ring carbon atom or any available ring nitrogen atom.

In a variation of formula I, R1 and R2 each independently comprise $-(CH_2)_n-Z$.

n is an integer from 0 to about 7.

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the $-(CH_2)_n-$ group and the Z group can be any available ring carbon atom or any available ring nitrogen atom.

In a variation of formula I, R1 and R2 each independently comprise $-(CH_2)_n-Z$.

n is an integer from 0 to about 7.

Z comprises

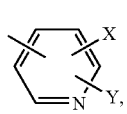 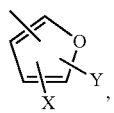 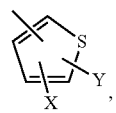

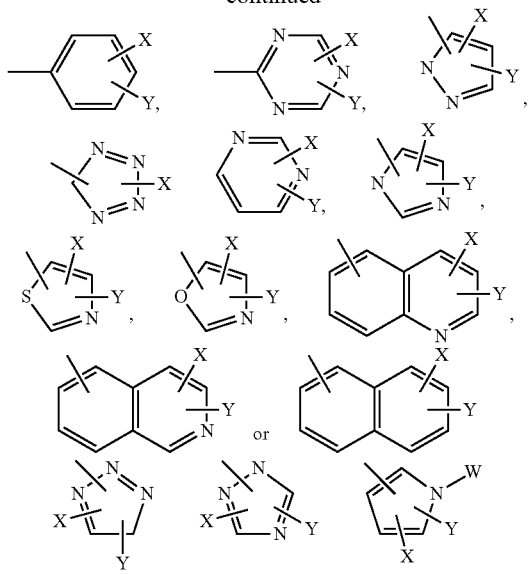

wherein X and Y each independently comprise, H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, alkyl-CN, O-aroyl, $O(CH_2)_jOX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, $-CH=CHX_8$, $-C\equiv CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, aryl, $NO_2$, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$ wherein $X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or $-CX_9=CHX_{10}$ wherein $X_9$ and $X_{10}$ each independently comprise H or alkyl Wherein m is an integer from 0 to 7 j is an integer from 0 to about 6, or

W comprises H or alkyl k is an integer from 0 to about 2

In a variation of formula I, R1 and R2 each independently $-(CH_2)_n-Z$.

n is an integer from 0 to about 7.

Z comprises a carbocyclic ring having 6 ring atoms fused to a heterocyclic ring having from 5 to 7 ring atoms, a carbocyclic ring having 6 ring atoms fused to a heteroaromatic ring having from 5 to 7 ring atoms, a heterocyclic ring having 6 ring atoms fused to a heterocyclic ring having from 5 to 7 ring atoms, an heterocyclic ring having 6 ring atoms fused to a heteroaromatic ring having from 5 to 7 ring atoms, an aromatic ring having 6 ring atoms fused to a heterocyclic ring having from 5 to 7 ring atoms, an aromatic ring having 6 ring atoms fused to a heteroaromatic ring having from 5 to 7 ring atoms, a heteroaromatic ring having 6 ring atoms fused to a heterocyclic ring having from 5 to 7 ring atoms or a heteroaromatic ring having 6 ring atoms fused to a heteroaromatic ring having from 5 to 7 ring atoms.

In a variation of formula I, R1 and R2 each independently comprise —$(CH_2)_n$—Z;

n comprises an integer from 0 to about 7;

Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 3 independently selected heteroatoms as ring members or an unsaturated ring having 6 ring atoms and 0 to 4 independently selected heteroatoms as ring members fused to an unsaturated ring having 6 or 7 ring atoms and 0 to 4 independently selected heteroatoms as ring members.

In a variation of formula I, R1 and R2 each independently comprise —$(CH_2)_m$-$Q_1$-$(CH_2)_n$—Z;

$Q_1$ comprises NH, O, S, —CH=CH—, —C≡C—, —CO, $SO_2$ or $OSO_2$;

m is an integer from 1 to about 7;

n is an integer from 0 to about 7;

Z comprises H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, O-aroyl, $O(CH_2)_jOX_3$, $O(CH_2)_jNX_1X_2$, alkyl-CN, NH-acyl, NH-aroyl, CHO, $C(halogen)_3$, $COOX_3$, $SO_3H$, $SO_2NX_1X_2$, $CONX_1X_2$, NHC(O)O-alkyl, NHSO2-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members;

$X_3$ comprises H, alkyl, $NO_2$, NO, $(CH_2)_mCN$, hydroxyloweralkyl, or alkyl-$NX_1X_2$;

$X_4$, $X_5$, and $X_6$ each independently comprise H, alkyl, carbocyclic ring, hydroxyloweralkyl, alkyl-OH, halogen, CN, SNO, $S(SO_2)alkyl$, $NX_1X_2$, $COOX_3$, $CONX_3$, $OX_7$, or O-alkyl-$X_7$, wherein $X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$, wherein $X_9$ and $X_{10}$ each independently comprise H or alkyl;

m is an integer from 0 to 7;

j is an integer from 0 to about 6, and k is an integer from 0 to about 2.

In a variation of formula I, R1 and R2 each independently comprise -$Q_2$-$(CH_2)_n$—Z;

$Q_2$ is optionally present and if present comprises —$CH_2$—NH, —$CH_2$—O, —$CH_2$—S, —$CH_2$—$SO_2$ or —$CH_2$—$OSO_2$;

n is an integer from 0 to about 7;

Z comprises H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, O-aroyl, $O(CH_2)_jOX_3$, $O(CH_2)_jNX_1X_2$, alkyl-CN, NH-acyl, NH-aroyl, CHO, $C(halogen)_3$, $COOX_3$, $SO_3H$, $SO_2NX_1X_2$, $CONX_1X_2$, NHC(O)O-alkyl, NHSO2-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, NO, $(CH_2)_mCN$, hydroxyloweralkyl, or alkyl-$NX_1X_2$;

$X_4$, $X_5$, and $X_6$ each independently comprise H, alkyl, carbocyclic ring, hydroxyloweralkyl, alkyl-OH, halogen, CN, SNO, $S(SO_2)alkyl$, $NX_1X_2$, $COOX_3$, $CONX_3$, $OX_7$, or O-alkyl-$X_7$, wherein $X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$, wherein $X_9$ and $X_{10}$ each independently comprise H or alkyl;

m is an integer from 0 to 7;

j is an integer from 0 to about 6; and k is an integer from 0 to about 2.

In a variation of formula I, R1 and R2 each independently comprise —$(CH_2)_m$-$Q_1$-$(CH_2)_n$—Z;

$Q_1$ comprises NH, O, S, CH=CH, C≡C, CO, $SO_2$ or $OSO_2$;

m is an integer from 1 to about 7;

n is an integer from 0 to about 7; and

Z comprises a bicyclic ring, a heterobicyclic ring, a tricyclic ring, a heterotricyclic ring, a polycyclic ring or a heteropolycyclic ring.

In a variation of formula I, R1 and R2 each independently comprise —$(CH_2)_m$-$Q_1$-$(CH_2)_n$—Z;

$Q_1$ comprises NH, O, S, CH=CH, C≡C, CO, $SO_2$ or $OSO_2$;

m is an integer from 1 to about 7;

n is an integer from 0 to about 7;

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members; a bicyclic ring, a heterobicyclic ring, a tricyclic ring, a heterotricyclic ring, a polycyclic ring, a heteropolycyclic ring or any above group substituted on at least one available ring atom by an alkyl group or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of formula I, R1 and R2 each independently comprise —$(CH_2)_m$-$Q_1$-$(CH_2)_n$—Z;

$Q_1$ comprises N, O, S, CH=CH, C≡C, CO, $SO_2$ or $OSO_2$;

m is an integer from 1 to about 7;

n is an integer from 0 to about 7; and

Z comprises a 5 member unsaturated ring having 0 to 4 independently selected heteroatoms as ring members, a substituted 5 member unsaturated ring having 0 to 4 independently selected heteroatoms as ring members, a 6 member aromatic ring having 0 to 5 independently selected heteroatoms as ring members or a substituted 6 member aromatic ring having 0 to 5 independently selected heteroatoms; and wherein the connecting point between the $-(CH_2)_n-$ group and the Z group can be any available ring carbon atom or any available ring nitrogen atom.

In a variation of formula I R1 and R2 each independently comprise $-(CH_2)_m-Q_1-(CH_2)_n-Z$;

$Q_1$ comprises NH, O, S, CH=CH, C≡C, CO, SO$_2$ or OSO$_2$;

m is an integer from 1 to about 7;

n is an integer from 0 to about 7; and

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the $-(CH_2)_n-$ group and the Z group can be any available ring carbon atom or any available ring nitrogen atom.

In a variation of formula I R1 and R2 each independently comprise $-(CH_2)_m-Q_1-(CH_2)_n-Z$;

$Q_1$ comprises N, O, S, CH=CH, C≡C, CO, SO$_2$ or OSO$_2$;

m is an integer from 1 to about 7;

n is an integer from 0 to about 7;

Z comprises wherein X and Y each independently comprise, H, halogen, CF$_3$, CF$_2$H, N$_3$, NCS, CN, NO$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO2-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, NO$_2$, (CH$_2$)$_m$CN, hydroxyloweralkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$, wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein X$_8$ comprises H, alkyl, carbocyclic ring, heterocyclic ring, aromatic ring, heteroaromatic ring, or —CX$_9$=CHX$_{10}$, wherein X$_9$ and X$_{10}$ each independently comprise H or alkyl;

m is an integer from 0 to 7;

j is an integer from 0 to about 6;

k is an integer from 0 to about 2; and

W comprises H or alkyl

In a variation of formula I R1 and R2 each independently comprise. $-(CH_2)_m-Q_1-(CH_2)_n-Z$;

$Q_1$ comprises NH, O, S, CH=CH, C≡C, CO, SO$_2$ or OSO$_2$;

m is an integer from 1 to about 7;

n is an integer from 0 to about 7; and

Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 4 independently selected heteroatoms as ring members fused to an unsaturated ring having 6 or 7 ring atoms and 0 to 4 independently selected heteroatoms as ring members.

In a variation of formula I R1 and R2 each independently comprise $-(CH_2)_m-Q_1-(CH_2)_n-Z$;

$Q_1$ comprises NH, O, S, CH=CH, C≡C, CO, SO$_2$ or OSO$_2$;

m is an integer from 1 to about 7;

n is an integer from 0 to about 7; and

Z comprises

-continued

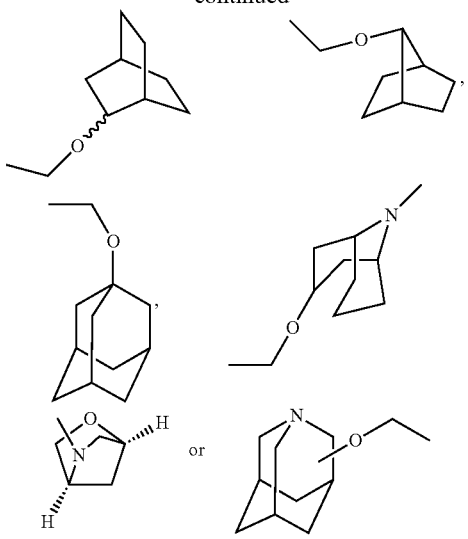

In a variation of formula I R1 and R2 each independently comprise -T-(CH$_2$)$_n$—Z;

n comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Z comprises H, halogen, CF$_3$, CF$_2$H, N$_3$, NCS, CN, NO$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, O-aroyl, O(CH$_2$)$_j$OX$_3$, O(CH$_2$)$_j$NX$_1$X$_2$, alkyl-CN, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO2-alkyl, alkoxy, alkyl, alcohol, alkylmercapto, alkylamino, di-alkylamino, alkylsulfinyl or alkylsulfonyl, CX$_4$X$_5$X$_6$, —CH═CHX$_8$, —C≡CX$_8$;

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, NO$_2$, NO, (CH$_2$)$_m$CN, hydroxyloweralkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$, wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein X$_8$ comprises H, alkyl, carbocyclic ring, heterocyclic ring, aromatic ring, heteroaromatic ring, or —CX$_9$═CHX$_{10}$, wherein X$_9$ and X$_{10}$ each independently comprise H or alkyl;

m is an integer from 0 to 7;

j is an integer from 0 to about 6; and k is an integer from 0 to about 2

In a variation of formula I R1 and R2 each independently comprise -T-(CH$_2$)$_n$—Z;

n comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring; and Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom.

In a variation of formula I R1 and R2 each independently comprise -T-(CH$_2$)$_n$—Z;

n comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring; and Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom.

In a variation of formula I R1 and R2 each independently comprise -T-(CH$_2$)$_n$—Z;

n comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Z comprises

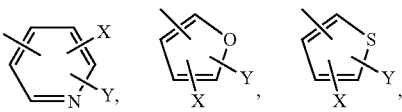

-continued

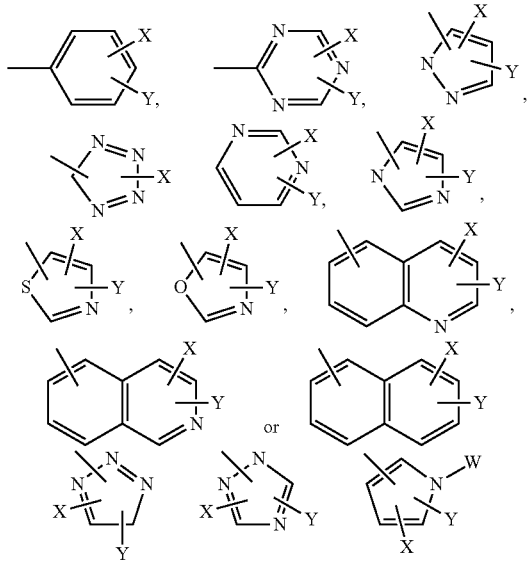

wherein X and Y each independently comprise, H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, alkyl-CN, O-aroyl, $O(CH_2)_jOX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, NHC(O)O-alkyl, NHSO2-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, $(CH_2)_mCN$, hydroxylower-alkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)alkyl$, $NX_1X_2$, $COOX_3$, $CONX_3$, $OX_7$, or O-alkyl-$X_7$ wherein $X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$ wherein $X_9$ and $X_{10}$ each independently comprise H or alkyl;

m is an integer from 0 to 7;

j is an integer from 0 to about 6;

k is an integer from 0 to about 2; and

W comprises H or alkyl.

In a variation of formula I R1 and R2 each independently comprise -T-$(CH_2)_n$—Z;

n comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 3 independently selected heteroatoms as ring members fused to an unsaturated ring having 6 or 7 ring atoms and 0 to 4 independently selected heteroatoms as ring members.

In a variation of formula I R1 and R2 each independently comprise -T-$(CH_2)_m$-$Q_1$-$(CH_2)_n$—Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

$Q_1$ comprises NH, O, S, CH=CH, C≡C, CO, $SO_2$ or $OSO_2$;

Z comprises H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, O-aroyl, $O(CH_2)_jOX_3$, $O(CH_2)_jNX_1X_2$, alkyl-CN, NH-acyl, NH-aroyl, CHO, C(halogen)$_3$, $COOX_3$, $SO_3H$, $SO_2NX_1X_2$, $CONX_1X_2$, NHC(O)O-alkyl, NHSO2-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, NO, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)alkyl$, $NX_1X_2$, $COOX_3$, $CONX_3$, $OX_7$, or O-alkyl-$X_7$, wherein $X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$, wherein $X_9$ and $X_{10}$ each independently comprise H or alkyl;

m is an integer from 0 to 7;

j is an integer from 0 to about 6; and k is an integer from 0 to about 2

In a variation of formula I R1 and R2 each independently comprise -T-$(CH_2)_m$-$Q_1$-$(CH_2)_n$—Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

$Q_1$ comprises NH, O, S, CH=CH, C≡C, CO, $SO_2$ or $OSO_2$;

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of formula I R1 and R2 each independently comprise -T-$(CH_2)_m$-$Q_1$-$(CH_2)_n$—Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

$Q_1$ comprises NH, O, S, CH=CH, C≡C, CO, $SO_2$ or $OSO_2$;

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of formula I R1 and R2 each independently comprise -T-$(CH_2)_m$-$Q_1$-$(CH_2)_n$—Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

$Q_1$ comprises NH, O, S, CH=CH, C≡C, CO, $SO_2$ or $OSO_2$;

Z comprises wherein X and Y each independently comprise, H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, alkyl-CN, O-aroyl, $O(CH_2)_jOX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, NHC(O)O-alkyl, NHSO2-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, $(CH_2)_m$CN, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$, wherein $X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$, wherein $X_9$ and $X_{10}$ each independently comprise H or alkyl;

m is an integer from 0 to 7;

j is an integer from 0 to about 6;

k is an integer from 0 to about 2; and

W comprises H or alkyl.

In a variation of formula I R1 and R2 each independently comprise -T-$(CH_2)_m$-$Q_1$-$(CH_2)_n$—Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

$Q_1$ comprises NH, O, S, CH=CH, C≡C, CO, $SO_2$ or $OSO_2$; and

Z comprises an unsaturated ring having 5 ring atoms and 0 to 2 independently selected heteroatoms as ring members fused to an unsaturated ring having 5 ring atoms and 0 to 2 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 3 independently selected heteroatoms as ring members fused to an unsaturated ring having 6 or 7 ring atoms and 0 to 4 independently selected heteroatoms as ring members.

In a variation of formula I, R1 and R2 each independently comprise -T-$(CH_2)_m$-$Q_1$-$(CH_2)_n$—Z;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

m and n independently comprises an integer from 0 to about 7;

$Q_1$ comprises NH, O, S, CH=CH, C≡C, CO, $SO_2$ or $OSO_2$;

Z comprises:

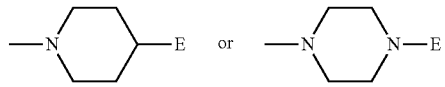

wherein E comprises a C1 to about C4, linear or branched alkyl group, a phenyl group, a substituted phenyl group, a benzyl group or a substituted benzyl group.

In a variation of formula I, R1 and R2 each independently comprise -T-$(CH_2)_m$-$Q_1$-$(CH_2)_n$—Z;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

m and n independently comprises an integer from 0 to about 7;

$Q_1$ comprises NH, O, S, CH=CH, C≡C, CO, $SO_2$ or $OSO_2$;

Z comprises

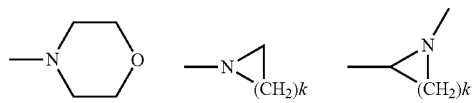

-continued

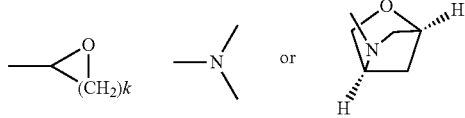 or 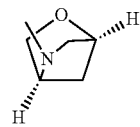

wherein k is an integer from 1 to about 5. $A_1$ and $A_2$ each independently comprise a C1 to about C4 alkyl group, a phenyl group or a substituted phenyl group.

In a variation of formula I, R3 comprises a carbocyclic ring having about 4 to about 7 members, a heterocyclic ring having about 4 to about 7 members, an aromatic ring having about 5 to about 7 ring members, a heteroaromatic ring having about 5 to about 7 members, a bicyclic ring, a heterobicyclic ring, a tricyclic ring, a heterotricyclic ring, a polycyclic ring or a heteropolycyclic ring.

In a variation of formula I, R3 comprises

wherein G comprises CH, $C(CH_3)$, C(CN) or N;

L, K and J each independently comprise $(CH_2)_n$, $(CH_3)_2$, C=O, O, —CHOH, $C(CH_3)OM_1$, $C(CH_2)_n(X)Y$, $NM_1$, $SO_2$ SO or S;

n is an integer from 0 to about 7;

$M_1$ is H, alkyl, $C(O)M_2$, wherein $M_2$ is H, alkyl, $NM_3M_4$, $OM_5$ and $M_3$, $M_4$ and $M_5$ are independently H, OH or alkyl, and X and Y each independently comprise, H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, alkyl-CN, O-aroyl, $O(CH_2)_jOX_3$, $O(CH_2)_jNX_1X_2$, NH-acyl, NH-aroyl, CHO, $C(halogen)_3$, $COOX_3$, $SO_3H$, $SO_2NX_1X_2$, $CONX_1X_2$, NHC(O)O-alkyl, NHSO2-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, $(CH_2)_mCN$, hydroxylower-alkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$, wherein $X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$, wherein $X_9$ and $X_{10}$ each independently comprise H or alkyl;

m is an integer from 0 to 7;

j is an integer from 0 to about 6; and k is an integer from 0 to about 2.

In a variation of formula I, R3 comprises

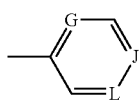

wherein G, L and J each independently comprise CH or N.
In a variation of formula I, R3 comprises

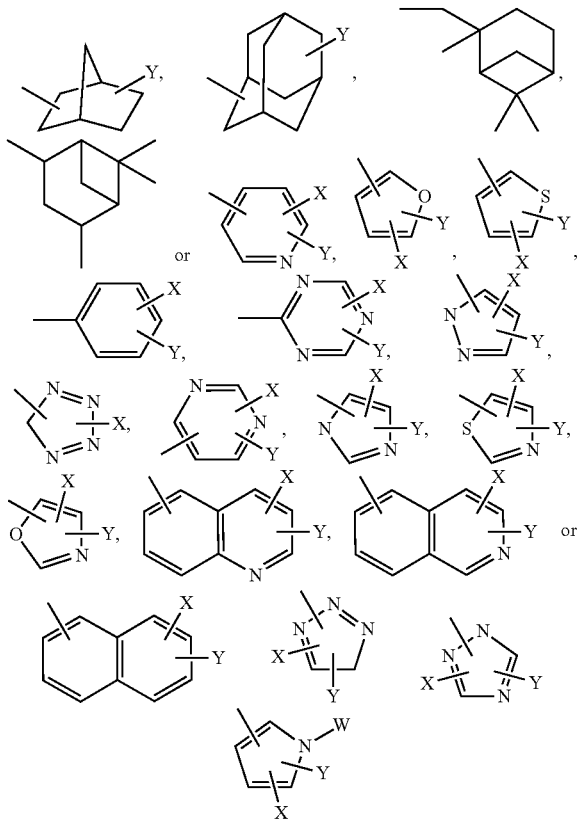

wherein X and Y each independently comprise, H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, alkyl-CN, O-aroyl, $O(CH_2)_jOX_3$, $O(CH_2)_jNX_1X_2$, NH-acyl, NH-aroyl, CHO, $C(halogen)_3$, $COOX_3$, $SO_3H$, $SO_2NX_1X_2$, $CONX_1X_2$, NHC(O)O-alkyl, $NHSO2$-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$, wherein $X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$, wherein $X_9$ and $X_{10}$ each independently comprise H or alkyl;

m is an integer from 0 to 7;

j is an integer from 0 to about 6;

k is an integer from 0 to about 2; and

W comprises H or alkyl.

In a variation of formula I, R3 comprises a carbocyclic ring having 6 ring atoms fused to a heterocyclic ring having from 5 to 7 ring atoms, a carbocyclic ring having 6 ring atoms fused to a heteroaromatic ring having from 5 to 7 ring atoms, a heterocyclic ring having 6 ring atoms fused to a heterocyclic ring having from 5 to 7 ring atoms, a heterocyclic ring having 6 ring atoms fused to a heteroaromatic ring having from 5 to 7 ring atoms, an aromatic ring having 6 ring atoms fused to a heterocyclic ring having from 5 to 7 ring atoms, an aromatic ring having 6 ring atoms fused to a heteroaromatic ring having from 5 to 7 ring atoms, a heteroaromatic ring having 6 ring atoms fused to a heterocyclic ring having from 5 to 7 ring atoms or a heteroaromatic ring having 6 ring atoms fused to a heteroaromatic ring having from 5 to 7 ring atoms.

In a variation of formula I, R4 comprises H, halogen, $CF_3$, $CF_2H$, $N_3$, NCS, CN, $NO_2$, phenyl, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, alkyl-CN, O-aroyl, $O(CH_2)_jOX_3$, $O(CH_2)_jNX_1X_2$, NH-acyl, NH-aroyl, CHO, $C(halogen)_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$, wherein $X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$, wherein $X_9$ and $X_{10}$ each independently comprise H or alkyl;

m is an integer from 0 to 7;

j is an integer from 0 to about 6; and k is an integer from 0 to about 2.

In a variation of formula I, R4 comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring or a heteropolycyclic ring.

In an advantageous variation of formula I, R4 comprises

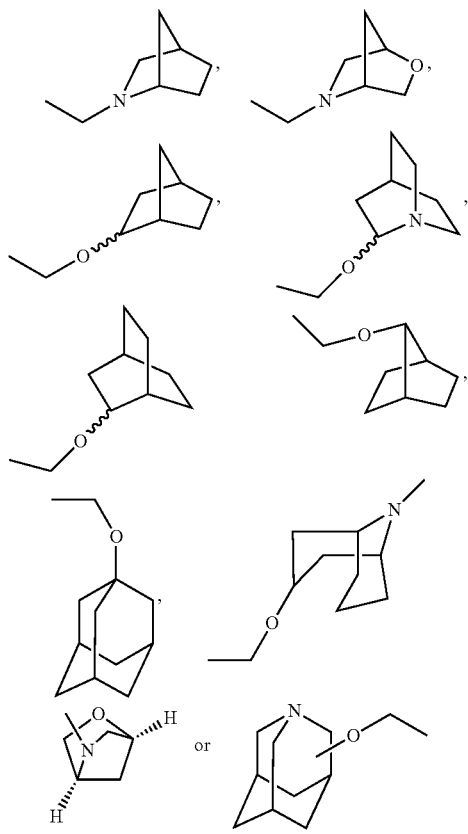

In a variation of formula I, R4 comprises —(CH$_2$)$_d$—Z;
d is an integer from 1 to about 6;
comprises H, halogen, CF$_3$, CF$_2$H, N$_3$, NCS, ON, NO$_2$, phenyl, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, NO$_2$, (CH$_2$)$_m$CN, hydroxyloweralkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$, wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein X$_8$ comprises H, alkyl, carbocyclic ring, heterocyclic ring, aromatic ring, heteroaromatic ring, or —CX$_9$=CHX$_{10}$, wherein X$_9$ and X$_{10}$ each independently comprise H or alkyl;
m is an integer from 0 to 7;
j is an integer from 0 to about 6; and
k is an integer from 0 to about 2.

In a variation of formula I, R4 comprises —CH$_2$OH or —CH$_2$Oalkyl.

In a variation of formula I, R4 comprises —(CH$_2$)$_d$—Z;
d is an integer from 1 to about 6; and Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_d$— group and the Z group can be any available ring carbon atom or any available ring nitrogen atom.

In a variation of formula I, R4 comprises —(CH$_2$)$_d$—Z;
d is an integer from 1 to about 6; and
Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_d$— group and the Z group can be any available ring carbon atom or any available ring nitrogen atom.

In a variation of formula I, R4 comprises —(CH$_2$)$_m$-Q$_1$-(CH$_2$)$_n$—Z;

Q$_1$ comprises NH, O, S, CH=CH, C≡C, CO, SO$_2$ or OSO$_2$;

m is an integer from 1 to about 7;
n is an integer from 0 to about 7;

Z comprises H, halogen, CF$_3$, CF$_2$H, N$_3$, NCS, ON, NO$_2$, phenyl, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, NO$_2$, (CH$_2$)$_m$CN, hydroxyloweralkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$, wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein X$_8$ comprises H, alkyl, carbocyclic ring, heterocyclic ring, aromatic ring, heteroaromatic ring, or —CX$_9$=CHX$_{10}$, wherein $X_9$ and $X_{10}$ each independently comprise H or alkyl;

m is an integer from 0 to 7;

j is an integer from 0 to about 6; and k is an integer from 0 to about 2.

In a variation of formula I, R4 comprises —$(CH_2)_m$-$Q_1$-$(CH_2)_n$—Z;

$Q_1$ comprises NH, O, S, CH=CH, C≡C, CO, $SO_2$ or $OSO_2$;

m is an integer from 1 to about 7;

n is an integer from 0 to about 7; and

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members; a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of formula I R4 comprises —$(CH_2)_m$-$Q_1$-$(CH_2)_n$—Z.

$Q_1$ comprises NH, O, S, CH=CH, C≡C, CO, $SO_2$ or $OSO_2$.

m is an integer from 1 to about 7.

n is an integer from 0 to about 7.

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of formula I R4 comprises —$(CH_2)_m$-$Q_1$-$(CH_2)_n$—Z.

$Q_1$ comprises NH, O, S, CH=CH, C≡C, CO, $SO_2$ or $OSO_2$.

m is an integer from 1 to about 7.

n is an integer from 0 to about 7.

Z comprises

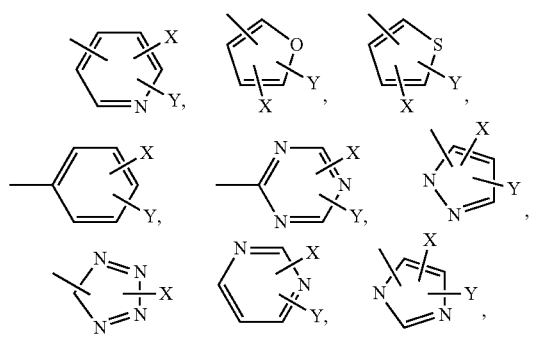

-continued

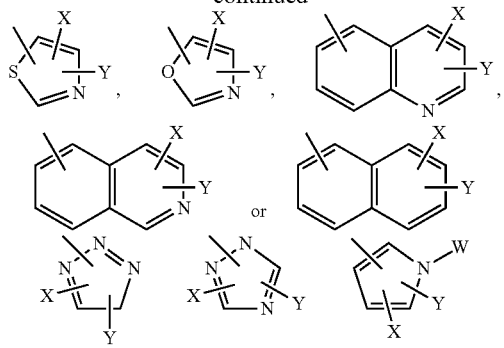

wherein X and Y each independently comprise, H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, alkyl-CN, O-aroyl, $O(CH_2)_jOX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$, wherein $X_7$ comprises H, alkyl, $NO_2$, NO, $P(O)(OX_8)_2$, PH(O)$(OX_8)$, $S(O)_kN$(alkyl)$_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$, wherein $X_9$ and $X_{10}$ each independently comprise H or alkyl;

m is an integer from 0 to 7;

j is an integer from 0 to about 6;

k is an integer from 0 to about 2;

W comprises H or alkyl.

In any variation of formula I, when A is a direct bond; and B is N(R5); and either of R1 and R2 is phenyl [optionally substituted with one more halogen atoms, ($C_1$-$C_6$)alkyl, ($C_1$-$C_6$)alkoxy, trifluoromethyl, cyano, nitro, ($C_1$-$C_6$)alkyl sulfonyl, ($C_1$-$C_6$)alkyl sulfonyl amino, ($C_1$-$C_6$)alkyl carbonylamino, ($C_1$-$C_6$)alkyl amino-carbonyl-amino or phenyl], ($C_2$-$C_6$) alkyl, cyclohexyl [optionally substituted with ($C_1$-$C_6$) alkyl, ($C_1$-$C_6$)alkoxy, trifluoromethyl, cyano or one or more fluorine atoms], 1-napthyl or 2-napthyl [optionally substituted with one or more halogen atoms, ($C_1$-$C_6$)alkyl, ($C_1$-$C_6$) alkoxy, trifluoromethyl or cyano], benzyl [optionally substituted on the phenyl ring with one or more halogen atoms, ($C_1$-$C_6$)alkyl, ($C_1$-$C_6$)alkoxy, trifluoromethyl or cyano], a 5- to 10-membered saturated or unsaturated heterocyclic radical [optionally substituted with one or more fluorine atoms, ($C_1$-$C_6$)alkyl, ($C_1$-$C_6$)alkoxy, trifluoromethyl or cyano] and a 5- to 10-membered aromatic monocyclic or bicyclic heterocyclic radical [optionally substituted with one more halogen atoms, ($C_1$-$C_6$) alkyl, ($C_1$-$C_6$)alkoxy, trifloromethyl, cyano, nitro or phenyl] and R3 is any above described variation; then R4 can not be H, ($C_1$-$C_6$)alkyl, benzyl, chloro, or bromo.

In any variation of formula I, when A is a direct bond; and B is N(R5); and either R1 or R2 is phenyl, thienyl, 2-pyridinyl, 3-pyridinyl, 4-pyridinyl, pyrimidinyl, pyrazinyl, pyridazinyl, triazinyl or any above group substituted with 1, 2, 3 or 4 substituents which can be the same or different, selected from $C_{1-3}$ alkyl, $C_{1-3}$ alkoxy, hydroxy, halogen, trifluoromethyl, trifluoromethylthio, trifluoromethoxy, nitro, amino, mono- or dialkyl ($C_{1-2}$)-amino, mono- or dialkyl ($C_{1-2}$)-amido, ($C_{1-3}$)-alkoxycarbonyl, carboxyl, cyano, carbomyl, acetyl and naphthyl; and R3 is any above described variation; then R4 can not be H, halogen, CN, carbomyl, formyl, acetyl, trifluoroacetyl, fluoroacetyl, propionyl, sulfamoyl, methanesulfonyl, methylsulfanyl, branched or unbranched $C_{1-4}$ alkyl group, which $C_{1-4}$ alkyl group may be substituted with 1 to 3 fluoro atoms or with a single bromo, chloro, iodo, cyano or hydroxy group.

Another embodiment of the invention comprises cannabimimetic thiazole and oxazole ligands represented by formula II and their enantiomers, diastereomers, geometric isomers, racemates, tautomers, rotamers, atropisomers, metabolites, in vivo hydrolysable esters, N-oxides, salts, solvates, hydrates, polymorphic forms (crystalline or amorphous) or pro-drugs:

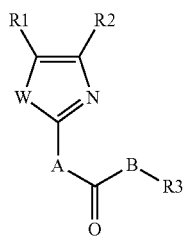

II wherein A, B, R1, R2 and R3 are as defined above for compounds of formula

W comprises S or O.

In any variation of formula II, when A is a direct bond; B is NR5 as defined above; R1 and R3 are any above described variation; and W is S; then R2 cannot be a phenyl group with one or more substituents selected from branched or unbranched $C_{1-3}$-alkyl, branched or unbranched $C_{1-3}$-alkoxy, hydroxy, halogen, $CF_3$, trifluoromethylthio, trifluoromethoxy, nitro, amino, mono- or dialkyl($C_{1-2}$)-amino, mono- or dialkyl($C_{1-2}$)-amido, branched or unbranched ($C_{1-3}$)-alkoxycarbonyl, trifluoromethylsulfonyl, sulfamoyl, branched or unbranched ($C_{1-3}$)-sulfonyl, carboxyl, cyano, carbamoyl, branched or unbranched dialkyl($C_{1-3}$)-aminosulfonyl, branched or unbranched monoalkyl ($C_{1-3}$)-aminosulfonyl and acetyl.

Another embodiment of the invention comprises cannabimimetic triazole ligands represented by formula III and their enantiomers, diastereomers, geometric isomers, racemates, tautomers, rotamers, atropisomers, metabolites, in vivo hydrolysable esters, N-oxides, salts, solvates, hydrates, polymorphic forms (crystalline or amorphous) or pro-drugs:

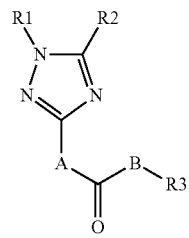

III wherein A, B, R1, R2 and R3 are as defined above for compounds of formula I.

In any variation of formula III, when A is a direct bond; B is NR5; R3 is any above described variation; then either or both of R1 and R2 cannot be a phenyl, naphthyl, thienyl, pyridyl, pyrimidyl, pyrazinyl, pyridazinyl, or triazinyl group, or any above group substituted with 1-4 substituents, which can be same or different, selected from branched or unbranched ($C_{1-3}$)alkyl or alkoxy, hydroxy, halogen, trifluoromethyl, trifluoromethylthio, trifluoromethoxy, nitro, amino, mono- or dialkyl ($C_{1-2}$)-amino, mono- or dialkyl ($C_{1-2}$)-amido, ($C_{1-3}$)-alkoxycarbonyl, trifluoromethylsulfonyl, sulfomyl, ($C_{1-3}$)-alkylsulfonyl, carboxyl, cyano, carbomyl, ($C_{1-3}$)-dialkylaminosulfonyl, ($C_{1-3}$)-monoalkylamino-sulfonyl and acetyl.

Another embodiment of the invention comprises cannabimimetic pyrazole ligands represented by formula IV and their enantiomers, diastereomers, geometric isomers, racemates, tautomers, rotamers, atropisomers, metabolites, in vivo hydrolysable esters, N-oxides, salts, solvates, hydrates, polymorphic forms (crystalline or amorphous) or pro-drugs:

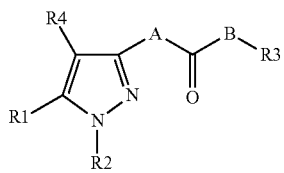

IV wherein A, B, R2 and R3 are as defined above for compounds of formula I.

In a variation of formula IV, R1 comprises -T-($CH_2$)$_m$-Q-($CH_2$)$_n$—Z.

m and n independently comprises an integer from 0 to about 7.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

Q comprises CH═CH, C≡C.

Z comprises H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, SC($CH_3$)$_2$COOX$_8$, OC($CH_3$)$_2$COOX$_8$, C($CH_3$)$_2$COOX$_8$, Si(alkyl)$_3$, O-aroyl, O($CH_2$)$_j$OX$_3$, O($CH_2$)$_j$NX$_1$X$_2$, alkyl-CN, NH-acyl, NH-aroyl, CHO, C(halogen)$_3$, COOX$_3$, $SO_3$H, $SO_2$NX$_1$X$_2$, CONX$_1$X$_2$, NHC(O)O-alkyl, NHSO$_2$-alkyl alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, NO, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$, wherein $X_7$ comprises H, alkyl, $NO_2$, NO, $P(O)(OX_8)_2$, PH(O) $(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$, wherein $X_9$ and $X_{10}$ each independently comprise H or alkyl;

m is an integer from 0 to 7;

j is an integer from 0 to about 6; and k is an integer from 0 to about 2.

In a variation of formula IV R1 comprises -T-$(CH_2)_m$-Q-$(CH_2)_n$—Z.

m and n independently comprises an integer from 0 to about 7.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

Q comprises CH=CH, C≡C.

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of formula IV, R1 comprises -T-$(CH_2)_m$-Q-$(CH_2)_n$—Z.

m and n independently comprises an integer from 0 to about 7.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

Q comprises CH=CH, C≡C.

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of formula IV, R1 comprises -T-$(CH_2)_m$-Q-$(CH_2)_n$—Z.

m and n independently comprises an integer from 0 to about 7.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

Q comprises CH=CH, C≡C.

Z comprises wherein X and Y each independently comprise, H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, alkyl-CN, O-aroyl, $O(CH_2)_jOX_3$, $O(CH_2)_jNX_1X_2$, NH-acyl, NH-aroyl, CHO, $C(halogen)_3$, $COOX_3$, $SO_3H$, $SO_2NX_1X_2$, $CONX_1X_2$, NHC(O)O-alkyl, $NHSO_2$-alkyl alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, $(CH_2)_m CN$, hydroxylower-alkyl, or alkyl-$NX_1 X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1 X_2$, $COOX_3$, $CONX_3$, $OX_7$, or O-alkyl-$X_7$, wherein $X_7$ comprises H, alkyl, $NO_2$, NO, $P(O)(OX_8)_2$, $PH(O)(OX_8)$, $S(O)_k N(alkyl)_2$, $S(O)_k X_8$, $S(O)_k OX_8$, $COOX_8$, $CONX_8$, $SO_3 H$, $COX_8$, wherein $X_8$ comprises H, alkyl, carbocyclic ring, heterocyclic ring, aromatic ring, heteroaromatic ring, or $-CX_9=CHX_{10}$, wherein $X_9$ and $X_{10}$ each independently comprise H or alkyl;

m is an integer from 0 to 7;

j is an integer from 0 to about 6;

k is an integer from 0 to about 2; and

W comprises H or alkyl.

In a variation of formula IV, R1 comprises -T-$(CH_2)_m$-Q-$(CH_2)_n$—Z.

m and n independently comprises an integer from 0 to about 7.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

Q comprises CH=CH, C≡C.

Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 3 independently selected heteroatoms as ring members fused to an unsaturated ring having 6 or 7 ring atoms and 0 to 4 independently selected heteroatoms as ring members In a variation of formula IV, R1 comprises -T-$(CH_2)_m$-Q-$(CH_2)_n$—Z.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

m and n independently comprises an integer from 0 to about 7.

Q comprises CH=CH, C≡C.

Z comprises

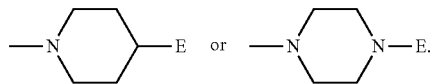

E comprises a C1 to about C4, linear or branched alkyl group, a phenyl group, a substituted phenyl group, a benzyl group or a substituted benzyl group.

In a variation of formula IV, R1 comprises -T-$(CH_2)_m$-Q-$(CH_2)_n$—Z.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

m and n independently comprises an integer from 0 to about 7.

Q comprises CH=CH, C≡C.

Z comprises

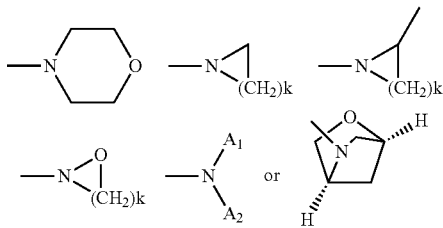

k is an integer from 1 to about 5. $A_1$ and $A_2$ each independently comprise a C1 to about C4 alkyl group, a phenyl group or a substituted phenyl group.

The inventive compounds in any formula, embodiment or variation include any and all possible isomers and steroisomers. In general, the compositions of the invention may be alternately formulated to comprise, consist of, or consist essentially of, any appropriate components herein disclosed. The compositions of the invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

Unless otherwise specifically defined, "acyl" refers to the general formula —C(O)alkyl.

Unless otherwise specifically defined, "acyloxy" refers to the general formula —O-acyl.

Unless otherwise specifically defined, "alcohol" refers to the general formula alkyl-OH and includes primary, secondary and tertiary variations.

Unless otherwise specifically defined, "alkyl" or "lower alkyl" refers to a linear, branched or cyclic alkyl group having from 1 to about 10 carbon atoms, and advantageously 1 to about 7 carbon atoms including, for example, methyl, ethyl, propyl, butyl, hexyl, octyl, isopropyl, isobutyl, tert-butyl, cyclopropyl, cyclohexyl, cyclooctyl, vinyl and allyl. The alkyl group can be saturated or unsaturated. The alkyl group can be unsubstituted, singly substituted or, if possible, multiply substituted, with substituent groups in any possible position. Unless otherwise specifically limited, a cyclic alkyl group includes monocyclic, bicyclic, tricyclic, tetracyclic and polycyclic rings, for example norbornyl, adamantyl and related terpenes.

Unless otherwise specifically defined, "alkoxy" refers to the general formula —O-alkyl.

Unless otherwise specifically defined, "alkylmercapto" refers to the general formula —S-alkyl.

Unless otherwise specifically defined, "alkylamino" refers to the general formula —(NH)-alkyl.

Unless otherwise specifically defined, "di-alkylamino" refers to the general formula —N-(alkyl)$_2$. Unless otherwise specifically limited di-alkylamino includes cyclic amine compounds such as piperidine and morpholine.

Unless otherwise specifically defined, an aromatic ring is an unsaturated ring structure having about 5 to about 7 ring members and including only carbon as ring atoms. The aromatic ring structure can be unsubstituted, singly substituted or, if possible, multiply substituted, with substituent groups in any possible position.

Unless otherwise specifically defined, "aryl" refers to an aromatic ring system that includes only carbon as ring atoms, for example phenyl, biphenyl or naphthyl.

The aryl group can be unsubstituted, singly substituted or, if possible, multiply substituted, with substituent groups in any possible position.

Unless otherwise specifically defined, "aroyl" refers to the general formula —C(=O)-aryl.

Unless otherwise specifically defined, a bicyclic ring structure comprises 2 fused or bridged rings that include only carbon as ring atoms. The bicyclic ring structure can be saturated or unsaturated. The bicyclic ring structure can be unsubstituted, singly substituted or, if possible, multiply substituted, with substituent groups in any possible position. The individual rings may or may not be of the same type. Examples of bicyclic ring structures include naphthalene and bicyclooctane.

Unless otherwise specifically defined, a carbocyclic ring is a non-aromatic ring structure, saturated or unsaturated, having about 3 to about 8 ring members that includes only carbon as ring atoms, for example, cyclohexadiene or cyclohexane. The carbocyclic ring can be unsubstituted, singly substituted or, if possible, multiply substituted, with substituent groups in any possible position.

Unless otherwise specifically defined, "halogen" refers to an atom selected from fluorine, chlorine, bromine and iodine.

Unless otherwise specifically defined, a heteroaromatic ring is an unsaturated ring structure having about 5 to about 8 ring members independently selected from carbon atoms and one or more heteroatoms, including oxygen, nitrogen and/or sulfur, for example, pyridine, furan, quinoline, and their derivatives. The heteroaromatic ring can be unsubstituted, singly substituted or, if possible, multiply substituted, with substituent groups in any possible position.

Unless otherwise specifically defined, a heterobicyclic ring structure comprises 2 fused or bridged rings having ring members independently selected from carbon and one or more heteroatoms, including oxygen, nitrogen and/or sulfur. The heterobicyclic ring structure can be saturated or unsaturated. The heterobicyclic ring can be unsubstituted, singly substituted or, if possible, multiply substituted, with substituent groups in any possible position. The individual rings may or may not be of the same type. Examples of heterobicyclic ring structures include isobenzofuran and indole.

Unless otherwise specifically defined, a heterocyclic ring is a saturated or unsaturated ring structure having about 3 to about 8 ring members independently selected from carbon atoms and one or more heteroatoms, including oxygen, nitrogen and/or sulfur; for example, piperidine, morpholine, piperazine, pyrrolidine, thiomorpholine, 1,1-dioxothiomorpholine and their derivatives. The heterocyclic ring can be unsubstituted, singly substituted or, if possible, multiply substituted, with substituent groups in any possible position.

Unless otherwise specifically defined, a heterotricyclic ring structure comprises 3 fused, bridged, or both fused and bridged rings having ring members independently selected from carbon and one or more heteroatoms, including oxygen, nitrogen and/or sulfur. The heterotricyclic ring structure may be saturated or unsaturated.

The heterotricyclic ring structure can be unsubstituted, singly substituted or, if possible, multiply substituted, with substituent groups in any possible position. The individual rings may or may not be of the same type. Examples of heterotricyclic ring structures include carbazole, phenanthroline, phenazine, 2,4,10-trioxaadamantane and tetradecahydro-phenanthroline.

Unless otherwise specifically defined, a heteropolycyclic ring structure comprises more than 3 rings that may be fused, bridged or both fused and bridged and that have ring members independently selected from carbon and one or more heteroatoms, including oxygen, nitrogen and/or sulfur. The heteropolycyclic ring structure can be saturated or unsaturated. The heteropolycyclic ring structure can be unsubstituted, singly substituted or, if possible, multiply substituted, with substituent groups in any possible position. The individual rings may or may not be of the same type. Examples of heteropolycyclic ring structures include azaadamantine, tropane, homotropane and 5-norbornene-2,3-dicarboximide.

Unless otherwise specifically defined, the term "phenacyl" refers to the general formula -phenyl-acyl.

Unless otherwise specifically defined, a polycyclic ring structure comprises more than 3 rings that may be fused, bridged or both fused and bridged, and that includes carbon as ring atoms. The polycyclic ring structure can be saturated or unsaturated. The polycyclic ring structure can be unsubstituted, singly substituted or, if possible, multiply substituted, with substituent groups in any possible position. The individual rings may or may not be of the same type. Examples of polycyclic ring structures include adamantine, bicyclooctane, norbornane and bicyclononanes.

Unless otherwise specifically defined, a spirocycle refers to a ring system wherein a single atom is the only common member of two rings. A spirocycle can comprise a saturated carbocyclic ring comprising about 3 to about 8 ring members, a heterocyclic ring comprising about 3 to about 8 ring atoms wherein up to about 3 ring atoms may be N, S, or O or a combination thereof.

Unless otherwise specifically defined, a tricyclic ring structure comprises 3 rings that may be fused, bridged or both fused and bridged, and that includes carbon as ring atoms. The tricyclic ring structure can be saturated or unsaturated. The tricyclic ring structure can be unsubstituted, singly substituted or, if possible, multiply substituted, with substituent groups in any possible position. and may be substituted or unsubstituted. The individual rings may or may not be of the same type. Examples of tricyclic ring structures include fluorene and anthracene.

Unless otherwise specifically limited the term substituted means substituted by a below-described substituent group in any possible position. Substituent groups for the above moieties useful in the invention are those groups that do not significantly diminish the biological activity of the inventive compound. Substituent groups that do not significantly diminish the biological activity of the inventive compound include, for example, H, halogen, $N_3$, NCS, CN, $NO_2$, $NX_1X_2$, $OX_3$, $C(X_3)_3$, OAc, O-acyl, O-aroyl, NH-acyl, NH-aroyl, NHCOalkyl, CHO, C(halogen)$_3$, $COOX_3$, $SO_3H$, $PO_3H_2$, $SO_2NX_1X_2$, $CONX_1X_2$, alkyl, alcohol, alkoxy, alkylmercapto, alkylamino, di-alkylamino, sulfonamide, thioalkoxy or methylene dioxy when the substituted structure has two adjacent carbon atoms, wherein $X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members and $X_3$ comprises H, alkyl, hydroxyloweralkyl, or alkyl-$NX_1X_2$. Unless otherwise specifically limited a substituent group may be in any possible position.

Some of the inventive compounds show a high affinity for at least one of the cannabinoid receptors. Thus, another aspect of the invention is use of at least one of the inventive compounds to interact with a cannabinoid receptor.

Some of the novel heteropyrrole derivatives show selectivity for the CB1 cannabinoid receptor. These inventive CB1 selective analogs are able to interact with the CB1 cannabinoid receptors present in the CNS as well as the periphery without affecting the CB2 receptors to the same degree. Therefore, still another aspect of the invention is use of at least one of the inventive compounds to preferentially interact with a CB1 cannabinoid receptors present either in the CNS or the periphery.

The inventive heteropyrrole analogs described herein, and physiologically acceptable salts thereof, have pharmacological properties when administered in therapeutically effective amounts for providing a physiological response. Thus, another aspect of the invention is the administration of a therapeutically effective amount of at least one of the inventive compounds, or a physiologically acceptable salt thereof, to an individual or animal to provide a physiological response.

A better understanding of the invention will be obtained from the following detailed description of the article and the desired features, properties, characteristics, and the relation of the elements as well as the process steps, one with respect to each of the others, as set forth and exemplified in the description and illustrative embodiments.

DETAILED DESCRIPTION

As used herein a "therapeutically effective amount" of a compound, is the quantity of a compound which, when administered to an individual or animal, results in a sufficiently high level of that compound in the individual or animal to cause a physiological response, for example a discernible increase or decrease in stimulation of cannabinoid receptors. The inventive compounds described herein, and physiologically acceptable salts thereof, have pharmacological properties when administered in therapeutically effective amounts individually or in combination for providing a physiological response useful to treat marijuana abuse, obesity, lifestyle choices such as a desire to lose weight, other metabolic disorders including improvement in lipid profiles and insulin related deficiencies, hepatic disease, cardiometabolic diseases, congestive obstructive pulmonary disorders, inflammatory bowel disease, smoking cessation, bone defects, arthritis, inflammation, benign prostatic hypertrophy, asthma, migraine, chronic-intestinal pseudo obstruction, constipation, schizophrenia, epilepsy, stress, memory disorders, migraine, vomiting, thymic disorders, dyskinesia, kinetic disorder, anxiety disorders, psychotic disorders, cognitive disorders, appetite disorders, mood disorders, delirious disorders, neuropathies, Parkinson's disease, Alzheimers disease, depression, psychosomatic-induced disease, diabetes, sexual dysfunctions, as well as for alcohol, opioid, nicotine and cocaine addiction, etc. Additionally, these analogs can be useful in cancer chemotherapy. Typically, a "therapeutically effective amount" of an inventive compound is believed to range from about 0.01 mg/day to about 1,000 mg/day.

As used herein, an "individual" refers to a human. An "animal" refers to, for example nonhuman-primates such as monkeys and baboons, veterinary animals, such as rodents, dogs, cats, horses and the like, and farm animals, such as cows, pigs and the like In a certain embodiments, the compound disclosed in the invention can be used in combination with other acceptable pharmaceutical substances.

In embodiments in which compounds of the disclosure is used in combination with Rimonabant (Accomplia, Sanofi-Aventis) or other CB1 antagonists, it will be possible to reduce or even eliminate one or more of these side-effects, particularly nausea. That is, it is possible to reduce the amount of Rimonabant or other CB1 antagonists administered to the individual who has had, is receiving or is about to receive a therapeutically effective amount of the compound of the disclosure. In one embodiment, the amount of Rimonabant administered to the individual is reduced by 1.5 to 5-fold compared to the accepted therapeutic amount. The individual is then dosed with a therapeutically effective amount of at least one of the compounds of the disclosure. Of course, it is also possible to increase the length of time between doses of Rimonabant with the same or similar effect.

Accordingly, one embodiment provides for a method for reducing unwanted side-effects (one or more of nausea, dizziness, diarrhea, and anxiety) typically associated with administration of SR141716A (Accomplia™/Rimonabant) or other CB1 antagonists to certain individuals. A particular method involves administering a therapeutically effective amount of at least one of the compounds of the disclosure so as to reduce the side-effects in that individual. As discussed, the method can involve reducing the amount of SR141716A (Accomplia™/Rimonabant) or other CB1 antagonists administered to the individual.

As will be apparent, the compounds of the invention can be used alone or in combination with other CB1 receptor antagonists or anti-obesity agents known to the field. Examples of such agents include SR141716A (Acomplia®/Rimonabant, 5-(4-chlorophenyl)-1-(2,4-dichlorophenyl)-4-methyl-N-(piperidin-1-yl)-1H-pyrazole-3-carboxamide), Xenical® (Orlistat, (S)—(S)-1-((2S,3S)-3-hexyl-4-oxooxetan-2-yl)tridecan-2-yl 2-formamido-4-methylpentanoate), Meridia® (Sibutramine, 1-(1-(4-chlorophenyl)cyclobutyl)-N,N,3-trimethylbutan-1-amine,hydrochloride monohydrate), SR147778 (Surinabant, 5-(4-bromophenyl)-1-(2,4-dichlorophenyl)-4-ethyl-N-(piperidin-1-yl)-1H-pyrazole-3-carboxamide), AVE-1625 (Drinabant, N-[1-[bis(4-chlorophenyl)methyl]-3-azetidinyl]-N-(3,5-difluorophenyl)-methanesulfonamide), CP-945,598 (Otenabant, 1-[8-(2-Chlorophenyl)-9-(4-chlorophenyl)-9H-purin-6-yl]-4-(ethylamino)piperidine-4-carboxamide), E-6776 (Rosonabant, 5-(4-chlorophenyl)-1-(2,4-dichlorophenyl)-N-(piperidin-1-yl)-4,5-dihydro-1H-pyrazole-3-carboxamide), MK-0364 (Taranabant, N-((2S,3S)-4-(4-chlorophenyl)-3-(3-cyanophenyl)butan-2-yl)-2-methyl-2-((5-(trifluoromethyl)pyridin-2-yl)oxy)propanamide), SLV-319 (Ibipinabant, (S,E)-3-(4-chlorophenyl)-N'-((4-chlorophenyl)sulfonyl)-N-methyl-4-phenyl-4,5-dihydro-1H-pyrazole-1-carboximidamide), V24343, Qsymia (Qnexa, Phentermine/topiramate, 2-methyl-1-phenylpropan-2-amine and 2,3:4,5-Bis-O-(1-methylethylidene)-β-D-fructopyranose sulfamate), Contrave (Bupropion/naltrexone, 2-(tert-butylamino)-1-(3-chlorophenyl)propan-1-one and 17-(cyclopropylmethyl)-4,5α-epoxy-3,14-dihydroxymorphinan-6-one), Empatic (Bupropion/zonisamide, 2-(tert-butylamino)-1-(3-chlorophenyl)propan-1-one and benzo[d]isoxazol-3-ylmethanesulfonamide), lorcaserin (Belviq, (1R)-8-chloro-1-methyl-2,3,4,5-tetrahydro-1H-3-benzazepine), and Phentermine (2-methyl-1-phenylpropan-2-amine).

Compounds of the invention can also be used in combination with a potassium channel opener, opiod antagonist, anticonvulsant agent, contraceptive agent, antipsychotic agent, anticonstipation agent, nicotine receptor agonist or partial agonist, CB2 agonist, melanin-concentrating hormone receptor antagonist, antipsychotic agents, peroxisome proliferator-activated receptors agonists, ghrelin antagonists, GLP-1 agonist, fatty acid amide hydrolase inhibitor, an intestinal-acting microsomal triglyceride transfer protein inhibitor, a dipeptidyl-peptidase IV inhibitor, a statin, a sterol absorption inhibitor (β-lactam), Beta-3 adrenergic agonist, a biguanide, Sodium glucose transport (SGLT2) antagonist, cyclooxygenase-2 inhibitor, renin inhibitor, monoamine oxidase inhibitor, CETP inhibitor, ACAT inhibitor, DGAT-1 inhibitor, Mitochondrial Transfer Protein inhibitor, noradrenalin-serotonin-dopamine reuptake inhibitor or a lipase inhibitor.

In one embodiment, less than five compounds of the disclosure, preferably one or two of same is used in combination with less than five of the known CB1 antagonists, preferably one or two of same.

In one embodiment, the compound disclosed in the invention could in itself act as a drug with a combination effect. For example compounds disclosed in the invention could dually act as a CB1 antagonist as well as 11β-hydroxy steroid dehydrogenase-1 inhibitor. In certain embodiments, the compound could act dually as a CB1 antagonist as well as a nitric oxide donor.

By "physiologically acceptable salts" is meant, salts typically useful for pharmaceutical applications including acid addition salts and basic salts. Examples of acid addition salts are hydrochloride salts, hydrobromide salts, methane sulfonate salts etc. Examples of basic salts are salts where the cation is selected from alkali metals, such as sodium and potassium, alkaline earth metals, such as calcium, and ammonium ions. Other examples of physiologically acceptable salts can be found in "Remington's Pharmaceutical Sciences" 17. Ed. Alfonso R. Gennaro (Ed.), Mark Publishing Company, Easton, Pa., U.S.A., 1985 and more recent editions, and in Encyclopedia of Pharmaceutical Technology.

Polymorphic forms show improved physiochemical properties and stability for formulation purposes. In one embodiment, the compounds disclosed in the invention could exist in various solid forms. The solid forms can be crystalline and amorphous forms, but not limited to, solvates, hydrates, hydrolyzable esters and N-oxides of the compounds defined in the specification. These solid forms can be obtained by treating either the free base or their salts at a certain adjusted pH and certain temperature with an solvent or a combination of solvents. The solvents can be and not limited to a hydrocarbon solvent such as toluene, xylene, hexanes, heptane, or petroleum ether, alcohol such as methanol, ethanol, n-butanol, n-propanol and 2-propanol, di-isopropyl ether, ethylacetate, dichloromethane, acetic acid, acetone, tetrahydrofuran, dichloromethane, and water.

In one embodiment, in order to improve the dehepaticability of the compound disclosed in the present invention for the required physiological effect, a "pro-drug" of the same can be made available. For example, the pro-drug such as an in-vivo hydrolyzable ester can be a obtained by conjugation of the parent drug with a low-molecular weight alcohol or a high molecular weight polyethylene glycol (PEG). In certain embodiments, the compound disclosed in the invention could contain a nitrate ester group.

In one embodiment, the compounds in the present invention could exist as enantiomers, diastereomers, geometric isomers, racemates, tautomers, rotamers, atropisomers or metabolites.

In one embodiment, some compounds disclosed in the invention can be "neutral antagonists". These agents are said to have no effect on intrinsic receptor activity at least in certain test systems. However, these agents may be able to block receptor binding and activation, usually by a competitive agonist.

In some embodiments, it would be desirable to have antagonists that exhibit essentially no CB1 receptor activity and which block or significantly reduce receptor activation by a suitable agonist. It would be further desirable to have neutral antagonists of the CB1 receptor that can be used to prevent, treat, or reduce the severity of symptoms of certain medical conditions. It would be especially desirable to have neutral antagonists that exhibit no or minimal side-effects in vivo.

In another embodiment, the compound disclosed in the present invention may act preferentially at the CB1 receptors located in the periphery. In certain embodiments, the compounds do not penetrate the blood-brain-barrier, have restricted penetration or have slow penetration. In certain embodiments, peripherally acting compounds may have advantages over centrally acting compounds, for example, reduced psychotropic adverse effects.

A compound acting on the CB1 receptors located in the periphery could be behave either as a neutral antagonist, an inverse agonists or a partial antagonist.

A compound acting on the CB1 receptors located centrally, could behave as a neutral antagonist, an inverse agonists or a partial antagonist.

In another embodiment, the compounds disclosed in the invention could act either as inverse agonists with no or reduced side effects. In other embodiments, the compounds could act as partial agonists with no or reduced side effects.

The compounds of the present invention can be administered by a variety of known methods, including orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular, subcutaneous, ocular, intranasal, inhalation-based and transdermal administration) and slow releasing microcarriers (for rectal, intramuscular or intravenous administration). The formulations can also contain a physiologically acceptable vehicle and optional adjuvants, flavorings, colorants and preservatives. Suitable physiologically acceptable vehicles include, for example, saline, sterile water, Ringer's solution and isotonic sodium chloride solutions. The specific dosage level of active ingredient will depend upon a number of factors, including, for example, biological activity of the particular preparation, age, body weight, sex and general health of the individual being treated.

In another embodiment, the compounds of the present disclosure can also comprise isotopes at one or more of their atoms. For example, the compounds can be radiolabeled with isotopes, such as $^2$H (deuterium written as D) $^3$H (tritium written as T), $^{11}$C (carbon-11), $^{13}$C (carbon-13), $^{14}$C (carbon-14), $^{15}$O (oxygen-15), $^{17}$O (oxygen-17), $^{18}$O (oxygen-18), $^{13}$N (nitrogen-13), $^{15}$N (nitrogen-15), $^{18}$F (fluorine-18), $^{75}$Br (bromine-75), $^{76}$Br (bromine-76), $^{77}$Br (bromine-77), $^{82}$Br (bromine-82), 123I (iodine-123), $^{124}$I (iodine-124), $^{125}$I (iodine-125) or $^{131}$I (iodine-131), $^{36}$Cl (chlorine-36) or $^{35}$S (sulphur-35), The present disclosure encompasses all isotopic variations of the described compounds, whether natural or unnatural, radioactive or not.

An isotope is one of two or more species of the same element. Each isotope of an element will have the same number of protons in its nucleus, the same atomic number and the same position in the Periodic Table. However each isotope of that element will have a different number of neutrons in its nucleus and therefore a different mass than other isotopes of that species. The term nuclide is sometimes used synonymously with the term isotope. As used herein a natural isotope has an atomic mass corresponding most closely with the atomic mass shown for that element in the Periodic Table. As used herein an unnatural isotope has an atomic mass that is further removed from the atomic mass shown for that element in the Periodic Table than the natural isotope. For example, protium (hydrogen-1 or $^1$H) is the natural isotope of hydrogen and deuterium (hydrogen-2 or $^2$H) and tritium (hydrogen-3 or $^3$H) are all unnatural isotopes of hydrogen.

In a particular embodiment, some of the halogen containing analogs, for example those analogs comprising iodide and fluoride, are potential radioactive probes for imaging in vivo the distribution of cannabinoid receptors. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

Some of the radioactive isotope containing analogs have potential as radiopharmaceutical analogs (disclosed analogs that have been labeled with radioactive isotopes). These radiopharmaceuticals can be administered to individuals or animals and the emitted radiation can be measured. The majority of these diagnostic tests involve the formation of an image using a camera suitable to detect the emitted radiation. Positron emission tomography (PET) is one nuclear medicine tomographic imaging technique, which produces a three-dimensional image or map of functional processes in a patient's body. To conduct the PET scan, a short-lived radiopharmaceutical analog that decays by emitting a positron is administered into the subject (usually by injection into the blood stream). There is a waiting period while the radiopharmaceutical analog becomes concentrated in tissues of interest such as a cannabinoid receptor. After the waiting period the patient is placed in an imaging scanner. The scanner collects multiple images and a computer is used to apply an algorithm to the multiple images and provide a three dimensional image. Single photon emission computed tomography (SPECT) is another nuclear medicine tomographic imaging technique. To conduct the SPECT scan, a short-lived radiopharmaceutical analog that decays to produce a gamma ray is administered into the subject. There is a waiting period while the radiopharmaceutical analog becomes concentrated in tissues of interest such as a cannabinoid receptor. After the waiting period the patient is placed in an imaging scanner and SPECT imaging is performed by using a gamma camera to acquire multiple two dimensional images from multiple angles. A computer is then used to apply an algorithm to the multiple images to provide a three dimensional image.

TABLE 1

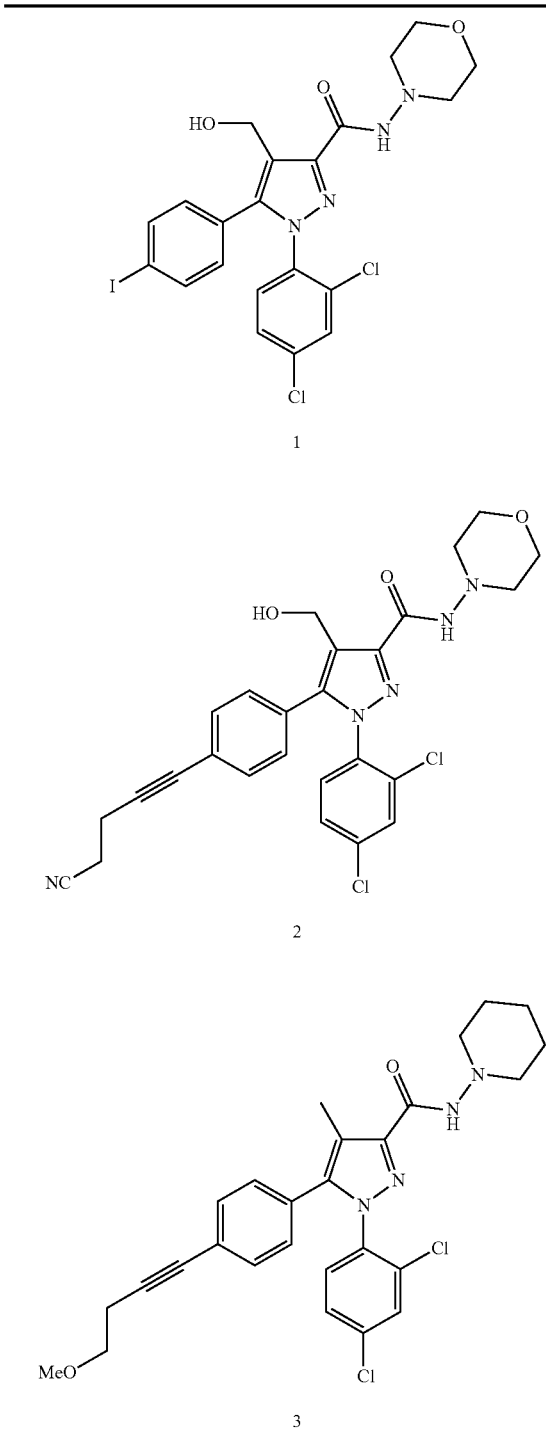

TABLE 1-continued
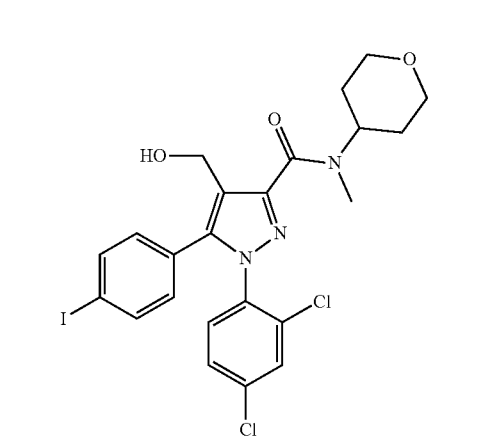 [SMILES: CN(C(=O)c1nn(-c2ccc(Cl)cc2Cl)c(-c2ccc(I)cc2)c1CO)C1CCOCC1]
4
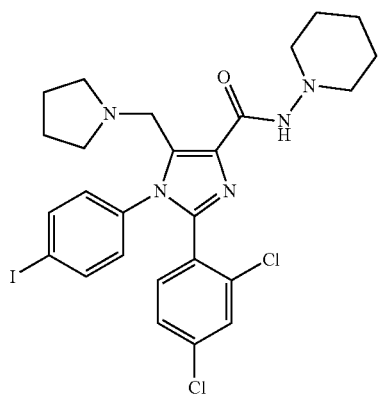 [SMILES: O=C(NN1CCCCC1)c1nc(-c2ccc(Cl)cc2Cl)n(-c2ccc(I)cc2)c1CN1CCCC1]
7
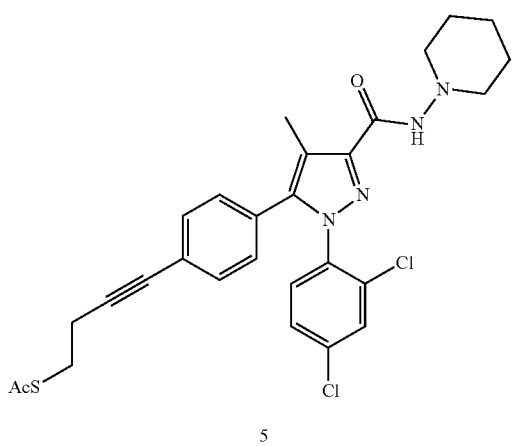
5
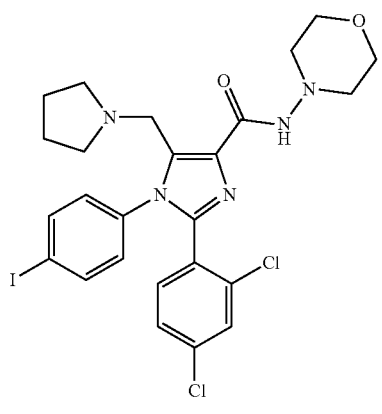 [SMILES: O=C(NN1CCOCC1)c1nc(-c2ccc(Cl)cc2Cl)n(-c2ccc(I)cc2)c1CN1CCCC1]
8
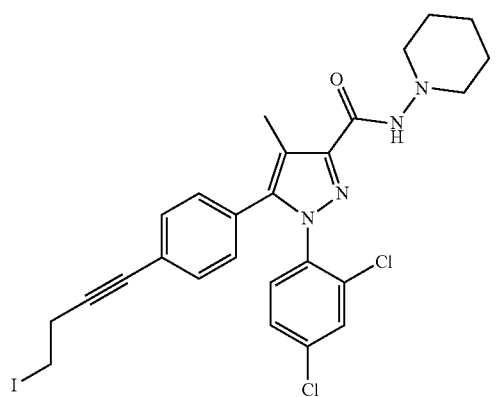
6
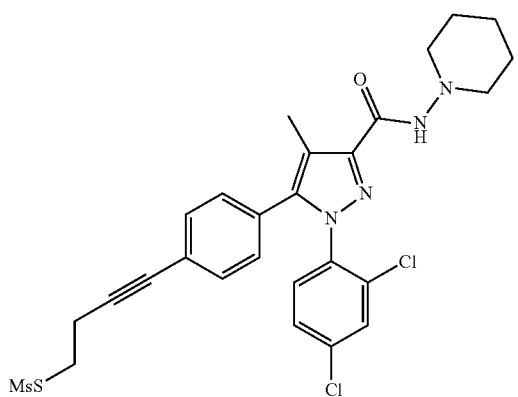
9

TABLE 1-continued
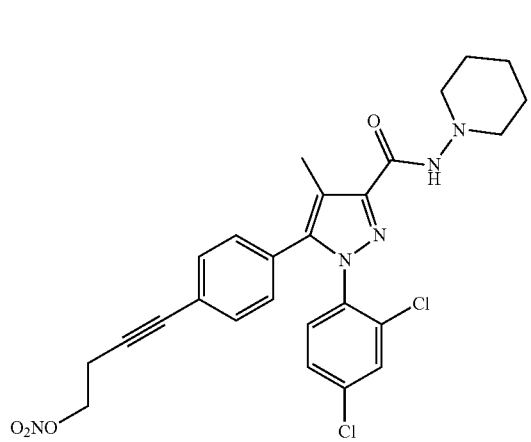
10
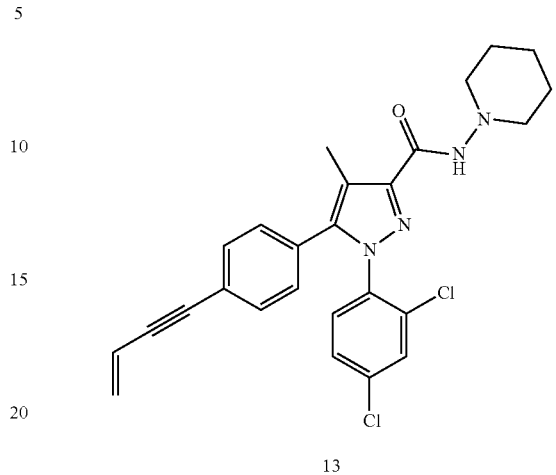
13
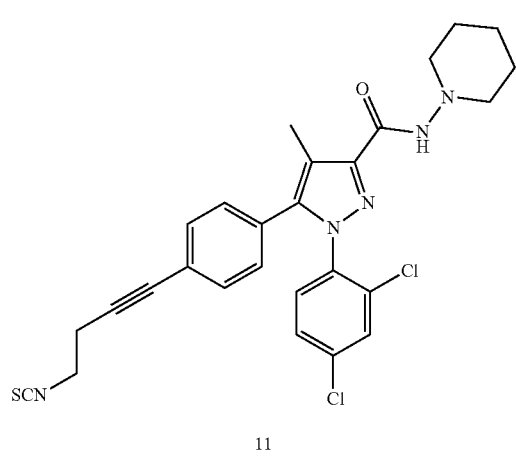
11
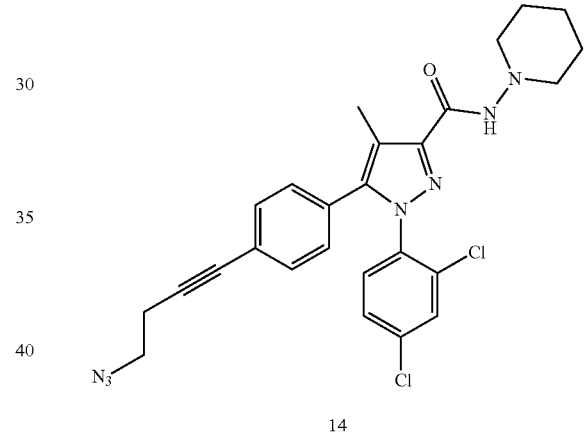
14
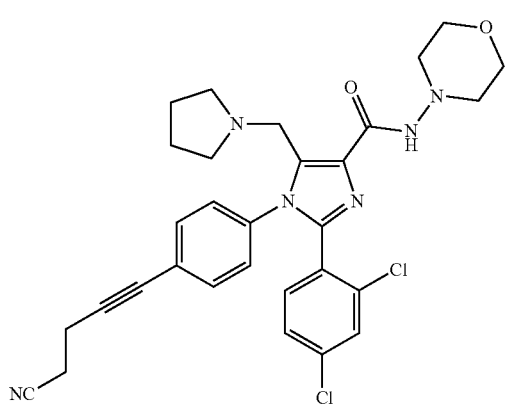 [SMILES: N#CCCC#Cc1ccc(-n2c(-c3ccc(Cl)cc3Cl)nc(C(=O)NN3CCOCC3)c2CN2CCCC2)cc1]
12
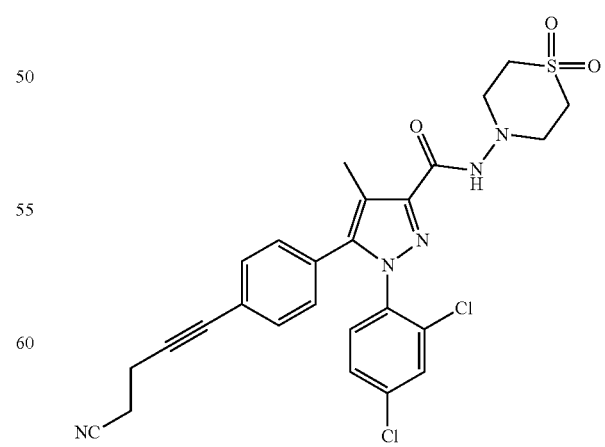
15

TABLE 1-continued
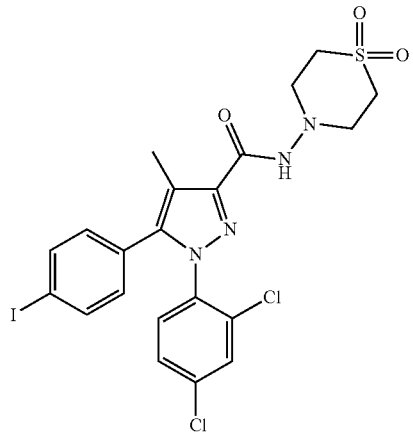 [SMILES: Cc1c(C(=O)NN2CCS(=O)(=O)CC2)nn(-c2ccc(Cl)cc2Cl)c1-c1ccc(I)cc1]
16
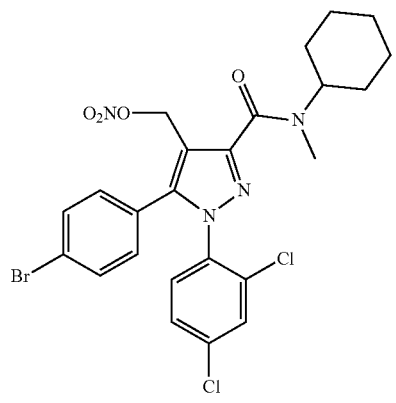
19
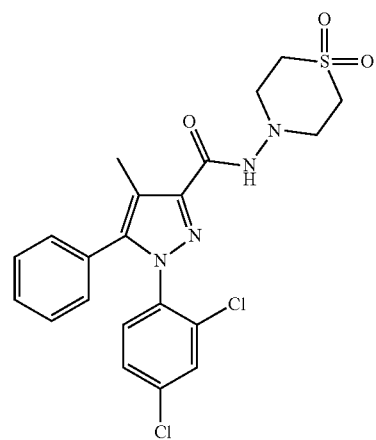 [SMILES: Cc1c(C(=O)NN2CCS(=O)(=O)CC2)nn(-c2ccc(Cl)cc2Cl)c1-c1ccccc1]
17
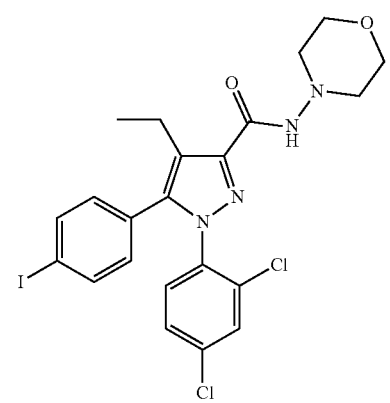
20
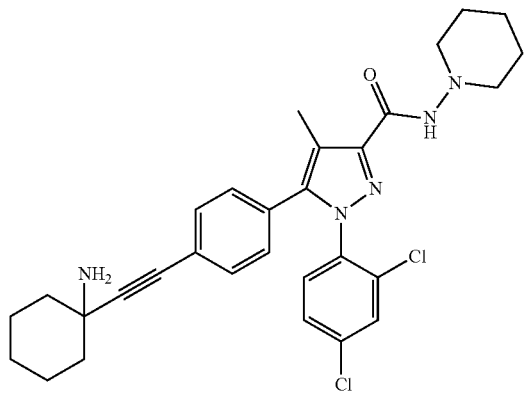 [SMILES: Cc1c(C(=O)NN2CCCCC2)nn(-c2ccc(Cl)cc2Cl)c1-c1ccc(C#CC2(N)CCCCC2)cc1]
18
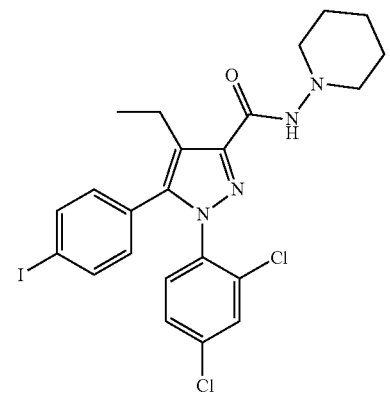 [SMILES: CCc1c(C(=O)NN2CCCCC2)nn(-c2ccc(Cl)cc2Cl)c1-c1ccc(I)cc1]
21

TABLE 1-continued
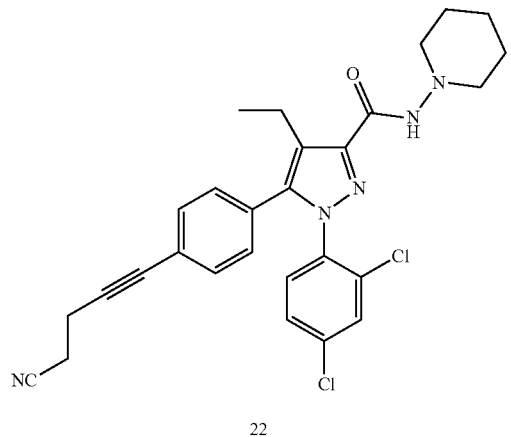
22
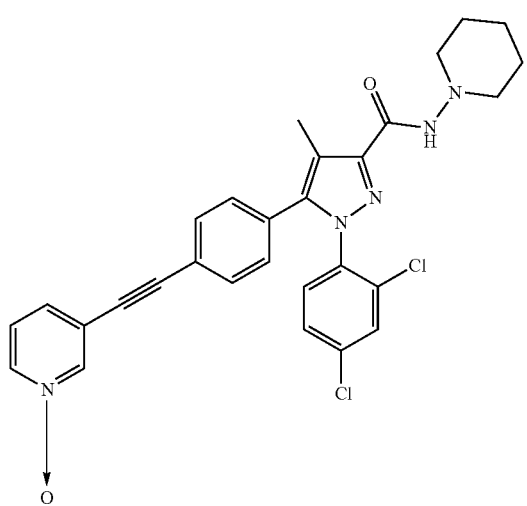 [SMILES: Cc1c(C(=O)NN2CCCCC2)nn(-c2ccc(Cl)cc2Cl)c1-c1ccc(C#Cc2cccnc2)cc1 ; O]
23
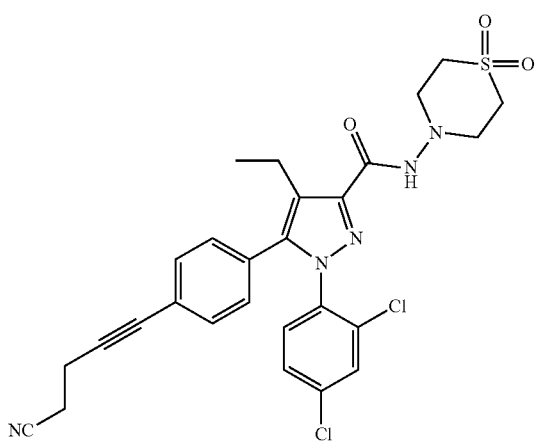 [SMILES: CCc1c(C(=O)NN2CCS(=O)(=O)CC2)nn(-c2ccc(Cl)cc2Cl)c1-c1ccc(C#CCCC#N)cc1]
24
TABLE 1-continued
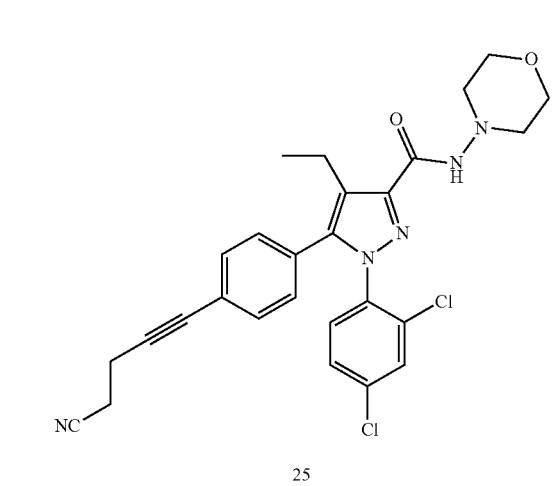
25
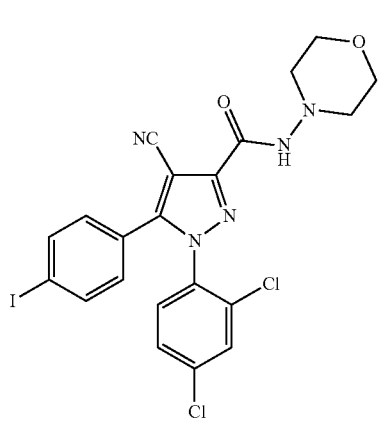 [SMILES: N#Cc1c(C(=O)NN2CCOCC2)nn(-c2ccc(Cl)cc2Cl)c1-c1ccc(I)cc1]
26
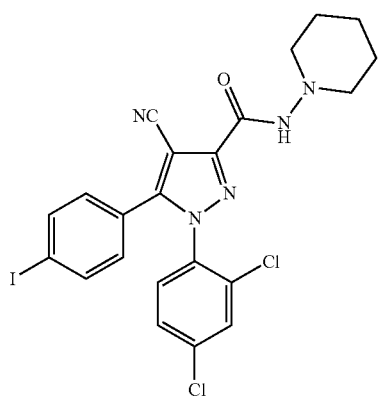 [SMILES: N#Cc1c(C(=O)NN2CCCCC2)nn(-c2ccc(Cl)cc2Cl)c1-c1ccc(I)cc1]
27

TABLE 1-continued
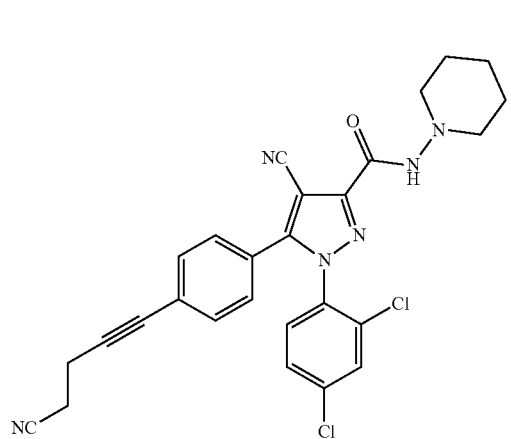 [SMILES: N#CCCC#Cc1ccc(-c2c(C#N)c(C(=O)NN3CCCCC3)nn2-c2ccc(Cl)cc2Cl)cc1]
28
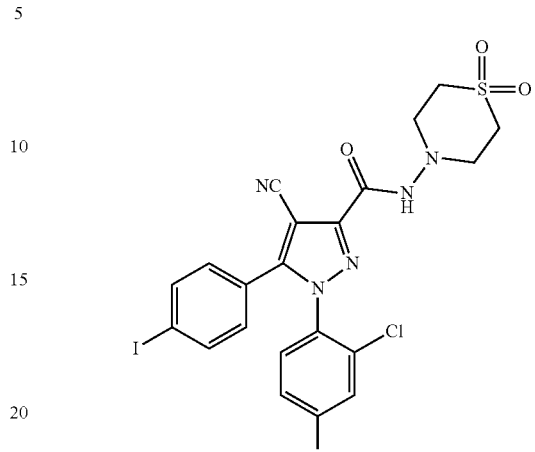
31
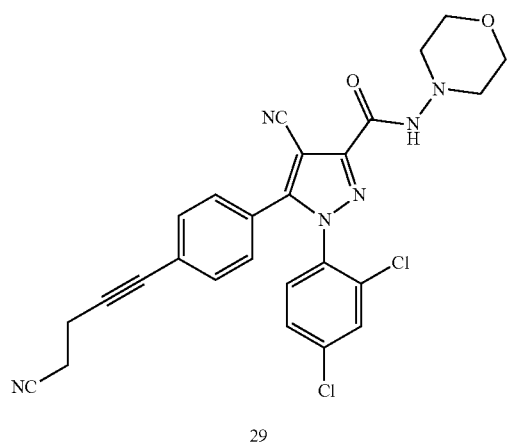
29
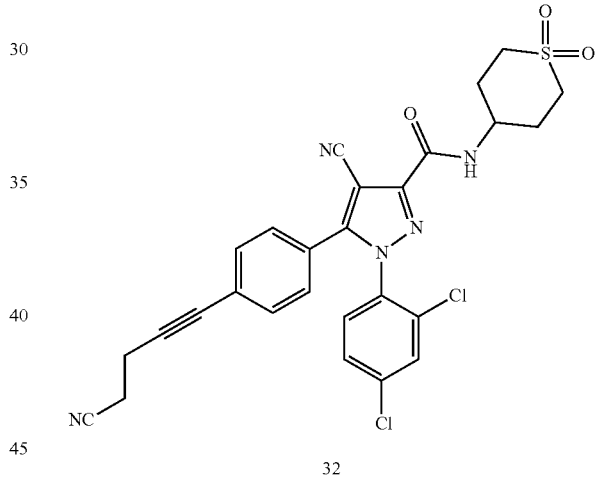
32
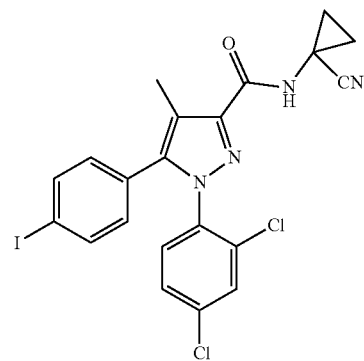 [SMILES: Cc1c(C(=O)NC2(C#N)CC2)nn(-c2ccc(Cl)cc2Cl)c1-c1ccc(I)cc1]
30
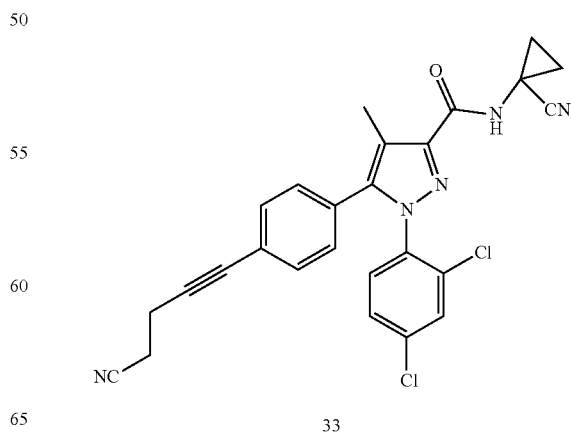
33

TABLE 1-continued
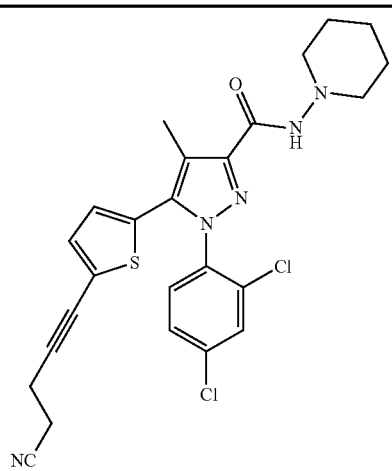
34
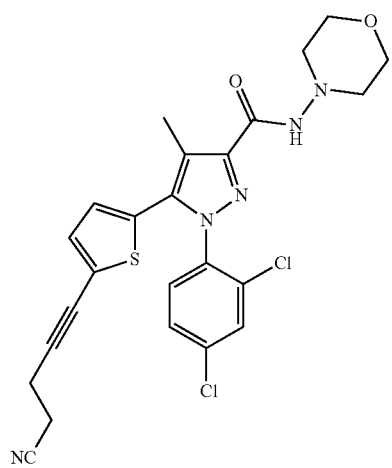 [SMILES: Cc1c(C(=O)NN2CCOCC2)nn(-c2ccc(Cl)cc2Cl)c1-c1ccc(C#CCCC#N)s1]
35
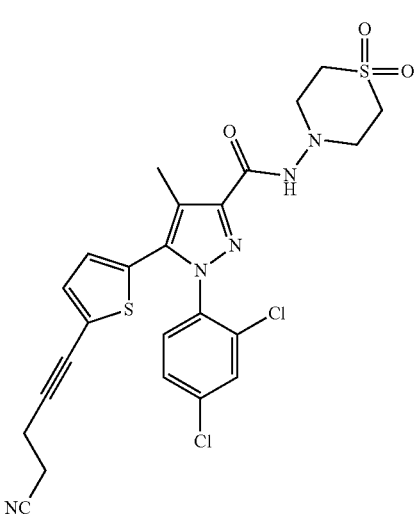 [SMILES: Cc1c(C(=O)NN2CCS(=O)(=O)CC2)nn(-c2ccc(Cl)cc2Cl)c1-c1ccc(C#CCCC#N)s1]
36
TABLE 1-continued
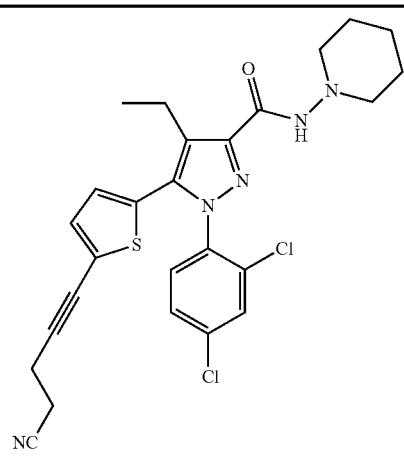
37
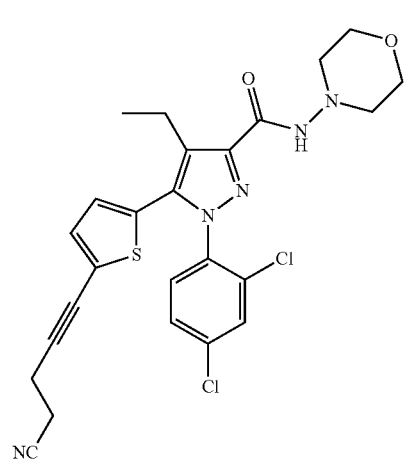 [SMILES: CCc1c(C(=O)NN2CCOCC2)nn(-c2ccc(Cl)cc2Cl)c1-c1ccc(C#CCCC#N)s1]
38
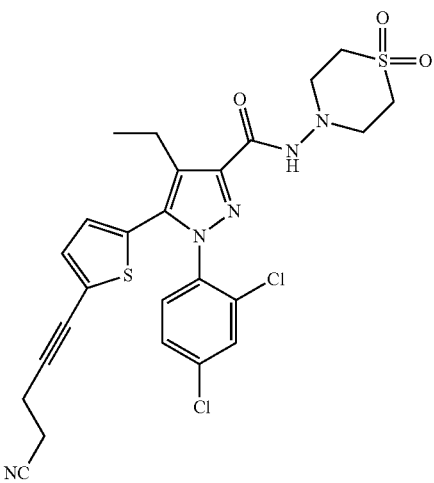 [SMILES: CCc1c(C(=O)NN2CCS(=O)(=O)CC2)nn(-c2ccc(Cl)cc2Cl)c1-c1ccc(C#CCCC#N)s1]
39

TABLE 1-continued
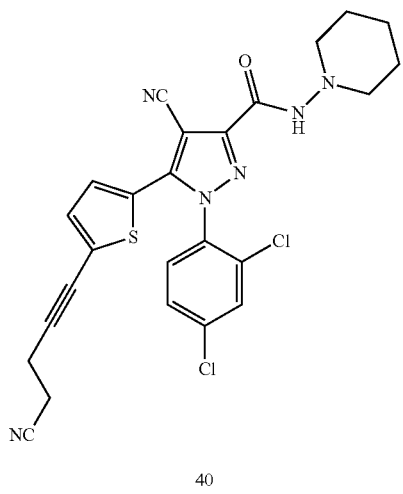
40
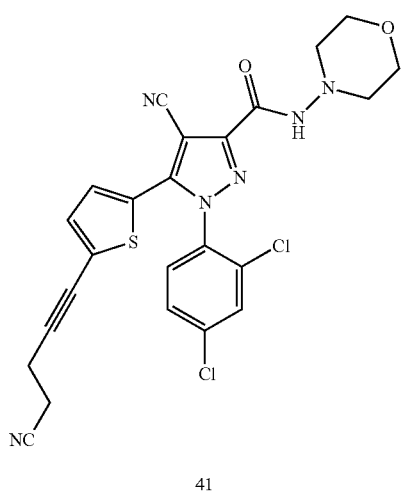
41
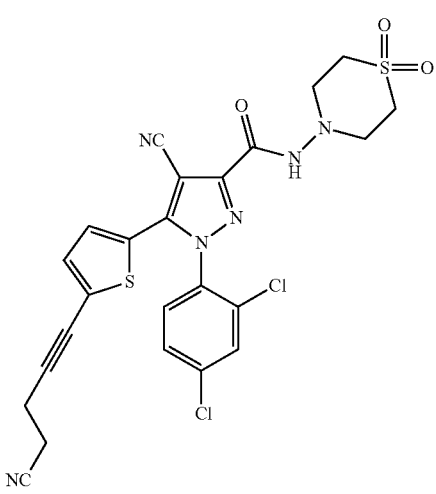 [SMILES: N#CCCC#Cc1ccc(-c2c(C#N)c(C(=O)NN3CCS(=O)(=O)CC3)nn2-c2ccc(Cl)cc2Cl)s1]
42
TABLE 1-continued
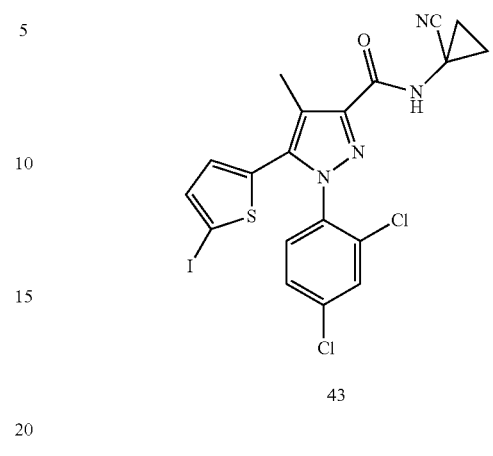
43
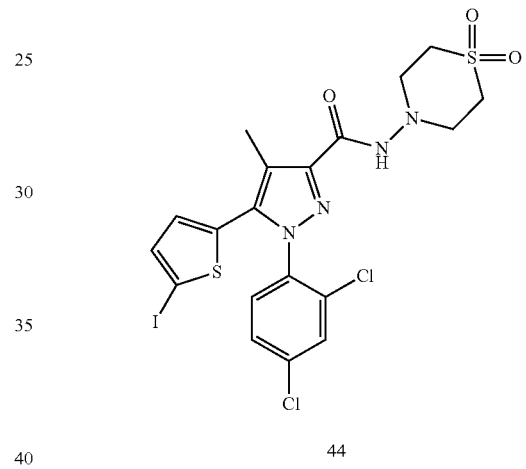
44
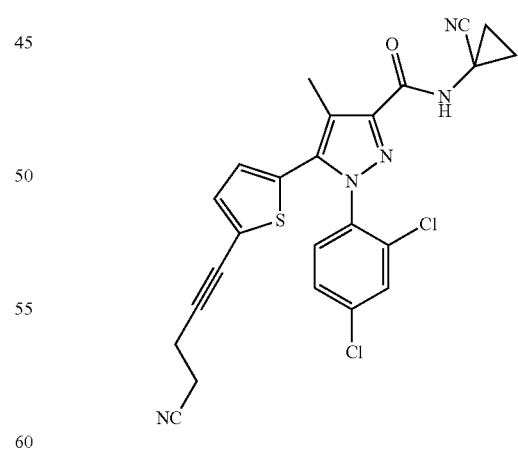
45
The invention will be further described in more detail by the following synthetic examples. These examples are offered to illustrate the invention, and are not to be construed in any way as limiting the scope of the invention.

Compound Synthesis and Formulation

Example 1

1-(4-(4-cyanobut-1-ynyl)phenyl)-2-(2,4-dichlorophenyl)-N-morpholino-5-(pyrrolidin-1-ylmethyl)-1H-imidazole-4-carboxamide (compound 12)

Step A

N-(4-bromophenyl)-2,4-dichlorobenzimidamide

To a magnetically stirred solution of EtMgBr (3.3 mL, 3M in diethyl ether, 10 mmol) in THF (30 mL) 4-bromoaniline (1.72 g, 10 mmol) was slowly added portion wise. After the solution was stirred for 30 min., 2,4-dichlorobenzonitrile (1.72 g, 10 mmol) was added. The resulting solution was stirred at room temperature (RT) overnight. The reaction mixture was quenched with water and extracted with ethyl acetate. The combined extracts were dried over anhydrous $MgSO_4$, filtered and evaporated under reduced pressure to give the benzimidamide as an off-white solid (2.45 g, 71.2%).

Step B

Ethyl 1-(4-bromophenyl)-2-(2,4-dichlorophenyl)-5-methyl-1H-imidazole-4-carboxylate To a magnetically stirred solution of above imidamide from step A (2.45 g, 7 mmol) in 30 mL anhydrous toluene were added ethyl 3-bromo-2-oxobutanoate (1.48 g, 7 mmol) and $Na_2CO_3$ (0.74 g, 7 mmol). The contents were stirred at 100° C. for 12 hours. The reaction was brought to RT. The reaction mixture was quenched with water and extracted with ethyl acetate. The combined extracts were dried over anhydrous $MgSO_4$, filtered and evaporated under reduced pressure. Purification by column chromatography gave the ester as pale white solid (1.5 g, 46.4%).

Step C 2-(2,4-dichlorophenyl)-1-(4-iodophenyl)-N-morpholino-5-(pyrrolidin-1-ylmethyl)-1H-imidazole-4-carboxamide (compound 8)

To a magnetically stirred solution of ester from step B (1.5 g, 3.3 mmol) in carbon tetrachloride (20 mL) N-bromosuccinimide (0.58 g, 3.3 mmol) was added along with a catalytic amount of and 2,2'-azobisisobutyronitrile (AIBN, 15 mg). The resulting mixture was refluxed for 3 h. After cooling to RT, the precipitate was filtered. The filtrate was washed with 2×50 ml water and the organic layer was dried over anhydrous sodium sulfate, filtered, and evaporated. Flash column chromatography on silica gel with petroleum ether/ethyl acetate (1:9) gave bromo derivative (1 mg, 56% yield) as a pale yellow solid. The bromo derivative (1 g, 1.88 mmol) was taken in acetonitrile (50 ml) and to that Hunnig's base (0.26 g, 2 mmol) and pyrrolidine (0.14 g, 2 mmol) were added. The reaction mixture was heated at 60-65° C. for 1 h hour. After cooling the reaction mixture was concentrated to give an oily residue which was subsequently dissolved in dichloromethane (50 ml). This was washed with 2×25 ml water and the organic layer was dried over anhydrous sodium sulfate, filtered, and evaporated. Flash column chromatography on silica gel with petroleum ether/ethyl acetate (1:1) gave ester (700 mg, 71.2%) as a white solid. To the suspension of $AlCl_3$ (0.53 g, 4 mmol) in dichloroethane (20 mL) was added 4-aminomorpholine (0.41 g, 4 mmol) at 0° C. and stirred for 25 min at that temperature. To this was added a solution of ester from step C (700 mg, 1.3 mmol) in dichloroethane (5 mL). The reaction was brought to RT and stirred at that temperature for 8 h. The reaction was quenched with dilute HCl and the organic layer was extracted with dichloromethane. The combined extracts were dried over anhydrous $MgSO_4$, filtered and evaporated under reduced pressure. Purification by column chromatography gave the amide as an off-white solid (500 mg, 60%).

$^1$H NMR (500 MHz, $CDCl_3$-d) 8.39 (s, 1H), 7.65 (d, J=8.30 Hz, 2H), 7.34 (s, 1H), 7.27-7.32 (m, 1H), 7.22-7.26 (m, 1H), 7.05 (d, J=8.30 Hz, 2H), 3.87 (t, J=4.39 Hz, 4H), 3.83 (s, 2H), 2.94 (br. s., 4H), 2.50 (br. s., 4H), 1.69 (br. s., 4H)

Step D

The amide from step C (500 mg, 0.79 mmol) was taken and subjected to the Sonogashira reaction as was performed in example 3F to give compound 12 (200 mg, 47.5%).

$^1$H NMR (500 MHz, $CDCl_3$-d) 8.19-8.52 (m, 1H), 7.47 (d, J=7.81 Hz, 3H), 7.35 (d, J=1.95 Hz, 3H), 7.29-7.30 (m, 1H), 7.25-7.28 (m, 1H), 4.04-4.92 (m, 2H), 3.90 (t, J=4.39 Hz, 4H), 2.98 (br. s., 4H), 2.73-2.88 (m, 2H), 2.63-2.74 (m, 2H), 2.02 (br. s., 4H), 1.74 (none, 4H)

Example 2

4-(4-(1-(2,4-dichlorophenyl)-4-methyl-3-(piperidin-1-ylcarbamoyl)-1H-pyrazol-5-yl)phenyl)but-3-ynyl nitrate (compound 10)

To a stirred solution of compound 5 [1-(2,4-dichlorophenyl)-5-(4-(4-iodobut-1-ynyl)phenyl)-4-methyl-N-(piperidin-1-yl)-1H-pyrazole-3-carboxamide] (60 mg, 0.9 mmol) taken in acetonitrile (20 ml) and to that silver nitrate (33.5 mg, 0.19 mmol) was added. The reaction mixture was heated for 2 hours. After cooling to RT, the precipitate was filtered. The filtrate was concentrated to give an oily residue which was subsequently dissolved in dichloromethane (20 ml). This was washed with 2×5 ml water and the organic layer was dried over anhydrous sodium sulfate, filtered, and evaporated. Flash column chromatography on silica gel with petroleum ether/ethyl acetate (1:1) gave compound 2 (40 mg, 74.6% yield) as a white solid.

$^1$H NMR (500 MHz, $CDCl_3$-d) 7.65 (s, 1H), 7.43 (s, 1H), 7.36 (d, J=8.30 Hz, 2H), 7.29-7.33 (m, 2H), 7.07 (d, J=8.30 Hz, 2H), 4.64 (t, J=6.84 Hz, 2H), 2.74-3.02 (m, 6H), 2.39 (s, 3H), 1.69-1.90 (m, 4H), 1.45 (br. s., 2H)

Example 3

5-(4-(4-cyanobut-1-ynyl)phenyl)-1-(2,4-dichlorophenyl)-4-methyl-N-(1,1-dioxothiomorpholino)-1H-pyrazole-3-carboxamide (compound 15)

Step A

4'-iodopropiophenone

Iodobenzene (100 g, 0.49 mol) was taken in a dry 1 L 3 neck flask equipped with a $N_2$ inlet and to it 200 ml of $CS_2$ was added. The contents were cooled to 0-5° C. and then $AlCl_3$ (80 g, 0.6 moles) and subsequently propionyl chloride (60 g, 0.64 mol) were added while keeping the temperature (internal) at 5-10° C. The contents were stirred for 24 hrs. The reaction mixture was poured into a 5 liter plastic beaker containing 1

L of 10% HCl+1 Kg of crushed ice. The resultant slurry was extracted with 1 L of ethyl acetate. The organic layer was separated and washed with 2×500 ml of water and 500 ml of brine. The organic layer was dried over sodium sulphate and concentrated at 40° C. to give 4'-iodopropiophenone (48 g, 38%).

$^1$H NMR (500 MHz, CDCl$_3$-d) 7.82 (d, 2H), 7.67 (d, J=8.30 Hz, 2H), 2.96 (q, J=7.00 Hz, 2H), 1.22 (t, J=7.32 Hz, 3H)

Step B

Lithium-4-ethoxy-1-(4-iodophenyl)-2-methyl-3,4-dioxobut-1-en-1-olate

4'-iodopropiophenone obtained from step A was taken in a 2 L 3 neck flask equipped with a nitrogen inlet. To that 500 ml of diethyl ether was added and the contents were cooled at −78° C. using a dry-ice acetone bath. The reaction mixture was stirred for 15 minutes. Subsequently, a 1 M solution of lithium bis(trimethylsilyl)amide in hexanes (222 ml, 0.22 mol) was added drop wise over 1 hour. The contents were stirred at −78° C. an additional 1 hour after diethyl oxalate which (32.3 g, 0.22 mol) taken in diethyl ether was added over 30 minutes. The contents were stirred for 2 hours at −78° C. after which the cooling bath was removed. The contents were brought to room temperature over 10 hours. The solids were filtered under a stream of nitrogen and then washed with 200 ml of ether. The solid obtained was air dried for 1 hour and was taken as such to the next reaction directly (52 g, 76.9%).

Step C ethyl 1-(2,4-dichlorophenyl)-5-(4-iodophenyl)-4-methyl-1H-pyrazole-3-carboxylate The lithium salt obtained from step B was taken in a 1 liter 1 neck flask and to that 2,4-dichlorophenylhydrzine hydrochloride (30.3 g, 0.14 mol) and 1.5 liters of anhydrous ethanol were added in on portion. The resulting mixture was stirred at room temperature for 24 hours. The solids were filtered, washed with ethanol and then dried under vacuum to give a light yellow of ethyl 2-(2-(2,4-dichlorophenyl)hydrazono)-4-(4-iodophenyl)-3-methyl-4-oxobutanoate (27 g). The solids were taken in a 1 L 1 neck flask and to that 1 liter of glacial acetic acid was added. The mixture was refluxed for 4 hours. Acetic acid was distilled out completely and to the residue 500 ml of ethyl acetate was added. The organic layer was separated, washed with 1 liter of water, dried over sodium sulphate and concentrated to give the crude ester. The ester was purified by column chromatography using a 10% ethyl acetate-hexane mixture to give the pure ester (15 g, 57.6%).

$^1$H NMR (500 MHz, CDCl$_3$-d) 7.69 (d, J=8.30 Hz, 2H), 7.41 (s, 1H), 7.29-7.39 (m, 2H), 6.89 (d, J=8.30 Hz, 2H), 4.48 (q, J=7.32 Hz, 2H), 2.35 (s, 3H), 1.37-1.53 (m, 3H)

Step D 1-(2,4-dichlorophenyl)-5-(4-iodophenyl)-4-methyl-1H-pyrazole-3-carboxylic acid The ester (10 g, 19.9 mmoles) obtained from step C was taken in 500 ml 1 neck flask and to it 300 ml of 7:2:1 mixture of THF-methanol-water along with solid lithium hydroxide (2.5 g, 104.6 mol) was added. The mixture was refluxed for 12 hours. The solvents were removed totally and to the residue 200 ml of DCM was added. To that 100 ml of water was added and the mixture was acidified to pH ~2 using concentrated HCl. The organic layer was separated, washed with 100 ml of brine, dried over sodium sulphate and concentrated to give the acid. This was taken directly to the next step (9.4 g, 100%).

$^1$H NMR (500 MHz, CDCl$_3$-d) 7.70 (d, J=8.30 Hz, 2H), 7.44 (s, 1H), 7.30-7.38 (m, 2H), 6.90 (d, J=8.30 Hz, 2H), 2.37 (s, 3H)

Step E 1-(2,4-dichlorophenyl)-4-methyl-5-(4-iodophenyl)-N-(1,1-dioxothiomorpholino)-1H-pyrazole-3-carboxamide (compound 16)

The acid (7.5 g, 15.8 mmol) obtained from step D was taken in a 500 ml 1 neck flask equipped with a nitrogen inlet and to it 200 ml of DCM, 4-aminothiomorpholine-1,1-dioxide (2.61 g, 17.4 mmol), TBTU (5.59 g, 17.4 mmol) and DIPEA (2.25 g, 17.4 mmol) were added and the contents were stirred for 1 hour. To the reaction mixture, 100 ml of water was added and the contents were acidified to pH ~2 using concentrated HCl. The organic layer was separated, washed with brine, dried over sodium sulphate and concentrated to give the amide (3 g, 31.2%).

$^1$H NMR (500 MHz, CDCl$_3$-d) 8.07 (s, 1H), 7.67 (d, J=8.30 Hz, 2H), 7.45 (d, J=1.95 Hz, 1H), 7.29-7.34 (m, 1H), 7.25 (s, 1H), 6.85 (d, J=8.30 Hz, 2H), 3.44-3.66 (m, 4H), 3.26 (d, J=4.88 Hz, 4H), 2.35 (s, 3H)

Step F

To a stirred solution of amide obtained from step E (2 g, 3.3 mmol) in pyrrolidine (40 ml), under an argon atmosphere, tetrakis(triphenylphosphine)palladium(0) (0.4 g, 0.3 mmol) was added. The reaction mixture was stirred for 5 min at room temperature, and subsequently 4-cyano-1-butyne (0.78 g, 9.9 mmol) in pyrrolidine (1.5 ml) was added over 5 minutes. The resulting mixture was heated at 80-85° C. for 10 h. The reaction was hydrolyzed with a saturated aqueous solution of ammonium chloride and extracted with ethyl acetate. The organic extract was dried over MgSO4 and the solvent was removed in vacuo. Purification by flash column chromatography on silica gel (eluant ethylacetate) gave compound 15 as a white solid (0.8 g, 43.7%)

$^1$H NMR (500 MHz, CDCl$_3$-d) 8.08 (s, 1H), 7.43 (s, 1H), 7.37 (d, J=7.81 Hz, 2H), 7.28-7.34 (m, 1H), 7.24 (s, 1H), 7.06 (d, J=7.81 Hz, 2H), 3.56 (d, J=4.88 Hz, 4H), 3.26 (br. s., 4H), 2.72-2.87 (m, 2H), 2.57-2.71 (m, 2H), 2.37 (s, 3H)

Example 4

5-(5-(4-cyanobut-1-ynyl)thiophen-2-yl)-1-(2,4-dichlorophenyl)-4-methyl-N-(piperidin-1-yl)-1H-pyrazole-3-carboxamide (compound 34)

Step A

N-Methoxy-N-methylpropionamide

Pyridine (17 mL, 0.4 mol) at 0° C. was added dropwise to a solution of O,N-dimethyl-hydroxylamine hydrochloride (10 g, 0.1 mol) and propionyl chloride (10 g, 0.1 mol) in anhydrous dichloromethane (250 mL). The solution was stirred at room temperature for 24 h, washed with 2×50 ml of 5% hydrochloric acid, 100 ml of saturated NaHCO$_3$ and 100 ml brine, dried over MgSO₄ and concentrated under reduced pressure to give colorless oil (10 g, 89%).

Step B 1-(5-iodothiophen-2-yl)propan-1-one 38.4 ml of a 2M solution of lithium diisopropylamide (8.2 g, 76.8 mmol) in THF-heptane-ethylbenzene was added to THF (50 ml) taken in a 500 three neck RB flask equipped with a nitrogen inlet. The mixture was cooled to −40° C. and then 2-iodothiophene (16.1 g, 76.8 mmol) taken in 50 ml of THF was added with vigorous stirring. After 10 minutes the mixture was warmed to −10° C. and stirred for 30 min. The reaction mixture was re-cooled to −40° C. and N-methoxy-N-methylpropionamide (9 g, 76.8 mmol) taken in 50 ml of THF was added in one portion. The reaction mixture was allowed to warm slowly to 0° C. and then the reaction was quenched with saturated 50 ml of NH₄Cl solution. The contents were extracted with 3×100 ml of DCM, dried over MgSO₄ and concentrated to give an oily residue. This was purified by flash chromatography to give the title compound (10 g, 49%).

¹H NMR (500 MHz, CDCl₃-d) 7.32 (d, 1H), 7.27-7.30 (m, 1H), 2.86 (q, J=7.32 Hz, 2H), 1.21 (t, J=7.32 Hz, 3H)

Step C ethyl 1-(2,4-dichlorophenyl)-5-(5-iodothiophen-2-yl)-4-methyl-1H-pyrazole-3-carboxylate The title compound was obtained as in example 3

¹H NMR (500 MHz, CDCl₃-d) 7.46 (d, J=1.95 Hz, 1H), 7.35-7.39 (m, 1H), 7.34 (d, 1H), 7.14 (d, J=3.91 Hz, 1H), 6.55 (d, J=3.91 Hz, 1H), 4.45 (q, J=6.84 Hz, 2H), 2.42 (s, 3H), 1.42 (t, J=7.08 Hz, 3H)

Step D 1-(2,4-dichlorophenyl)-5-(5-iodothiophen-2-yl)-4-methyl-N-(piperidin-1-yl)-1H-pyrazole-3-carboxamide The title compound was obtained as in example 3

Step E

The title compound was obtained as in example 3

¹H NMR (500 MHz, CDCl₃-d) 7.60 (br. s., 1H), 7.50 (d, J=1.95 Hz, 1H), 7.35-7.39 (m, 1H), 7.31-7.35 (m, 1H), 7.05 (d, J=3.91 Hz, 1H), 6.72 (d, J=3.42 Hz, 1H), 2.85 (br. s., 4H), 2.80 (t, J=7.08 Hz, 2H), 2.56-2.70 (m, 2H), 2.47 (s, 3H), 1.75 (quin, J=5.62 Hz, 4H), 1.43 (br. s., 2H)

Example 5

1-(2,4-dichlorophenyl)-5-(5-iodothiophen-2-yl)-4-methyl-N-(1,1-dioxothiomorpholino)-1H-pyrazole-3-carboxamide (compound 44)

¹H NMR (500 MHz, CDCl₃-d) 8.10 (s, 1H), 7.54 (d, J=1.95 Hz, 1H), 7.36-7.42 (m, 1H), 7.33 (d, 1H), 7.17 (d, J=3.91 Hz, 1H), 6.57 (d, J=3.91 Hz, 1H), 3.57 (br. s., 4H), 3.28 (br. s., 4H), 2.47 (s, 3H)

Example 6

N-(1-cyanocyclopropyl)-1-(2,4-dichlorophenyl)-5-(5-iodothiophen-2-yl)-4-methyl-1H-pyrazole-3-carboxamide (compound 43)

¹H NMR (500 MHz, CDCl₃-d) 7.53 (s, 1H), 7.41 (none, 1H), 7.30-7.34 (m, 1H), 7.17 (d, J=3.91 Hz, 1H), 6.57 (d, J=3.91 Hz, 1H), 2.46-2.57 (m, 3H), 1.63 (br. s., 2H), 1.35-1.42 (m, 2H)

Example 7

5-(4-(4-cyanobut-1-ynyl)phenyl)-1-(2,4-dichlorophenyl)-4-(hydroxymethyl)-N-morpholino-1H-pyrazole-3-carboxamide (compound 2)

¹H NMR (500 MHz, CDCl₃-d) 7.84 (s, 1H), 7.45 (d, J=2.44 Hz, 1H), 7.37 (d, J=8.30 Hz, 2H), 7.29-7.33 (m, 1H), 7.25 (s, 1H), 7.07 (d, J=8.30 Hz, 2H), 5.01 (t, J=7.08 Hz, 1H), 4.63 (d, J=7.32 Hz, 2H), 3.89 (t, J=4.64 Hz, 4H), 2.96 (d, J=4.39 Hz, 4H), 2.72-2.84 (m, 2H), 2.56-2.69 (m, 2H)

Example 8

4-(4-(1-(2,4-dichlorophenyl)-4-methyl-3-(piperidin-1-ylcarbamoyl)-1H-pyrazol-5-yl)phenyl)but-3-ynyl methanesulfonate (compound 9)

¹H NMR (500 MHz, CDCl₃-d) 7.67 (br. s., 1H), 7.43 (s, 1H), 7.35 (d, J=7.81 Hz, 2H), 7.29-7.33 (m, 2H), 7.07 (d, J=8.30 Hz, 2H), 4.39 (t, J=6.59 Hz, 2H), 3.08 (s, 3H), 2.77-2.96 (m, 6H), 2.39 (s, 3H), 1.77 (br. s., 4H), 1.45 (br. s., 2H)

Example 9

S-4-(4-(1-(2,4-dichlorophenyl)-4-methyl-3-(piperidin-1-ylcarbamoyl)-1H-pyrazol-5-yl)phenyl)but-3-ynyl ethanethioate (compound 5)

¹H NMR (500 MHz, CDCl₃-d) 7.62 (s, 1H), 7.41 (s, 1H), 7.33 (d, J=8.30 Hz, 2H), 7.27-7.30 (m, 2H), 7.04 (d, J=8.30 Hz, 2H), 3.10 (t, J=7.08 Hz, 2H), 2.87 (br. s., 4H), 2.69 (t, J=7.08 Hz, 2H), 2.36 (d, J=8.79 Hz, 6H), 1.75 (quin, J=5.62 Hz, 4H), 1.43 (br. s., 2H)

Example 10

1-(2,4-dichlorophenyl)-5-(4-(4-iodobut-1-ynyl)phenyl)-4-methyl-N-(piperidin-1-yl)-1H-pyrazole-3-carboxamide (compound 6)

¹H NMR (500 MHz, CDCl₃-d) 7.63 (s, 1H), 7.41 (s, 1H), 7.36 (d, J=8.30 Hz, 2H), 7.27-7.31 (m, 2H), 7.05 (d, J=8.30 Hz, 2H), 3.30 (t, J=7.32 Hz, 2H), 3.00 (t, J=7.32 Hz, 2H), 2.86 (br. s., 4H), 2.37 (s, 3H), 1.67-1.84 (m, 4H), 1.43 (br. s., 2H)

Example 11

5-(4-(but-3-en-1-ynyl)phenyl)-1-(2,4-dichlorophenyl)-4-methyl-N-(piperidin-1-yl)-1H-pyrazole-3-carboxamide (compound 13)

¹H NMR (500 MHz, CDCl₃-d) 7.63 (s, 1H), 7.41 (s, 1H), 7.37 (d, J=7.81 Hz, 2H), 7.27 (br. s., 2H), 7.06 (d, J=7.81 Hz,

2H), 6.00 (dd, J=11.23, 17.58 Hz, 1H), 5.49-5.81 (m, 2H), 2.87 (br. s., 4H), 2.38 (s, 3H), 1.64-1.89 (m, 4H), 1.43 (br. s., 2H)

Example 12

5-(4-(4-azidobut-1-ynyl)phenyl)-1-(2,4-dichlorophenyl)-4-methyl-N-(piperidin-1-yl)-1H-pyrazole-3-carboxamide (compound 14)

$^1$H NMR (500 MHz, CDCl$_3$-d) 7.62 (s, 1H), 7.41 (s, 1H), 7.35 (d, J=7.81 Hz, 2H), 7.27-7.29 (m, 2H), 7.04 (d, J=8.30 Hz, 2H), 3.46 (t, J=6.59 Hz, 2H), 2.87 (br. s., 4H), 2.71 (t, J=6.59 Hz, 2H), 2.37 (s, 3H), 1.64-1.86 (m, 4H), 1.43 (br. s., 2H)

Example 13

1-(2,4-dichlorophenyl)-5-(4-(4-isothiocyanatobut-1-ynyl)phenyl)-4-methyl-N-(piperidin-1-yl)-1H-pyrazole-3-carboxamide (compound 11)

$^1$H NMR (500 MHz, CDCl$_3$-d) 7.63 (br. s., 1H), 7.42 (s, 1H), 7.38 (d, J=8.30 Hz, 2H), 7.27-7.30 (m, 2H), 7.06 (d, J=8.30 Hz, 2H), 3.70 (t, J=6.59 Hz, 2H), 2.87 (br. s., 4H), 2.82 (t, J=6.59 Hz, 2H), 2.38 (s, 3H), 1.70-1.83 (m, 4H), 1.43 (br. s., 2H)

Example 14

5-(4-(4-cyanobut-1-ynyl)phenyl)-1-(2,4-dichlorophenyl)-4-ethyl-N-(piperidin-1-yl)-1H-pyrazole-3-carboxamide (compound 22)

$^1$H NMR (500 MHz, CDCl$_3$-d) 7.65 (s, 1H), 7.41 (s, 1H), 7.35 (d, J=8.30 Hz, 2H), 7.28-7.30 (m, 1H), 7.27 (s, 1H), 7.07 (d, J=7.81 Hz, 2H), 2.87 (br. s., 4H), 2.70-2.82 (m, 4H), 2.54-2.69 (m, 2H), 1.76 (quin, J=5.62 Hz, 4H), 1.43 (br. s., 2H), 1.21 (t, J=7.32 Hz, 3H)

Example 15

5-(4-(4-cyanobut-1-ynyl)phenyl)-1-(2,4-dichlorophenyl)-4-ethyl-N-morpholino-1H-pyrazole-3-carboxamide (compound 25)

$^1$H NMR (500 MHz, CDCl$_3$-d) 7.71 (s, 1H), 7.42 (s, 1H), 7.36 (d, J=8.30 Hz, 2H), 7.30 (none, 1H), 7.26 (s, 1H), 7.08 (d, J=8.30 Hz, 2H), 3.78-3.93 (m, 4H), 2.95 (br. s., 4H), 2.73-2.85 (m, 4H), 2.59-2.69 (m, 2H), 1.21 (t, J=7.32 Hz, 3H)

Example 16

3-((4-(1-(2,4-dichlorophenyl)-4-methyl-3-(piperidin-1-ylcarbamoyl)-1H-pyrazol-5-yl)phenyl)ethynyl)pyridine 1-oxide (compound 23)

$^1$H NMR (500 MHz, CDCl$_3$-d) 8.31 (s, 1H), 8.17 (d, J=6.84 Hz, 1H), 7.64 (s, 1H), 7.48 (d, J=8.30 Hz, 2H), 7.43 (s, 1H), 7.36 (d, J=8.30 Hz, 1H), 7.31 (s, 2H), 7.28 (s, 1H), 7.14 (d, J=8.30 Hz, 2H), 2.87 (br. s., 4H), 2.40 (s, 3H), 1.76 (quin, J=5.62 Hz, 4H), 1.44 (br. s., 2H)

Example 17

1-(2,4-dichlorophenyl)-4-ethyl-N-morpholino-5-phenyl-1H-pyrazole-3-carboxamide (compound 20)

$^1$H NMR (500 MHz, CDCl$_3$-d) 7.72 (s, 1H), 7.41 (s, 1H), 7.28-7.37 (m, 3H), 7.27 (s, 2H), 7.08-7.19 (m, 2H), 3.63-4.07 (m, 4H), 2.86-3.15 (m, 4H), 2.78 (q, J=7.32 Hz, 2H), 1.22 (t, J=7.32 Hz, 3H)

Example 18

5-(4-(4-cyanobut-1-ynyl)phenyl)-1-(2,4-dichlorophenyl)-4-ethyl-N-(1,1-dioxothiomorpholino)-1H-pyrazole-3-carboxamide (compound 24)

$^1$H NMR (500 MHz, CDCl$_3$-d) 8.10 (s, 1H), 7.43 (d, J=1.95 Hz, 1H), 7.37 (d, J=8.30 Hz, 2H), 7.28-7.32 (m, 1H), 7.24 (s, 1H), 7.07 (d, J=8.30 Hz, 2H), 3.47-3.63 (m, 4H), 3.27 (d, J=4.88 Hz, 4H), 2.71-2.84 (m, 4H), 2.59-2.69 (m, 2H), 1.61 (s, 3H), 1.21 (t, J=7.32 Hz, 3H)

Example 19

4-cyano-5-(4-(4-cyanobut-1-ynyl)phenyl)-1-(2,4-dichlorophenyl)-N-(piperidin-1-yl)-1H-pyrazole-3-carboxamide (compound 28)

$^1$H NMR (500 MHz, CDCl$_3$-d) 7.54 (br. s., 1H), 7.49 (d, J=1.95 Hz, 1H), 7.32-7.44 (m, 4H), 7.25 (d, 2H), 2.91 (br. s., 4H), 2.73-2.85 (m, 2H), 2.59-2.72 (m, 2H), 1.67-1.87 (m, 4H), 1.44 (br. s., 2H)

Example 20

4-cyano-5-(4-(4-cyanobut-1-ynyl)phenyl)-1-(2,4-dichlorophenyl)-N-morpholino-1H-pyrazole-3-carboxamide (compound 29)

$^1$H NMR (500 MHz, CDCl$_3$-d) 7.61 (s, 1H), 7.50 (s, 1H), 7.35-7.47 (m, 4H), 7.27 (d, 2H), 3.74-3.93 (m, 4H), 2.91-3.07 (m, 4H), 2.73-2.87 (m, 2H), 2.58-2.71 (m, 2H)

Example 21

5-(4-(4-cyanobut-1-ynyl)phenyl)-1-(2,4-dichlorophenyl)-4-cyano-N-(1,1-dioxothiomorpholino)-1H-pyrazole-3-carboxamide (compound 32)

$^1$H NMR (500 MHz, CDCl$_3$-d) 7.98 (s, 1H), 7.51 (d, J=1.95 Hz, 1H), 7.38-7.45 (m, 3H), 7.33-7.38 (m, 1H), 7.25 (d, 2H), 3.50-3.68 (m, 4H), 3.17-3.34 (m, 4H), 2.72-2.90 (m, 2H), 2.55-2.70 (m, 2H)

Forskolin-Stimulated cAMP Assay

Intracellular cAMP levels were measured with a competitive protein-binding assay using intact HEK293 cells expressing hCB1 or hCB2 and a cAMP immunoassay kit from Sigma (St. Louis, Mo.). In short, forskolin stimulated cells were incubated with various concentrations of compound, cAMP anti-body and cAMP conjugate for 2 hours at ambient temperature. The reaction was stopped by emptying the wells followed by the addition of p-NPP substrate and incubation for 1 hour. This reaction was stopped and absorbance intensity, detected at 405 nm, was inversely proportional to the concentration of cAMP produced by the cells. The results were expressed as percent inhibition of forskolin-stimulated cAMP accumulation and EC50 curves were generated with the use of GraphPad Prism software.

Figure 1A:
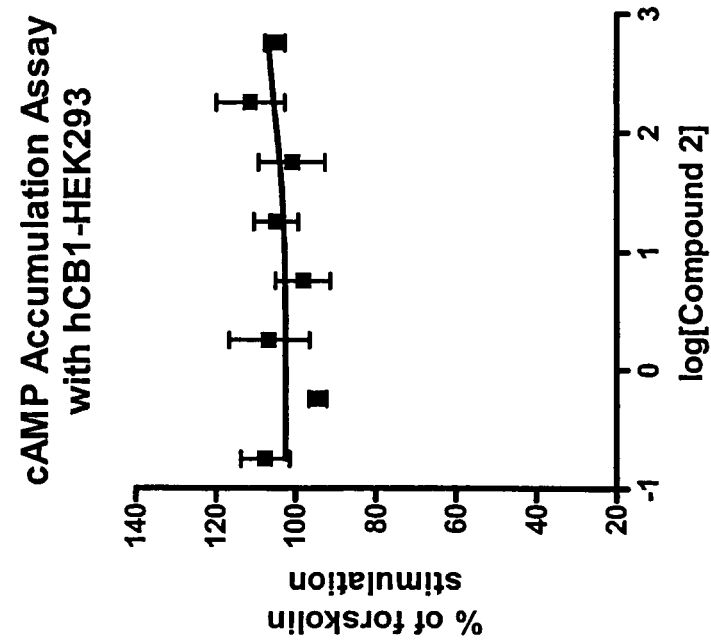
Figure 2A:
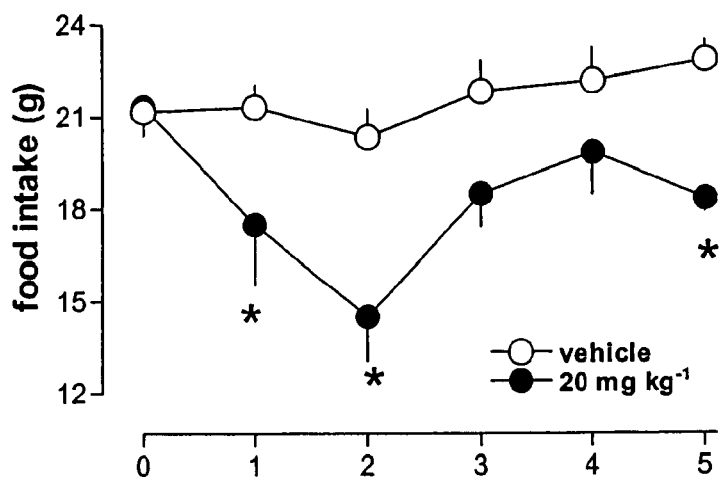
FIGS. 2A-2C are graphs showing food intake, weigh change and body weight following administration of Compound 15 to rats.
Figure 2B:
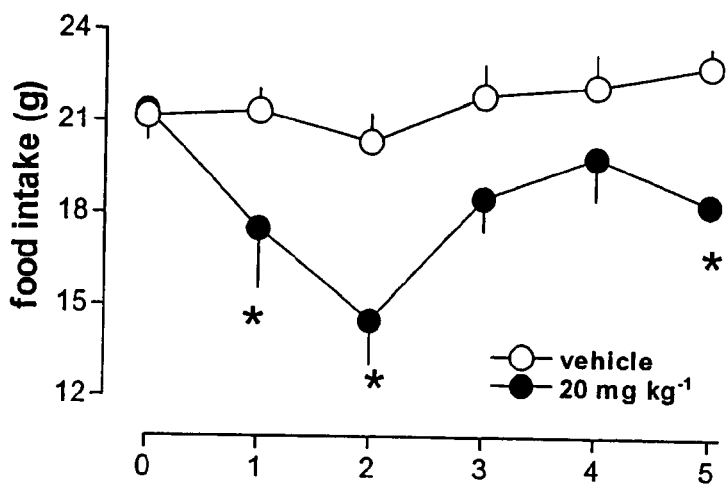
Figure 2C:
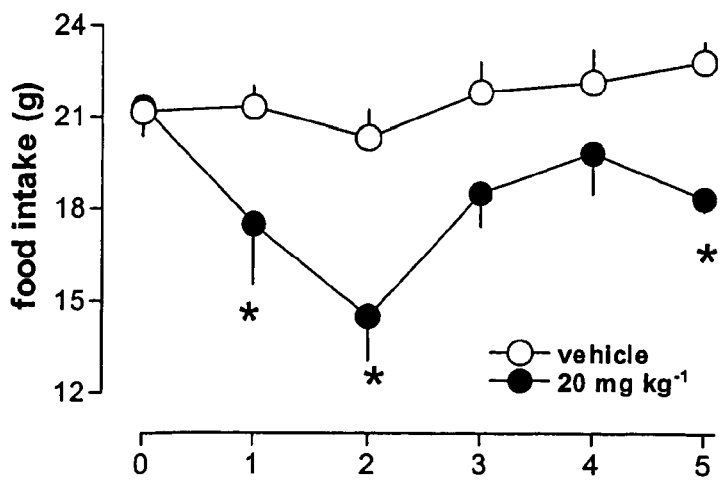

For example compound 2 and compound 15 did not change the forskolin-stimulated cAMP accumulation in CB1 transfected HEK cells (FIGS. 1A and 1B) and are therefore considered to be a CB1 neutral antagonists.

The results are from one assay done in triplicate.

Reference herein to a "standard forskolin-stimulated cAMP assay" or like phrase refers to the foregoing assay method.

[$^3$H]CP55,940 Competitive Binding Assay

Some of the inventive analogs were tested for CB1 receptor binding affinity and for CB2 receptor affinity (to determine selectivity). As used herein, "binding affinity" is represented by the $K_i$ value which is the inhibition constant correlated with the concentration of an analog required to occupy the 50% of the total number (Bmax) of the receptors. The lower the $K_i$ value the higher the binding affinity. As used herein an analog is said to have "binding selectivity" if it has higher binding affinity for one receptor compared to the other receptor; e.g. a cannabinoid analog which has a $K_i$ of 0.1 nM for CB1 and 10 nM for CB2, is 100 times more selective for the CB1 receptor.

For the CB1 receptor binding studies, membranes were prepared from rat forebrain membranes according to the procedure of P. R. Dodd et al, *A Rapid Method for Preparing Synaptosomes: Comparison with Alternative Procedures*, Brain Res., 107-118 (1981). The binding of the novel analogues to the CB1 cannabinoid receptor was assessed as described in W. A. Devane et al, *Determination and Characterization of a Cannabinoid Receptor in a Rat Brain*, Mol. Pharmacol., 34, 605-613 (1988) and A. Charalambous et al, *5'-azido Δ$^8$-THC: A Novel Photoaffinity Label for the Cannabinoid Receptor*, J. Med. Chem., 35, 3076-3079 (1992) with the following changes. The above articles are incorporated by reference herein.

Membranes, previously frozen at −80° C., were thawed on ice. To the stirred suspension was added three volumes of TME (25 mM Tris-HCl buffer, 5 mM MgCl$_2$ and 1 mM EDTA) at a pH 7.4. The suspension was incubated at 4° C. for 30 min. At the end of the incubation, the membranes were pelleted and washed three times with TME.

The treated membranes were subsequently used in the binding assay described below. Approximately 30 μg of membranes were incubated in silanized 96-well microtiter plate with TME containing 0.1% essentially fatty acid-free bovine serum albumin (BSA), 0.8 nM [$^3$H]CP-55,940, and various concentrations of test materials in a final volume of 200 μL. The assays were incubated for 1 hour at 30° C. and then immediately filtered using Packard Filtermate 196 harvester and Whatman GF/C filterplates and washed with wash buffer (TME) containing 0.5% BSA. Radioactivity was detected using MicroScint 20 scintillation cocktail added directly to the dried filterplates, and the filterplates were counted using a Packard Instruments Top-Count. Nonspecific binding was assessed using 100 nM CP-55,940. Data collected from three independent experiments performed with duplicate determinations was normalized between 100% and 0% specific binding for [$^3$H]CP-55,940, determined using buffer and 100 nM CP-55,940. The normalized data was analyzed using a 4-parameter nonlinear logistic equation to yield IC$_{50}$ values. Data from at least two independent experiments performed in duplicate was used to calculate IC$_{50}$ values which were converted to K$_i$ values using the assumptions of Cheng et al, *Relationship Between the Inhibition Constant ($K_i$) and the concentration of Inhibitor which causes 50% Inhibition (IC$_{50}$) of an Enzymatic Reaction, Biochem. Pharmacol.*, 22, 3099-3102, (1973), which is incorporated by reference herein.

For the CB2 receptor binding studies, membranes were prepared from frozen mouse spleen essentially according to the procedure of P. R. Dodd et al, *A Rapid Method for Preparing Synaptosomes: Comparison with Alternative Procedures*, Brain Res., 226, 107-118 (1981) which is incorporated by reference herein. Silanized centrifuge tubes were used throughout to minimize receptor loss due to adsorption. The CB2 binding assay was conducted in the same manner as for the CB1 binding assay. The binding affinities ($K_i$) were also expressed in nanomoles (nM).

The CB1 cannabinoid receptor binding affinities ($K_i$) for some of the compounds disclosed in the invention range between 0.5 nM and less than 100 nM. The CB2 cannabinoid receptor binding affinities ($K_i$) for the synthesized analogs range between 60 nM and 5000 nM. For example, CB1 cannabinoid receptor binding affinity ($K_i$) for compound 2 is 7 nM and the CB2 cannabinoid receptor binding affinity ($K_i$) is 1672 nM. The CB1 selectivity for some of the compounds range from 5 to greater than 5000.

Distribution and the Blood Brain Barrier:

Mice (CD-1, weighing 25-30 g) are dosed intravenously or by oral gavage with 0.1-2 mg/kg of the compound dissolved in appropriate vehicle. Fifteen minutes post-injection or 30 and 60 minutes post-gavage, the animals are sacrificed humanely by decapitation followed by blood collection (~500 μL) and tissue dissection; samples are flash frozen with liquid nitrogen to prevent post-mortem degradation of the compounds or endogenous ligands. Tissues (plasma or brain) are extracted and analyzed using a Thermo-Finnigan Quantum Ultra triple quadrupole mass spectrometer with an Agilent 1100 HPLC front-end. Chromatographic separation is achieved using a Phenomenex Gemini column (2×50 mm, 5μ). Hardware consists of a Finnigan TSQ Quantum Ultra triple quad mass spectrometer with both an APCI and ESI source and an Agilent 1100 front end. The mass spectrometer with mobile phase consisting of 0.1% formic acid in water (A) and 0.1% formic acid in methanol (B). SR141716 gets into the brain better at 1.8%/g (% of the total dose per gram brain) at 15 minutes post IV as compared to compound 2 which is 0.6%.

Those skilled in the art will recognize, or be able to ascertain using no more than routine experimentation, many equivalents to specific embodiments of the disclosure described specifically herein. Such equivalents are intended to be encompassed in the scope of the disclosure.

What is claimed is:

1. A compound represented by the following structural formula:

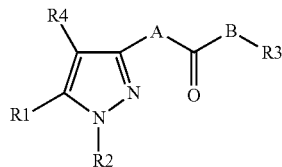

and physiologically acceptable salts thereof, wherein:
A is a direct bond,
B is N(R5),
R5 is hydrogen, OH, alkyl or substituted alkyl;
R2 comprises —(CH$_2$)$_n$—Z;
n is an integer from 0 to about 7;

wherein Z comprises, H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, alkyl-CN, O-aroyl, $O(CH_2)_jOX_3$, $O(CH_2)_jNX_1X_2$, NH-acyl, NH-aroyl, CHO, $C(halogen)_3$, $COOX_3$, $SO_3H$, $SO_2NX_1X_2$, $CONX_1X_2$, NHC(O)O-alkyl, NHSO2-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, aryl, $NO_2$, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$ wherein $X_7$ comprises H, alkyl, $NO_2$, NO, $P(O)(OX_8)_2$, PH(O)$(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$ wherein $X_9$ and $X_{10}$ each independently comprise H or alkyl Wherein m is an integer from 0 to 7 j is an integer from 0 to about 6, or k is an integer from 0 to about 2; or

R2 comprises —$(CH_2)_n$—Z;

n is an integer from 0 to about 7; and

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom; or R2 comprises —$(CH_2)_n$—Z;

n is an integer from 0 to about 7; and

Z comprises a 5 member unsaturated ring having 0 to 4 independently selected heteroatoms as ring members, a substituted 5 member unsaturated ring having 0 to 4 independently selected heteroatoms as ring members, a 6 member aromatic ring having 0 to 5 independently selected heteroatoms as ring members or a substituted 6 member aromatic ring having 0 to 5 independently selected heteroatoms; and wherein the connecting point between the —$(CH_2)_n$— group and the Z group can be any available ring carbon atom or any available ring nitrogen atom; or R2 comprises —$(CH_2)_n$—Z;

n is an integer from 0 to about 7; and

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom; or R2 comprises —$(CH_2)_n$—Z;

n is an integer from 0 to about 7; and

Z comprises

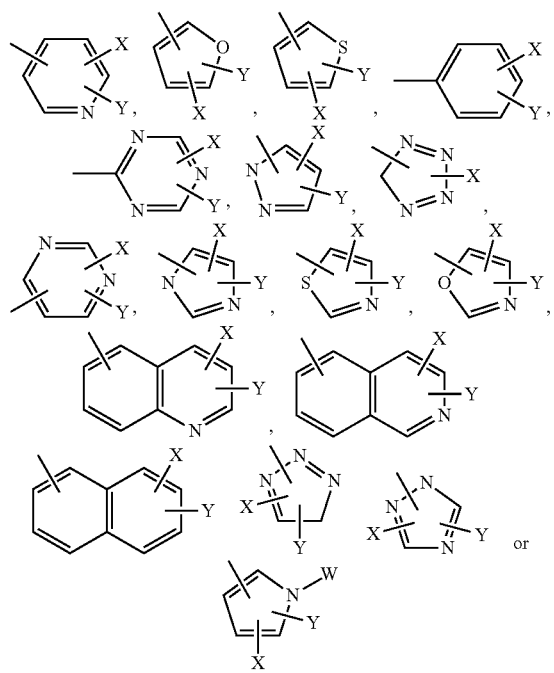

wherein X and Y each independently comprise, H, halogen, $CF_3$, $CF_2H$, $N_3$, NCS, ON, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, alkyl-CN, O-aroyl, $O(CH_2)_jOX_3$, $O(CH_2)_jNX_1X_2$, NH-acyl, NH-aroyl, CHO, $C(halogen)_3$, $COOX_3$, $SO_3H$, $SO_2NX_1X_2$, $CONX_1X_2$, NHC(O)O-alkyl, NHSO2-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, aryl, $NO_2$, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$ wherein $X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$ wherein $X_9$ and $X_{10}$ each independently comprise H or alkyl Wherein m is an integer from 0 to 7 j is an integer from 0 to about 6, or k is an integer from 0 to about 2

W comprises H or alkyl; or

R2 comprises —$(CH_2)_n$—Z;

n is an integer from 0 to about 7; and

Z comprises a carbocyclic ring having 6 ring atoms fused to a heterocyclic ring having from 5 to 7 ring atoms, a carbocyclic ring having 6 ring atoms fused to a heteroaromatic ring having from 5 to 7 ring atoms, a heterocyclic ring having 6 ring atoms fused to a heterocyclic ring having from 5 to 7 ring atoms, an heterocyclic ring having 6 ring atoms fused to a heteroaromatic ring having from 5 to 7 ring atoms, an aromatic ring having 6 ring atoms fused to a heterocyclic ring having from 5 to 7 ring atoms, an aromatic ring having 6 ring atoms fused to a heteroaromatic ring having from 5 to 7 ring atoms, a heteroaromatic ring having 6 ring atoms fused to a heterocyclic ring having from 5 to 7 ring atoms or a heteroaromatic ring having 6 ring atoms fused to a heteroaromatic ring having from 5 to 7 ring atoms; or R2 comprises —$(CH_2)_n$—Z;

n comprises an integer from 0 to about 7; and

Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 3 independently selected heteroatoms as ring members or an unsaturated ring having 6 ring atoms and 0 to 4 independently selected heteroatoms as ring members fused to an unsaturated ring having 6 or 7 ring atoms and 0 to 4 independently selected heteroatoms as ring members; or R2 comprises —$(CH_2)_m$-$Q_1$-$(CH_2)_n$—Z;

$Q_1$ comprises NH, O, S, —CH=CH—, —C≡C—, —CO, $SO_2$ or $OSO_2$;

m is an integer from 1 to about 7;

n is an integer from 0 to about 7; and wherein Z comprises, H, halogen, $CF_3$, $CF_2H$, $N_3$, NCS, ON, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, alkyl-CN, O-aroyl, $O(CH_2)_jOX_3$, $O(CH_2)_jNX_1X_2$, NH-acyl, NH-aroyl, CHO, $C(halogen)_3$, $COOX_3$, $SO_3H$, $SO_2NX_1X_2$, $CONX_1X_2$, NHC(O)O-alkyl, NHSO2-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, aryl, $NO_2$, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)alkyl$, $NX_1X_2$, $COOX_3$, $CONX_3$, $OX_7$, or O-alkyl-$X_7$ wherein $X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$ wherein $X_9$ and $X_{10}$ each independently comprise H or alkyl Wherein m is an integer from 0 to 7 j is an integer from 0 to about 6, or k is an integer from 0 to about 2; or

R2 comprises -$Q_2$-$(CH_2)_n$—Z;

$Q_2$ is optionally present and if present comprises —$CH_2$—NH, —$CH_2$—O, —$CH_2$—S, —$CH_2$—$SO_2$ or —$CH_2$—$OSO_2$;

n is an integer from 0 to about 7;

wherein Z comprises, H, halogen, $CF_3$, $CF_2H$, $N_3$, NCS, ON, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, alkyl-CN, O-aroyl, $O(CH_2)_jOX_3$, $O(CH_2)_jNX_1X_2$, NH-acyl, NH-aroyl, CHO, $C(halogen)_3$, $COOX_3$, $SO_3H$, $SO_2NX_1X_2$, $CONX_1X_2$, NHC(O)O-alkyl, NHSO2-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, aryl, $NO_2$, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)alkyl$, $NX_1X_2$, $COOX_3$, $CONX_3$, $OX_7$, or O-alkyl-$X_7$ wherein $X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$ wherein $X_9$ and $X_{10}$ each independently comprise H or alkyl Wherein m is an integer from 0 to 7 j is an integer from 0 to about 6, k is an integer from 0 to about 2; or

R2 comprises —$(CH_2)_m$-$Q_1$-$(CH_2)_n$—Z;

$Q_1$ comprises NH, O, S, CH=CH, C≡C, CO, $SO_2$ or $OSO_2$;

m is an integer from 1 to about 7;

n is an integer from 0 to about 7;

Z comprises a bicyclic ring, a heterobicyclic ring, a tricyclic ring, a heterotricyclic ring, a polycyclic ring or a heteropolycyclic ring; or R2 comprises —$(CH_2)_m$-$Q_1$-$(CH_2)_n$—Z;

$Q_1$ comprises NH, O, S, CH=CH, C≡C, CO, $SO_2$ or $OSO_2$;

m is an integer from 1 to about 7;

n is an integer from 0 to about 7;

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members; a bicyclic ring, a heterobicyclic ring, a tricyclic ring, a heterotricyclic ring, a polycyclic ring, a heteropolycyclic ring or any above group substituted on at least one available ring atom by an alkyl group or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom; or R2 comprises —(CH$_2$)$_m$-Q$_1$-(CH$_2$)$_n$—Z;

Q$_1$ comprises NH, O, S, CH═CH, C≡C, CO, SO$_2$ or OSO$_2$;

m is an integer from 1 to about 7;

n is an integer from 0 to about 7; and

Z comprises a 5 member unsaturated ring having 0 to 4 independently selected heteroatoms as ring members, a substituted 5 member unsaturated ring having 0 to 4 independently selected heteroatoms as ring members, a 6 member aromatic ring having 0 to 5 independently selected heteroatoms as ring members or a substituted 6 member aromatic ring having 0 to 5 independently selected heteroatoms; and wherein the connecting point between the —(CH$_2$)$_n$— group and the Z group can be any available ring carbon atom or any available ring nitrogen atom; or R2 comprises —(CH$_2$)$_m$-Q$_1$-(CH$_2$)$_n$—Z;

Q$_1$ comprises NH, O, S, CH═CH, C≡C, CO, SO$_2$ or OSO$_2$;

m is an integer from 1 to about 7;

n is an integer from 0 to about 7;

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom; or R2 comprises —(CH$_2$)$_m$-Q$_1$-(CH$_2$)$_n$—Z;

Q$_1$ comprises NH, O, S, CH═CH, C≡C, CO, SO$_2$ or OSO$_2$;

m is an integer from 1 to about 7;

n is an integer from 0 to about 7; and

Z comprises

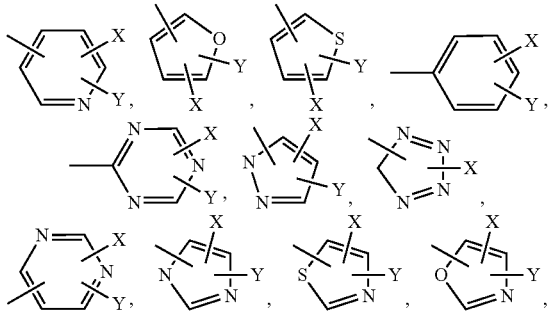

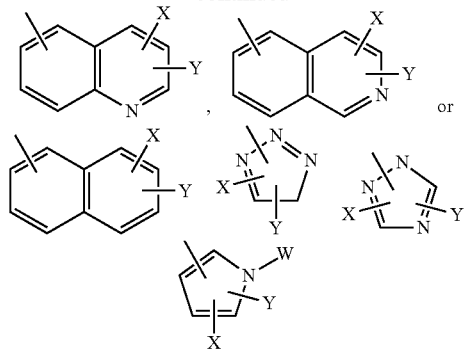

wherein X and Y each independently comprise

H, halogen, CF$_3$, CF$_2$H, N$_3$, NCS, ON, NO$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO2-alkyl, alkoxy, alkyl, alcohol, alkylmercapto, alkylamino, di-alkylamino, alkylsulfinyl or alkylsulfonyl, CX$_4$X$_5$X$_6$, —CH═CHX$_8$, —C≡CX$_8$;

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, aryl, NO$_2$, (CH$_2$)$_m$CN, hydroxyloweralkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$ wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein X$_8$ comprises H, alkyl, carbocyclic ring, heterocyclic ring, aromatic ring, heteroaromatic ring, or —CX$_9$═CHX$_{10}$ wherein X$_9$ and X$_{10}$ each independently comprise H or alkyl Wherein m is an integer from 0 to 7 j is an integer from 0 to about 6, k is an integer from 0 to about 2

W comprises H or alkyl; or

R2 comprises —(CH$_2$)$_m$-Q$_1$-(CH$_2$)$_n$—Z;

Q$_1$ comprises NH, O, S, CH═CH, C≡C, CO, SO$_2$ or OSO$_2$;

m is an integer from 1 to about 7;

n is an integer from 0 to about 7; and

Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 4 independently selected heteroatoms as ring members fused to an unsaturated ring having 6 or 7 ring atoms and 0 to 4 independently selected heteroatoms as ring members; or R2 comprises —(CH$_2$)$_m$-Q$_1$-(CH$_2$)$_n$—Z;
Q$_1$ comprises NH, O, S, CH=CH, C≡C, CO, SO$_2$ or OSO$_2$;
m is an integer from 1 to about 7;
n is an integer from 0 to about 7; and
Z comprises

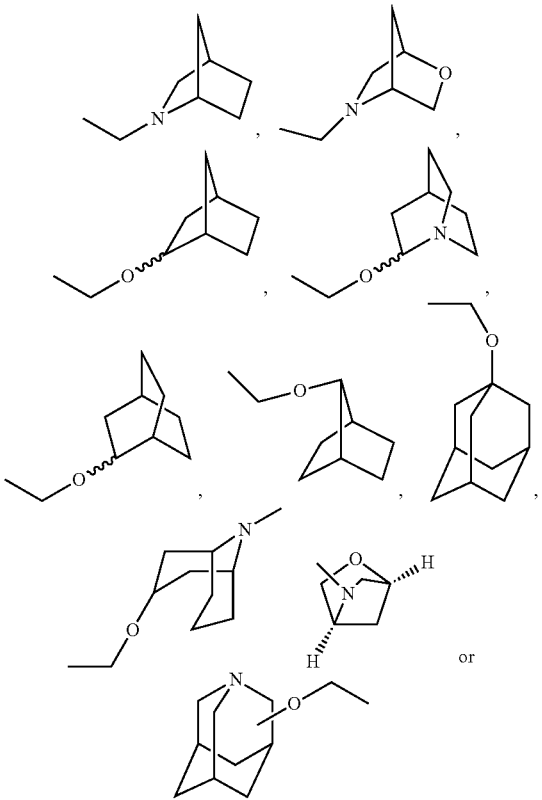

R2 comprises -T-(CH$_2$)$_n$—Z;
n comprises an integer from 0 to about 7;
T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring; and
Z comprises, H, halogen, CF$_3$, CF$_2$H, N$_3$, NCS, ON, NO$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO2-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;
X$_1$ and X$_2$ each independently comprise H or alkyl, or
X$_1$ and X$_2$ together comprise part of a heterocyclic ring having about 4 to about 7 ring members and optionally one additional heteroatom selected from O, N or S, or
X$_1$ and X$_2$ together comprise part of an imide ring having about 5 to about 6 members,
X$_3$ comprises H, alkyl, aryl, NO$_2$, (CH$_2$)$_m$CN, hydroxyloweralkyl, or alkyl-NX$_1$X$_2$,
X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$ wherein
X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein
X$_8$ comprises H, alkyl, carbocyclic ring, heterocyclic ring, aromatic ring, heteroaromatic ring, or —CX$_9$=CHX$_{10}$ wherein
X$_9$ and X$_{10}$ each independently comprise H or alkyl
Wherein m is an integer from 0 to 7
  j is an integer from 0 to about 6,
  k is an integer from 0 to about 2; or
R2 comprises -T-(CH$_2$)$_n$—Z;
n comprises an integer from 0 to about 7;
T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring; and
Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom; or
R2 comprises -T-(CH$_2$)$_n$—Z;
n comprises an integer from 0 to about 7;
T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring; and
Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom; or R2 comprises -T-(CH$_2$)$_n$—Z;

n comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring; and Z comprises

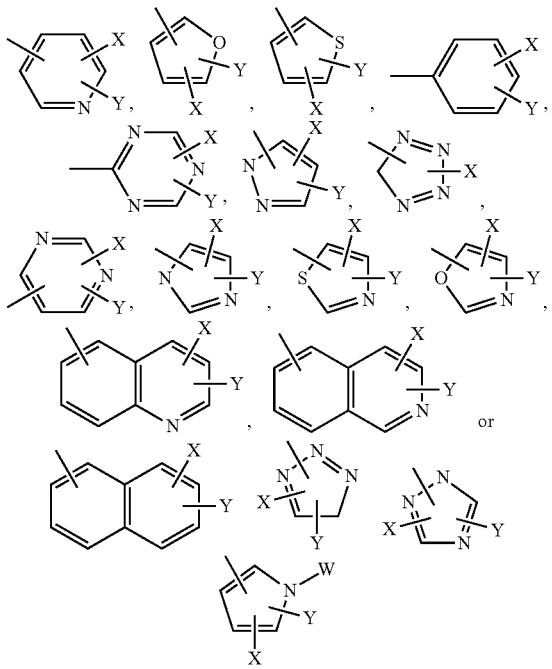

wherein X and Y each independently comprise

H, halogen, CF$_3$, CF$_2$H, N$_3$, NCS, ON, NO$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO2-alkyl, alkoxy, alkyl, alcohol, alkylmercapto, alkylamino, di-alkylamino, alkylsulfinyl or alkylsulfonyl, CX$_4$X$_5$X$_6$, —CH═CHX$_8$, —C≡CX$_8$;

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, aryl, NO$_2$, (CH$_2$)$_m$CN, hydroxyloweralkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$ wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein X$_8$ comprises H, alkyl, carbocyclic ring, heterocyclic ring, aromatic ring, heteroaromatic ring, or —CX$_9$═CHX$_{10}$ wherein X$_9$ and X$_{10}$ each independently comprise H or alkyl Wherein m is an integer from 0 to 7 j is an integer from 0 to about 6, k is an integer from 0 to about 2

W comprises H or alkyl; or

R2 comprises -T-(CH$_2$)$_n$—Z;

n comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring; and Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 3 independently selected heteroatoms as ring members fused to an unsaturated ring having 6 or 7 ring atoms and 0 to 4 independently selected heteroatoms as ring members; or R2 comprises -T-(CH$_2$)$_m$-Q$_1$-(CH$_2$)$_n$—Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Q$_1$ comprises NH, O, S, CH═CH, C≡C, CO, SO$_2$ or OSO$_2$; and

Z comprises, H, halogen, CF$_3$, CF$_2$H, N$_3$, NCS, ON, NO$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO2-alkyl, alkoxy, alkyl, alcohol, alkylmercapto, alkylamino, di-alkylamino, alkylsulfinyl or alkylsulfonyl, CX$_4$X$_5$X$_6$, —CH═CHX$_8$, —C≡CX$_8$;

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, aryl, NO$_2$, (CH$_2$)$_m$CN, hydroxyloweralkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$ wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein $X_8$ comprises H, alkyl, carbocyclic ring, heterocyclic ring, aromatic ring, heteroaromatic ring, or —$CX_9$=$CHX_{10}$ wherein $X_9$ and $X_{10}$ each independently comprise H or alkyl Wherein m is an integer from 0 to 7 j is an integer from 0 to about 6, k is an integer from 0 to about 2; or

R2 comprises -T-$(CH_2)_m$-$Q_1$-$(CH_2)_n$—Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

$Q_1$ comprises NH, O, S, CH=CH, C≡C, CO, $SO_2$ or $OSO_2$; and

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom; or R2 comprises -T-$(CH_2)_m$-$Q_1$-$(CH_2)_n$—Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

$Q_1$ comprises NH, O, S, CH=CH, C≡C, CO, $SO_2$ or $OSO_2$; and

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom; or R2 comprises -T-$(CH_2)_m$-$Q_1$-$(CH_2)_n$—Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

$Q_1$ comprises N, O, S, CH=CH, C≡C, CO, $SO_2$ or $OSO_2$; and

Z comprises wherein X and Y each independently comprise

H, halogen, $CF_3$, $CF_2H$, $N_3$, NCS, ON, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, alkyl-CN, O-aroyl, $O(CH_2)_jOX_3$, $O(CH_2)_jNX_1X_2$, NH-acyl, NH-aroyl, CHO, $C(halogen)_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, aryl, $NO_2$, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$ wherein $X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$ wherein $X_9$ and $X_{10}$ each independently comprise H or alkyl
Wherein m is an integer from 0 to 7
j is an integer from 0 to about 6,
k is an integer from 0 to about 2
W comprises H or alkyl; or
R2 comprises -T-$(CH_2)_m$-$Q_1$-$(CH_2)_n$—Z;
m and n independently comprises an integer from 0 to about 7;
T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;
$Q_1$ comprises NH, O, S, CH=CH, C≡C, CO, $SO_2$ or $OSO_2$; and
Z comprises an unsaturated ring having 5 ring atoms and 0 to 2 independently selected heteroatoms as ring members fused to an unsaturated ring having 5 ring atoms and 0 to 2 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 3 independently selected heteroatoms as ring members fused to an unsaturated ring having 6 or 7 ring atoms and 0 to 4 independently selected heteroatoms as ring members, or
R2 comprises -T-$(CH_2)_m$-$Q_1$-$(CH_2)_n$—Z;
T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;
m and n independently comprises an integer from 0 to about 7;
$Q_1$ comprises NH, O, S, CH=CH, C≡C, CO, $SO_2$ or $OSO_2$; and
Z comprises:

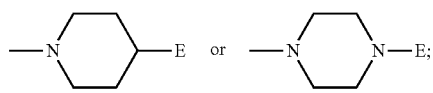

E comprises a C1 to about C4, linear or branched alkyl group, a phenyl group, a substituted phenyl group, a benzyl group or a substituted benzyl group; or
R2 comprises -T-$(CH_2)_m$-$Q_1$-$(CH_2)_n$—Z;
T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;
m and n independently comprises an integer from 0 to about 7;

$Q_1$ comprises NH, O, S, CH=CH, C≡C, CO, $SO_2$ or $OSO_2$;
Z comprises

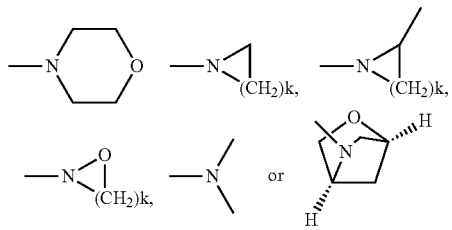

k is an integer from 1 to about 5,
$A_1$ and $A_2$ each independently comprise a C1 to about C4 alkyl group, a phenyl group or a substituted phenyl group;
R3 comprises

wherein G comprises CH, $C(CH_3)$, C(CN) or N,
L, K and J each independently comprise $(CH_2)_n$, $(CH_3)_2$, C=O, O, —CHOH, $C(CH_3)OM_1$, $C(CH_2)_n(X)Y$, $NM_1$, $SO_2$ SO or S, and at least one of L, K or J is $SO_2$,
n is an integer from 0 to about 7;
$M_1$ is H, alkyl, $C(O)M_2$ where
$M_2$ is H, alkyl, $NM_3M_4$, $OM_5$ and $M_3$, $M_4$ and $M_5$ are independently H, OH or alkyl
and X and Y each independently comprise, H, halogen, $CF_3$, $CF_2H$, $N_3$, NCS, ON, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, alkyl-CN, O-aroyl, $O(CH_2)_jOX_3$, $O(CH_2)_jNX_1X_2$, NH-acyl, NH-aroyl, CHO, $C(halogen)_3$, $COOX_3$, $SO_3H$, $SO_2NX_1X_2$, $CONX_1X_2$, NHC(O)O-alkyl, $NHSO2$-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;
$X_1$ and $X_2$ each independently comprise H or alkyl, or
$X_1$ and $X_2$ together comprise part of a heterocyclic ring having about 4 to about 7 ring members and optionally one additional heteroatom selected from O, N or S, or
$X_1$ and $X_2$ together comprise part of an imide ring having about 5 to about 6 members,
$X_3$ comprises H, alkyl, $NO_2$, $(CH_2)_mCN$, hydroxylower-alkyl, or alkyl-$NX_1X_2$,
$X_4$, $X_5$, and $X_6$ each independently comprise H, alkyl, carbocyclic ring, hydroxyloweralkyl, alkyl-OH, halogen, CN, SNO, $S(SO_2)alkyl$, $NX_1X_2$, $COOX_3$, $CONX_3$, $OX_7$, or O-alkyl-$X_7$ wherein
$X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein
$X_8$ comprises H, alkyl, carbocyclic ring, heterocyclic ring, aromatic ring, heteroaromatic ring, or —$CX_9$=$CHX_{10}$ wherein $X_9$ and $X_{10}$ each independently comprise H or alkyl Wherein m is an integer from 0 to 7 j is an integer from 0 to about 6, or k is an integer from 0 to about 2 or

R1 comprises -T-$(CH_2)_m$-Q-$(CH_2)_n$—Z, m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Q comprises CH=CH, C≡C;

Z comprises

H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, alkyl-CN, O-aroyl, $O(CH_2)_jOX_3$, $O(CH_2)_jNX_1X_2$, NH-acyl, NH-aroyl, CHO, $C(halogen)_3$, $COOX_3$, $SO_3H$, $SO_2NX_1X_2$, $CONX_1X_2$, NHC(O)O-alkyl, NHSO2-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)alkyl$, $NX_1X_2$, $COOX_3$, $CONX_3$, $OX_7$, or O-alkyl-$X_7$ wherein $X_7$ comprises H, alkyl, $NO_2$, NO, $P(O)(OX_8)_2$, PH(O)$(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$ wherein $X_9$ and $X_{10}$ each independently comprise H or alkyl Wherein m is an integer from 0 to 7 j is an integer from 0 to about 6, or k is an integer from 0 to about 2; or

R1 comprises -T-$(CH_2)_m$-Q-$(CH_2)_n$—Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Q comprises CH=CH, C≡C; and

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom; or R1 comprises -T-$(CH_2)_m$-Q-$(CH_2)_n$—Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Q comprises CH=CH, C≡C; and

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom; or R1 comprises -T-$(CH_2)_m$-Q-$(CH_2)_n$—Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Q comprises CH=CH, C≡C; and

Z comprises

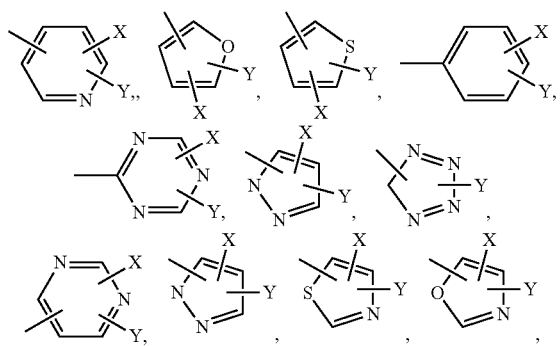

-continued

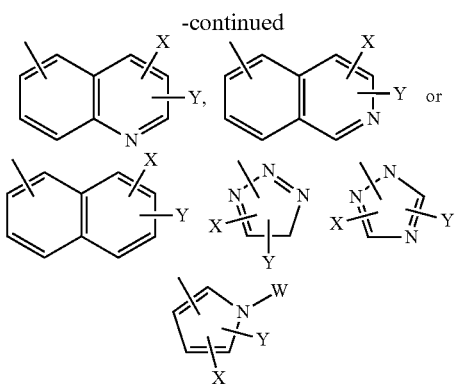

wherein X and Y each independently comprise
H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, alkyl-CN, O-aroyl, $O(CH_2)_jOX_3$, $O(CH_2)_jNX_1X_2$, NH-acyl, NH-aroyl, CHO, $C(halogen)_3$, $COOX_3$, $SO_3H$, $SO_2NX_1X_2$, $CONX_1X_2$, NHC(O)O-alkyl, NHSO2-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;
$X_1$ and $X_2$ each independently comprise H or alkyl, or
$X_1$ and $X_2$ together comprise part of a heterocyclic ring having about 4 to about 7 ring members and optionally one additional heteroatom selected from O, N or S, or
$X_1$ and $X_2$ together comprise part of an imide ring having about 5 to about 6 members,
$X_3$ comprises H, alkyl, $NO_2$, $(CH_2)_mCN$, hydroxyloweralkyl, or alkyl-$NX_1X_2$,
$X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$ wherein
$X_7$ comprises H, alkyl, $NO_2$, NO, $P(O)(OX_8)_2$, PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein
$X_8$ comprises H, alkyl, carbocyclic ring, heterocyclic ring, aromatic ring, heteroaromatic ring, or —$CX_9$=$CHX_{10}$ wherein
$X_9$ and $X_{10}$ each independently comprise H or alkyl
Wherein m is an integer from 0 to 7
j is an integer from 0 to about 6,
k is an integer from 0 to about 2,
W comprises H or alkyl; or
R1 comprises -T-$(CH_2)_m$-Q-$(CH_2)_n$—Z;
m and n independently comprises an integer from 0 to about 7;
T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;
Q comprises CH=CH, C≡C; and
Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 3 independently selected heteroatoms as ring members fused to an unsaturated ring having 6 or 7 ring atoms and 0 to 4 independently selected heteroatoms as ring members; or
R1 comprises -T-$(CH_2)_m$-Q-$(CH_2)_n$—Z;
T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;
m and n independently comprises an integer from 0 to about 7;
Q comprises CH=CH, C≡C;
Z comprises

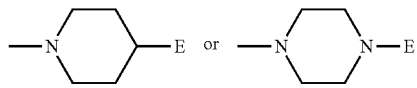

E comprises a C1 to about C4, linear or branched alkyl group, a phenyl group, a substituted phenyl group, a benzyl group or a substituted benzyl group; or
R1 comprises -T-$(CH_2)_m$-Q-$(CH_2)_n$—Z;
T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;
m and n independently comprises an integer from 0 to about 7;
Q comprises CH=CH, C≡C; and
Z comprises

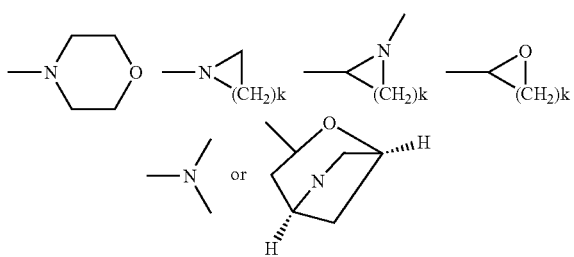

k is an integer from 1 to about 5, and
$A_1$ and $A_2$ each independently comprise a C1 to about C4 alkyl group, a phenyl group or a substituted phenyl group; or
R1 comprises —$(CH_2)_n$—Z;
n is an integer from 0 to about 7;
wherein Z comprises, H, halogen, $CF_3$, $CF_2H$, $N_3$, NCS, ON, $NO_2$, $NX_1X_2$, $OX_3$, $SX_3$, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, alkyl-CN, O-aroyl, $O(CH_2)_jOX_3$, $O(CH_2)_jNX_1X_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO2-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, aryl, NO$_2$, (CH$_2$)$_m$CN, hydroxyloweralkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$ wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein X$_8$ comprises H, alkyl, carbocyclic ring, heterocyclic ring, aromatic ring, heteroaromatic ring, or —CX$_9$=CHX$_{10}$ wherein X$_9$ and X$_{10}$ each independently comprise H or alkyl Wherein m is an integer from 0 to 7 j is an integer from 0 to about 6, or k is an integer from 0 to about 2; or

R1 comprises —(CH$_2$)$_n$—Z;

n is an integer from 0 to about 7; and

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom; or R1 comprises —(CH$_2$)$_n$—Z;

n is an integer from 0 to about 7; and

Z comprises a 5 member unsaturated ring having 0 to 4 independently selected heteroatoms as ring members, a substituted 5 member unsaturated ring having 0 to 4 independently selected heteroatoms as ring members, a 6 member aromatic ring having 0 to 5 independently selected heteroatoms as ring members or a substituted 6 member aromatic ring having 0 to 5 independently selected heteroatoms; and wherein the connecting point between the —(CH$_2$)$_n$— group and the Z group can be any available ring carbon atom or any available ring nitrogen atom; or R1 comprises —(CH$_2$)$_n$—Z;

n is an integer from 0 to about 7; and

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom; or R1 comprises —(CH$_2$)$_n$—Z;

n is an integer from 0 to about 7; and

Z comprises

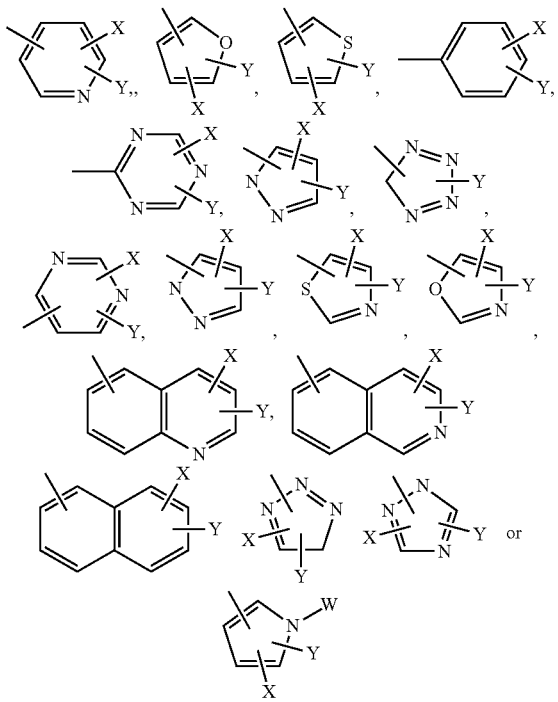

wherein X and Y each independently comprise, H, halogen, CF$_3$, CF$_2$H, N$_3$, NCS, CN, NO$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO2-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, aryl, NO$_2$, (CH$_2$)$_m$CN, hydroxyloweralkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$ wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein $X_8$ comprises H, alkyl, carbocyclic ring, heterocyclic ring, aromatic ring, heteroaromatic ring, or —$CX_9$=$CHX_{10}$ wherein $X_9$ and $X_{10}$ each independently comprise H or alkyl Wherein m is an integer from 0 to 7 j is an integer from 0 to about 6, or k is an integer from 0 to about 2

W comprises H or alkyl; or

R1 comprises —$(CH_2)_n$—Z;

n is an integer from 0 to about 7; and

Z comprises a carbocyclic ring having 6 ring atoms fused to a heterocyclic ring having from 5 to 7 ring atoms, a carbocyclic ring having 6 ring atoms fused to a heteroaromatic ring having from 5 to 7 ring atoms, a heterocyclic ring having 6 ring atoms fused to a heterocyclic ring having from 5 to 7 ring atoms, an heterocyclic ring having 6 ring atoms fused to a heteroaromatic ring having from 5 to 7 ring atoms, an aromatic ring having 6 ring atoms fused to a heterocyclic ring having from 5 to 7 ring atoms, an aromatic ring having 6 ring atoms fused to a heteroaromatic ring having from 5 to 7 ring atoms, a heteroaromatic ring having 6 ring atoms fused to a heterocyclic ring having from 5 to 7 ring atoms or a heteroaromatic ring having 6 ring atoms fused to a heteroaromatic ring having from 5 to 7 ring atoms; or R1 comprises —$(CH_2)_n$—Z;

n comprises an integer from 0 to about 7; and

Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 3 independently selected heteroatoms as ring members or an unsaturated ring having 6 ring atoms and 0 to 4 independently selected heteroatoms as ring members fused to an unsaturated ring having 6 or 7 ring atoms and 0 to 4 independently selected heteroatoms as ring members; or R1 comprises —$(CH_2)_m$-$Q_1$-$(CH_2)_n$—Z;

$Q_1$ comprises NH, O, S, —CH=CH—, —C≡C—, —CO, $SO_2$ or $OSO_2$;

m is an integer from 1 to about 7;

n is an integer from 0 to about 7; and wherein Z comprises, H, halogen, $CF_3$, $CF_2H$, $N_3$, NCS, ON, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, alkyl-CN, O-aroyl, $O(CH_2)_jOX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, NHC(O)O-alkyl, NHSO2-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, aryl, $NO_2$, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$ wherein $X_7$ comprises H, alkyl, $NO_2$, NO, $P(O)(OX_8)_2$, PH(O)(O$X_8$), $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$ wherein $X_9$ and $X_{10}$ each independently comprise H or alkyl Wherein m is an integer from 0 to 7 j is an integer from 0 to about 6, or k is an integer from 0 to about 2; or

R1 comprises -$Q_2$-$(CH_2)_n$—Z;

$Q_2$ is optionally present and if present comprises —$CH_2$—NH, —$CH_2$—O, —$CH_2$—S, —$CH_2$—$SO_2$ or —$CH_2$—$OSO_2$;

n is an integer from 0 to about 7;

wherein Z comprises, H, halogen, $CF_3$, $CF_2H$, $N_3$, NCS, ON, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, alkyl-CN, O-aroyl, $O(CH_2)_jOX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, NHC(O)O-alkyl, NHSO2-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, aryl, $NO_2$, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$ wherein $X_7$ comprises H, alkyl, $NO_2$, NO, $P(O)(OX_8)_2$, PH(O)(O$X_8$), $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$ wherein $X_9$ and $X_{10}$ each independently comprise H or alkyl Wherein m is an integer from 0 to 7 j is an integer from 0 to about 6, k is an integer from 0 to about 2; or

R1 comprises —$(CH_2)_m$-$Q_1$-$(CH_2)_n$—Z;

$Q_1$ comprises NH, O, S, CH=CH, C≡C, CO, $SO_2$ or $OSO_2$;

m is an integer from 1 to about 7;

n is an integer from 0 to about 7;

Z comprises a bicyclic ring, a heterobicyclic ring, a tricyclic ring, a heterotricyclic ring, a polycyclic ring or a heteropolycyclic ring; or R1 comprises —$(CH_2)_m$-$Q_1$-$(CH_2)_n$—Z;

$Q_1$ comprises NH, O, S, CH=CH, C≡C, CO, $SO_2$ or $OSO_2$;

m is an integer from 1 to about 7;

n is an integer from 0 to about 7;

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members; a bicyclic ring, a heterobicyclic ring, a tricyclic ring, a heterotricyclic ring, a polycyclic ring, a heteropolycyclic ring or any above group substituted on at least one available ring atom by an alkyl group or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom; or R1 comprises —(CH$_2$)$_m$-Q$_1$-(CH$_2$)$_n$—Z;

Q$_1$ comprises NH, O, S, CH=CH, C≡C, CO, SO$_2$ or OSO$_2$;

m is an integer from 1 to about 7;

n is an integer from 0 to about 7; and

Z comprises a 5 member unsaturated ring having 0 to 4 independently selected heteroatoms as ring members, a substituted 5 member unsaturated ring having 0 to 4 independently selected heteroatoms as ring members, a 6 member aromatic ring having 0 to 5 independently selected heteroatoms as ring members or a substituted 6 member aromatic ring having 0 to 5 independently selected heteroatoms; and wherein the connecting point between the —(CH$_2$)$_n$— group and the Z group can be any available ring carbon atom or any available ring nitrogen atom; or R1 comprises —(CH$_2$)$_m$-Q$_1$-(CH$_2$)$_n$—Z;

Q$_1$ comprises NH, O, S, CH=CH, C≡C, CO, SO$_2$ or OSO$_2$;

m is an integer from 1 to about 7;

n is an integer from 0 to about 7;

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom; or R1 comprises —(CH$_2$)$_m$-Q$_1$-(CH$_2$)$_n$—Z;

Q$_1$ comprises NH, O, S, CH=CH, C≡C, CO, SO$_2$ or OSO$_2$;

m is an integer from 1 to about 7;

n is an integer from 0 to about 7; and

Z comprises

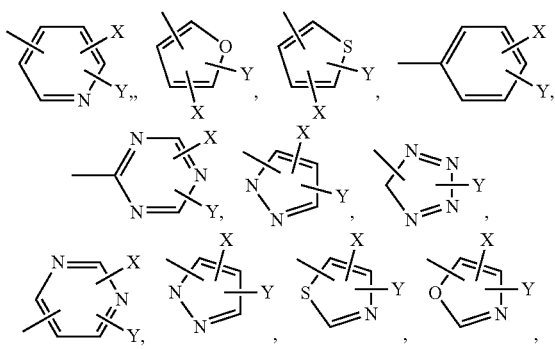

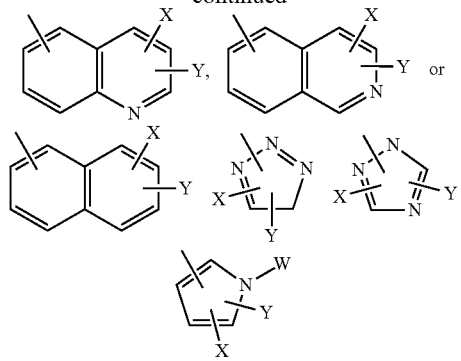

wherein X and Y each independently comprise

H, halogen, CF$_3$, CF$_2$H, N$_3$, NCS, CN, NO$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO2-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, aryl, NO$_2$, (CH$_2$)$_m$CN, hydroxyloweralkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$ wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein X$_8$ comprises H, alkyl, carbocyclic ring, heterocyclic ring, aromatic ring, heteroaromatic ring, or —CX$_9$=CHX$_{10}$ wherein X$_9$ and X$_{10}$ each independently comprise H or alkyl Wherein m is an integer from 0 to 7 j is an integer from 0 to about 6, k is an integer from 0 to about 2

W comprises H or alkyl; or

R1 comprises —(CH$_2$)$_m$-Q$_1$-(CH$_2$)$_n$—Z;

Q$_1$ comprises NH, O, S, CH=CH, C≡C, CO, SO$_2$ or OSO$_2$;

m is an integer from 1 to about 7;

n is an integer from 0 to about 7; and

Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 4 independently selected heteroatoms as ring members fused to an unsaturated ring having 6 or 7 ring atoms and 0 to 4 independently selected heteroatoms as ring members; or R1 comprises —(CH$_2$)$_m$-Q$_1$-(CH$_2$)$_n$—Z;

Q$_1$ comprises NH, O, S, CH=CH, C≡C, CO, SO$_2$ or OSO$_2$;

m is an integer from 1 to about 7;

n is an integer from 0 to about 7; and

Z comprises

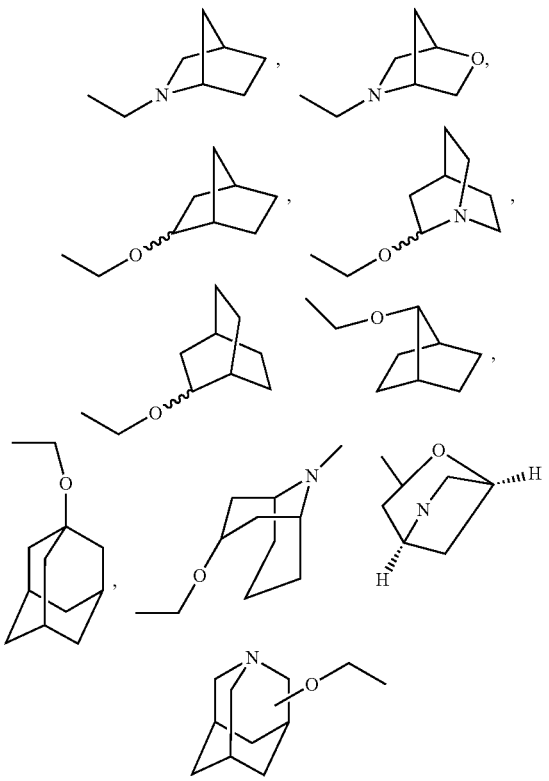

R1 comprises -T-(CH$_2$)$_n$—Z;

n comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring; and Z comprises, H, halogen, CF$_3$, CF$_2$H, N$_3$, NCS, CN, NO$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO2-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, aryl, NO$_2$, (CH$_2$)$_m$CN, hydroxyloweralkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$ wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein X$_8$ comprises H, alkyl, carbocyclic ring, heterocyclic ring, aromatic ring, heteroaromatic ring, or —CX$_9$=CHX$_{10}$ wherein X$_9$ and X$_{10}$ each independently comprise H or alkyl Wherein m is an integer from 0 to 7 j is an integer from 0 to about 6, k is an integer from 0 to about 2; or

R1 comprises -T-(CH$_2$)$_n$—Z;

n comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring; and Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom; or R1 comprises -T-(CH$_2$)$_n$—Z;

n comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring; and Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom; or R1 comprises -T-(CH$_2$)$_n$—Z;

n comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring; and Z comprises

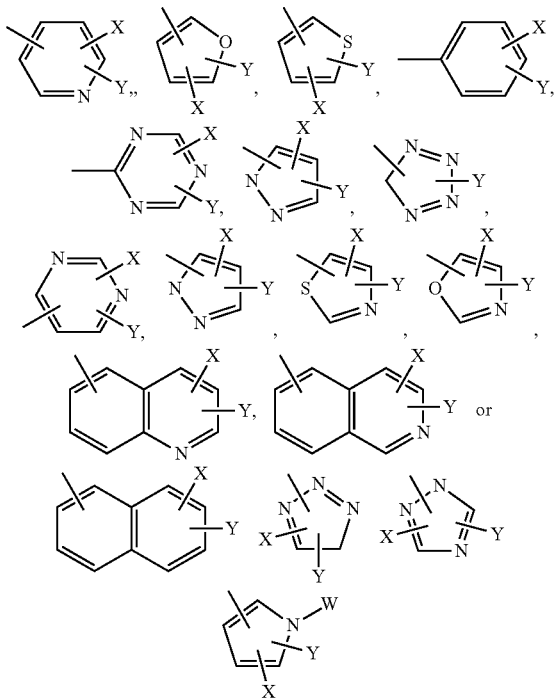

wherein X and Y each independently comprise

H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, alkyl-CN, O-aroyl, $O(CH_2)_jOX_3$, $O(CH_2)_jNX_1X_2$, NH-acyl, NH-aroyl, CHO, $C(halogen)_3$, $COOX_3$, $SO_3H$, $SO_2NX_1X_2$, $CONX_1X_2$, NHC(O)O-alkyl, NHSO2-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, aryl, $NO_2$, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)alkyl$, $NX_1X_2$, $COOX_3$, $CONX_3$, $OX_7$, or O-alkyl-$X_7$ wherein $X_7$ comprises H, alkyl, $NO_2$, NO, $P(O)(OX_8)_2$, PH(O)$(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$ wherein $X_9$ and $X_{10}$ each independently comprise H or alkyl Wherein m is an integer from 0 to 7 j is an integer from 0 to about 6, k is an integer from 0 to about 2

W comprises H or alkyl; or

R1 comprises -T-$(CH_2)_n$—Z;

n comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring; and Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 3 independently selected heteroatoms as ring members fused to an unsaturated ring having 6 or 7 ring atoms and 0 to 4 independently selected heteroatoms as ring members; or R1 comprises -T-Q-$(CH_2)_n$—Z, each n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Q comprises CH=CH, C≡C;

Z comprises H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, alkyl-CN, O-aroyl, $O(CH_2)_jOX_3$, $O(CH_2)_jNX_1X_2$, NH-acyl, NH-aroyl, CHO, $C(halogen)_3$, $COOX_3$, $SO_3H$, $SO_2NX_1X_2$, $CONX_1X_2$, NHC(O)O-alkyl, NHSO2-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)alkyl$, $NX_1X_2$, $COOX_3$, $CONX_3$, $OX_7$, or O-alkyl-$X_7$ wherein $X_7$ comprises H, alkyl, $NO_2$, NO, $P(O)(OX_8)_2$, PH(O)$(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$ wherein $X_9$ and $X_{10}$ each independently comprise H or alkyl Wherein m is an integer from 0 to 7 j is an integer from 0 to about 6, or k is an integer from 0 to about 2; or

R1 comprises -T-Q-$(CH_2)_n$—Z;

each n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Q comprises CH=CH, C≡C; and

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom; or R1 comprises -T-Q-$(CH_2)_n$—Z;

each n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Q comprises CH=CH, C≡C; and

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom; or R1 comprises -T-Q-$(CH_2)_n$—Z;

each n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Q comprises CH=CH, C≡C; and

Z comprises wherein X and Y each independently comprise

H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, alkyl-CN, O-aroyl, $O(CH_2)_jOX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, NHC(O)O-alkyl, NHSO2-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$ wherein $X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$ wherein $X_9$ and $X_{10}$ each independently comprise H or alkyl Wherein m is an integer from 0 to 7 j is an integer from 0 to about 6, k is an integer from 0 to about 2,

W comprises H or alkyl; or

R1 comprises -T-Q-$(CH_2)_n$—Z;

each n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Q comprises CH=CH, C≡C; and

Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 3 independently selected heteroatoms as ring members fused to an unsaturated ring having 6 or 7 ring atoms and 0 to 4 independently selected heteroatoms as ring members; or R1 comprises -T-Q-$(CH_2)_n$—Z;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

each n independently comprises an integer from 0 to about 7;

Q comprises CH=CH, C≡C;

Z comprises

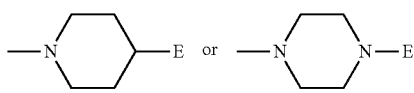

E comprises a C1 to about C4, linear or branched alkyl group, a phenyl group, a substituted phenyl group, a benzyl group or a substituted benzyl group; or R1 comprises -T-Q-$(CH_2)_n$—Z;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

each n independently comprises an integer from 0 to about 7;

Q comprises CH=CH, C≡C; and

Z comprises

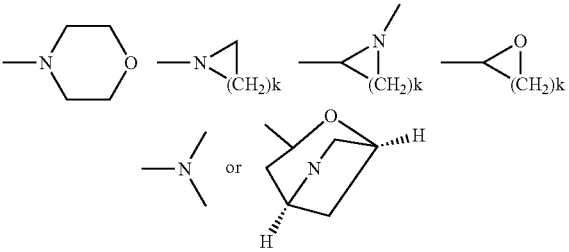

k is an integer from 1 to about 5, and $A_1$ and $A_2$ each independently comprise a C1 to about C4 alkyl group, a phenyl group or a substituted phenyl group; and R4 comprises H, halogen, $CF_3$, $CF_2H$, $N_3$, NCS, CN, $NO_2$, $NX_1X_2$, OH, $ONO_2$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, alkyl-CN, O-aroyl, $O(CH_2)_jOX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, NHC(O)O-alkyl, NHSO2-alkyl, alkoxy, alkyl, alcohol, alkylmercapto, alkylamino, di-alkylamino, alkylsulfinyl or alkylsulfonyl, $CX_4X_5X_6$, —CH=CHX$_8$, —C≡CX$_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$ wherein $X_7$ comprises H, alkyl, $NO_2$, NO, $P(O)(OX_8)_2$, PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —CX$_9$=CHX$_{10}$ wherein $X_9$ and $X_{10}$ each independently comprise H or alkyl Wherein m is an integer from 0 to 7 j is an integer from 0 to about 6, or k is an integer from 0 to about 2; or

R4 comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring or a heteropolycyclic ring; or R4 comprises

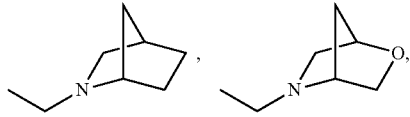

-continued

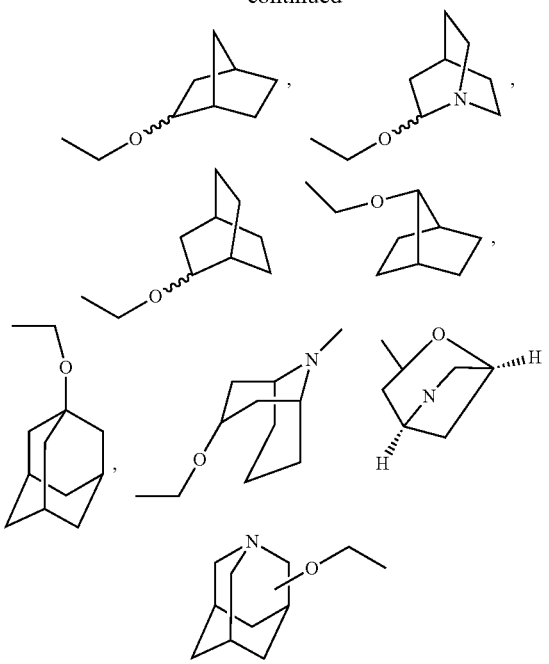

R4 comprises —(CH$_2$)$_d$—Z;

d is an integer from 1 to about 6;

Z comprises H, halogen, CF$_3$, CF$_2$H, N$_3$, NCS, CN, NO$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO2-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, NO$_2$, (CH$_2$)$_m$CN, hydroxylower-alkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$ wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein X$_8$ comprises H, alkyl, carbocyclic ring, heterocyclic ring, aromatic ring, heteroaromatic ring, or —CX$_9$=CHX$_{10}$ wherein X$_9$ and X$_{10}$ each independently comprise H or alkyl Wherein m is an integer from 0 to 7 j is an integer from 0 to about 6, k is an integer from 0 to about 2; or

R4 comprises —(CH$_2$)$_d$—Z;

d is an integer from 1 to about 6; and

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_d$— group and the Z group can be any available ring carbon atom or any available ring nitrogen atom; or R4 comprises —(CH$_2$)$_d$—Z;

d is an integer from 1 to about 6; and

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_d$— group and the Z group can be any available ring carbon atom or any available ring nitrogen atom; or R4 comprises —(CH$_2$)$_m$-Q$_1$-(CH$_2$)$_n$—Z;

Q$_1$ comprises NH, O, S, CH=CH, C≡C, CO, SO$_2$ or OSO$_2$;

m is an integer from 1 to about 7;

n is an integer from 0 to about 7; and

Z comprises

H, halogen, CF$_3$, CF$_2$H, N$_3$, NCS, CN, NO$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO2-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, NO$_2$, (CH$_2$)$_m$CN, hydroxylower-alkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$ wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein X$_8$ comprises H, alkyl, carbocyclic ring, heterocyclic ring, aromatic ring, heteroaromatic ring, or —CX$_9$=CHX$_{10}$ wherein X$_9$ and X$_{10}$ each independently comprise H or alkyl Wherein m is an integer from 0 to 7 j is an integer from 0 to about 6, or k is an integer from 0 to about 2; or

R4 comprises —(CH$_2$)$_m$-Q$_1$-(CH$_2$)$_n$—Z;

Q$_1$ comprises NH, O, S, CH=CH, C≡C, CO, SO$_2$ or OSO$_2$;

m is an integer from 1 to about 7;
n is an integer from 0 to about 7; and
Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members; a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom; or R4 comprises —(CH$_2$)$_m$-Q$_1$-(CH$_2$)$_n$—Z;
Q$_1$ comprises NH, O, S, CH=CH, C≡C, CO, SO$_2$ or OSO$_2$;
m is an integer from 1 to about 7;
n is an integer from 0 to about 7; and
Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom; or R4 comprises —(CH$_2$)$_m$-Q$_1$-(CH$_2$)$_n$—Z;
Q$_1$ comprises NH, O, S, CH=CH, C≡C, CO, SO$_2$ or OSO$_2$;
m is an integer from 1 to about 7;
n is an integer from 0 to about 7; and
Z comprises

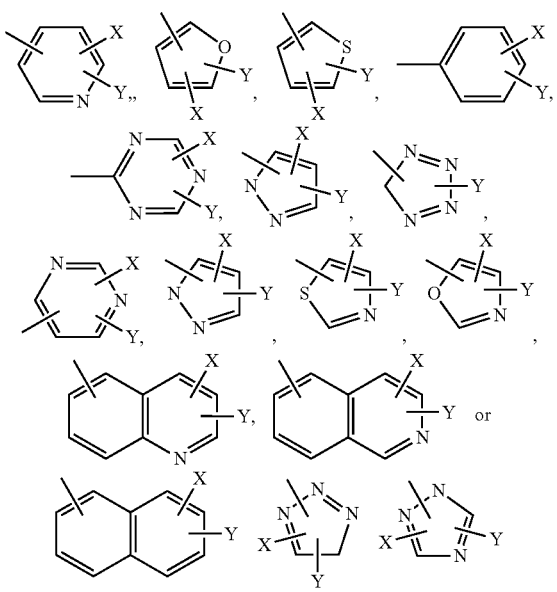

wherein X and Y each independently comprise
H, halogen, CF$_3$, CF$_2$H, N$_3$, NCS, CN, NO$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO2-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$ and X$_2$ each independently comprise H or alkyl, or
X$_1$ and X$_2$ together comprise part of a heterocyclic ring having about 4 to about 7 ring members and optionally one additional heteroatom selected from O, N or S, or
X$_1$ and X$_2$ together comprise part of an imide ring having about 5 to about 6 members,
X$_3$ comprises H, alkyl, NO$_2$, (CH$_2$)$_m$CN, hydroxylower-alkyl, or alkyl-NX$_1$X$_2$,
X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$ wherein
X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein
X$_8$ comprises H, alkyl, carbocyclic ring, heterocyclic ring, aromatic ring, heteroaromatic ring, or —CX$_9$=CHX$_{10}$ wherein
X$_9$ and X$_{10}$ each independently comprise H or alkyl
Wherein m is an integer from 0 to 7
j is an integer from 0 to about 6,
k is an integer from 0 to about 2,
W comprises H or alkyl.

2. A pharmaceutical composition containing a therapeutically effective amount of at least one compound of claim 1.

3. A method of modulating the function of cannabinoid receptors in an individual or animal comprising administering to the individual or animal a therapeutically effective amount of at least one compound of claim 1.

4. The method of claim 3 comprising selectively stimulating a CB1 cannabinoid receptor in said individual or animal.

5. A method of treating or reducing the severity of a condition selected from the group consisting of obesity; metabolic disorders consisting of insulin related deficiencies and lipid profiles, hepatic diseases, cardiometabolic diseases, diabetes and appetite disorders; cancer chemotherapy; benign prostatic hypertrophy; schizophrenia; Parkinson's disease; marijuana abuse; and alcohol, opioid, nicotine or cocaine addiction in an individual or animal having that condition comprising administering to the individual or animal a therapeutically effective amount of at least one compound of claim 1.

6. A compound of claim 1 wherein at least one atom in the compound is an unnatural isotope.

7. A compound of claim 1, and physiologically accepted salts thereof, selected from one of the following structures:

15
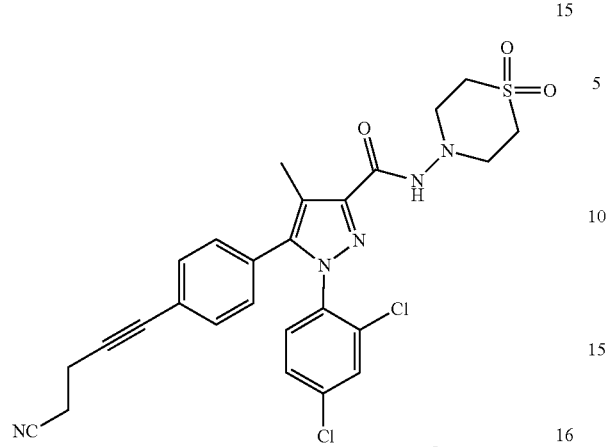
16
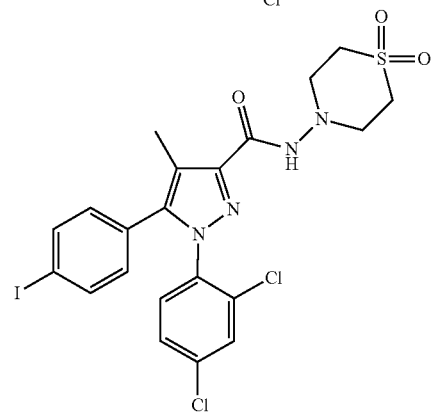
17
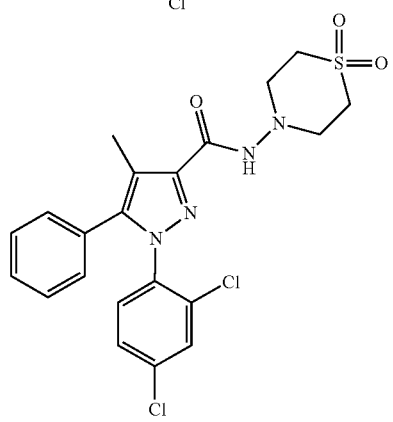
24
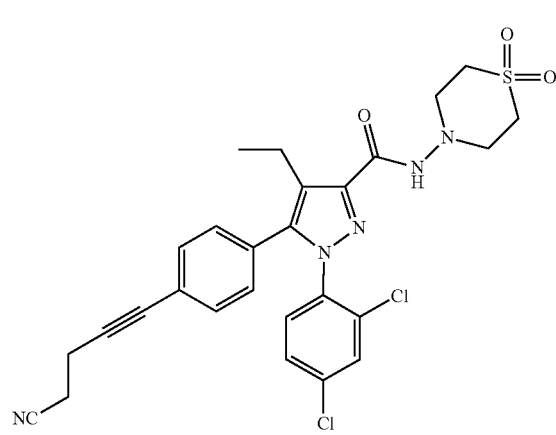
31
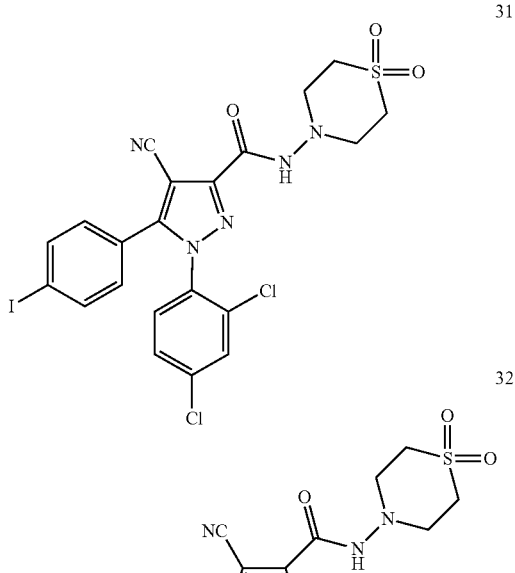
32
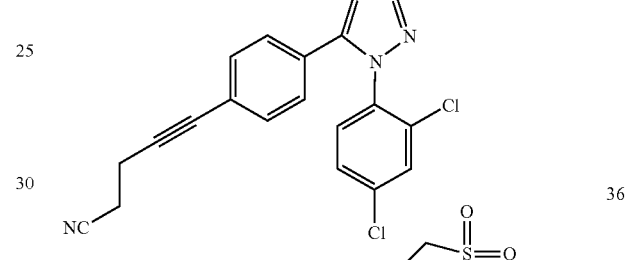
36
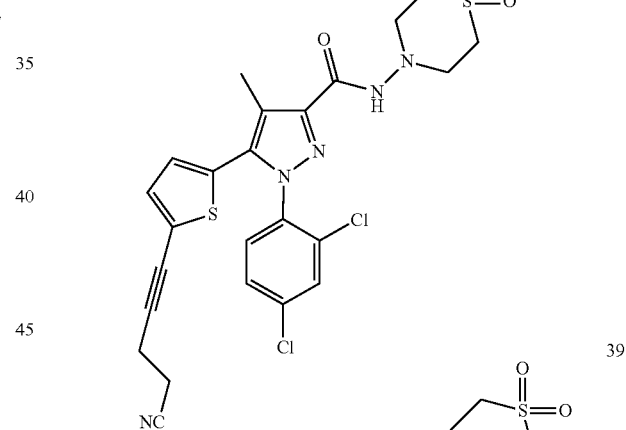
39
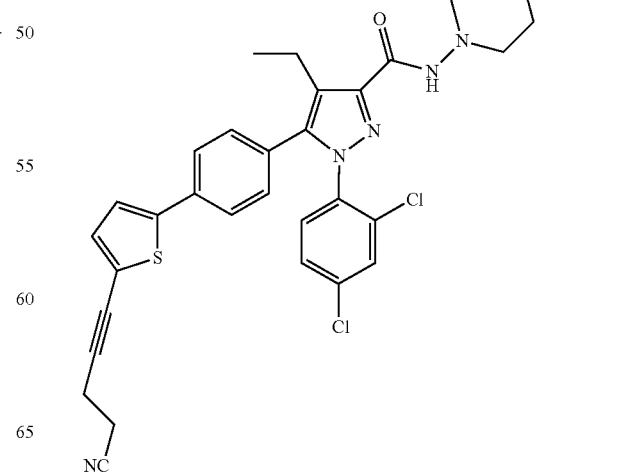

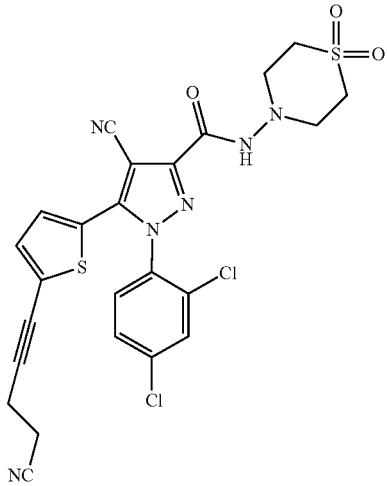

42

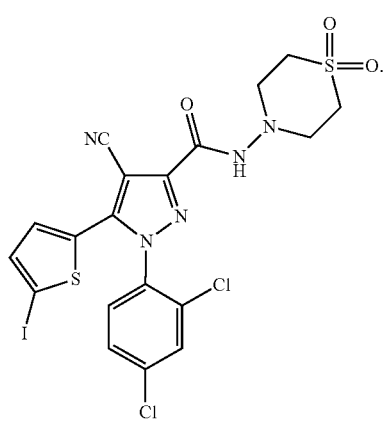

44

8. A compound of claim 1, and physiologically accepted salts thereof, consisting of the following structure:

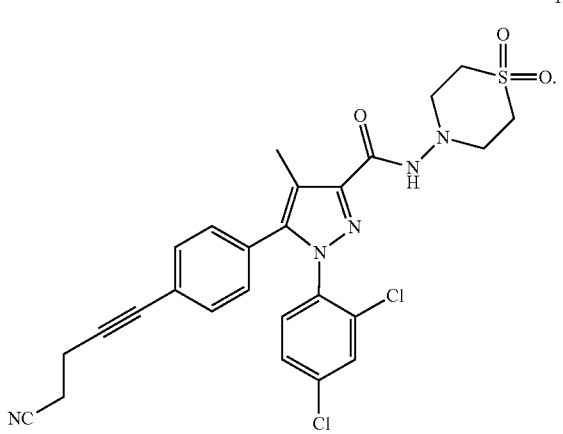

9. A compound of claim 1, wherein
R2 comprises —(CH$_2$)$_n$—Z;
n is an integer from 0 to about 7; and
Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom; or R2 comprises —(CH$_2$)$_n$—Z;
n is an integer from 0 to about 7; and
Z comprises

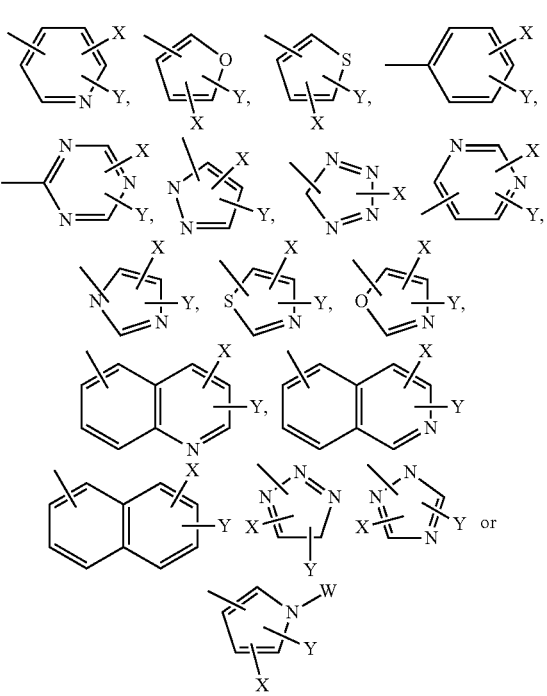

wherein X and Y each independently comprise, H, halogen, CF$_3$, CF$_2$H, N$_3$, NCS, ON, NO$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO2-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$ and X$_2$ each independently comprise H or alkyl, or
X$_1$ and X$_2$ together comprise part of a heterocyclic ring having about 4 to about 7 ring members and optionally one additional heteroatom selected from O, N or S, or
X$_1$ and X$_2$ together comprise part of an imide ring having about 5 to about 6 members, X$_3$ comprises H, alkyl, aryl, NO$_2$, (CH$_2$)$_m$CN, hydroxyloweralkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$ wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein $X_8$ comprises H, alkyl, carbocyclic ring, heterocyclic ring, aromatic ring, heteroaromatic ring, or —$CX_9$=$CHX_{10}$ wherein $X_9$ and $X_{10}$ each independently comprise H or alkyl Wherein m is an integer from 0 to 7 j is an integer from 0 to about 6, or k is an integer from 0 to about 2

W comprises H or alkyl; or

R2 comprises —$(CH_2)_n$—Z;

n is an integer from 0 to about 7; and

Z comprises a carbocyclic ring having 6 ring atoms fused to a heterocyclic ring having from 5 to 7 ring atoms, a carbocyclic ring having 6 ring atoms fused to a heteroaromatic ring having from 5 to 7 ring atoms, a heterocyclic ring having 6 ring atoms fused to a heterocyclic ring having from 5 to 7 ring atoms, an heterocyclic ring having 6 ring atoms fused to a heteroaromatic ring having from 5 to 7 ring atoms, an aromatic ring having 6 ring atoms fused to a heterocyclic ring having from 5 to 7 ring atoms, an aromatic ring having 6 ring atoms fused to a heteroaromatic ring having from 5 to 7 ring atoms, a heteroaromatic ring having 6 ring atoms fused to a heterocyclic ring having from 5 to 7 ring atoms or a heteroaromatic ring having 6 ring atoms fused to a heteroaromatic ring having from 5 to 7 ring atoms;

R1 comprises -T-Q-$(CH_2)_n$—Z;

n is an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Q comprises C≡C.

10. A compound of claim 1, wherein

R2 comprises —$(CH_2)_n$—Z;

n is 0; and

Z comprises an aromatic ring having about 5 to about 7 ring members, a heteroaromatic ring having about 5 to about 7 ring members; or R2 comprises —$(CH_2)_n$—Z;

n is an integer from 0 to about 7; and

Z comprises

[chemical structures]

wherein X and Y each independently comprise, H, halogen, $CF_3$, $CF_2H$, $N_3$, NCS, ON, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, alkyl-CN, O-aroyl, $O(CH_2)_jOX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, NHC(O)O-alkyl, NHSO2-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, aryl, $NO_2$, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$ wherein $X_7$ comprises H, alkyl, $NO_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein $X_8$ comprises H, alkyl, carbocyclic ring, heterocyclic ring, aromatic ring, heteroaromatic ring, or —$CX_9$=$CHX_{10}$ wherein $X_9$ and $X_{10}$ each independently comprise H or alkyl Wherein m is an integer from 0 to 7 j is an integer from 0 to about 6, or k is an integer from 0 to about 2

W comprises H or alkyl; or

R1 comprises -T-Q-$(CH_2)_n$—Z;

n is an integer from 0 to about 7;

T comprises an aromatic ring having 5 to about 8 carbon atoms as ring members, a heteroaromatic ring having 5 to about 8 ring members;

Q comprises C≡C.

11. A compound of claim 1, wherein

R2 comprises —$(CH_2)_n$—Z;

n is an integer from 0 to about 7; and

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom; or R2 comprises —(CH$_2$)$_n$—Z;

n is an integer from 0 to about 7; and

Z comprises

[chemical structures]

wherein X and Y each independently comprise, H, halogen, CF$_3$, CF$_2$H, N$_3$, NCS, ON, NO$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO2-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, aryl, NO$_2$, (CH$_2$)$_m$CN, hydroxy-loweralkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$ wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein X$_8$ comprises H, alkyl, carbocyclic ring, heterocyclic ring, aromatic ring, heteroaromatic ring, or —CX$_9$=CHX$_{10}$ wherein X$_9$ and X$_{10}$ each independently comprise H or alkyl Wherein m is an integer from 0 to 7 j is an integer from 0 to about 6, or k is an integer from 0 to about 2

W comprises H or alkyl; or

R2 comprises —(CH$_2$)$_n$—Z;

n is an integer from 0 to about 7; and

Z comprises a carbocyclic ring having 6 ring atoms fused to a heterocyclic ring having from 5 to 7 ring atoms, a carbocyclic ring having 6 ring atoms fused to a heteroaromatic ring having from 5 to 7 ring atoms, a heterocyclic ring having 6 ring atoms fused to a heterocyclic ring having from 5 to 7 ring atoms, an heterocyclic ring having 6 ring atoms fused to a heteroaromatic ring having from 5 to 7 ring atoms, an aromatic ring having 6 ring atoms fused to a heterocyclic ring having from 5 to 7 ring atoms, an aromatic ring having 6 ring atoms fused to a heteroaromatic ring having from 5 to 7 ring atoms, a heteroaromatic ring having 6 ring atoms fused to a heterocyclic ring having from 5 to 7 ring atoms or a heteroaromatic ring having 6 ring atoms fused to a heteroaromatic ring having from 5 to 7 ring atoms;

R1 comprises -T-Q-(CH$_2$)$_n$—Z, n is an integer from 0 to about 7;

T comprises an aromatic ring having 5 to about 8 carbon atoms as ring members or a heteroaromatic ring having 5 to about 8 ring members;

Q comprises C≡C; and

Z comprises CN, alkyl-CN, or ONO$_2$.

12. A compound of claim 1 wherein

R2 comprises —(CH$_2$)$_n$—Z;

n is an integer from 0 to about 7;

Z is OX$_3$; and

X$_3$ is NO2.

13. A compound of claim 1 wherein

R1 comprises -T-Q-(CH$_2$)$_n$—Z;

n is an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Z is OX$_3$; and

X$_3$ is NO2.

14. A compound of claim 1 wherein

R4 comprises —(CH$_2$)$_d$—Z, or —(CH$_2$)$_m$-Q$_1$-(CH$_2$)$_n$—Z.

15. A compound of claim 1, wherein

R1 comprises

-T-(CH$_2$)$_m$-Q$_1$-(CH$_2$)$_n$—Z;

—(CH$_2$)$_n$—Z;

—(CH$_2$)$_m$-Q$_1$-(CH$_2$)$_n$—Z;

-T-(CH$_2$)$_n$—Z; or

-T-Q-(CH$_2$)$_n$—Z; and

R2 comprises

—(CH$_2$)$_n$—Z;

—(CH$_2$)$_m$-Q$_1$-(CH$_2$)$_n$—Z;

-T-(CH$_2$)$_n$—Z; or

-T-(CH$_2$)$_m$-Q$_1$-(CH$_2$)$_n$—Z.

16. A compound of claim 1, wherein R3 is

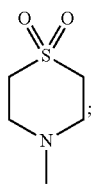

and
R2 is selected from

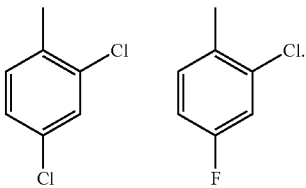

17. A compound of claim 1, and physiologically accepted salts thereof, comprising a structure selected from the group consisting of:
- 5-(4-[4-cyanobut-1-ynyl]phenyl)-1-(2,4-dichlorophenyl)-4-methyl-N-(1,1-dioxothiomorpholino)-1H-pyrazole-3-carboxamide
- 1-(2-chloro-4-fluorophenyl)-5-(4-(4-cyanobut-1-yn-1-yl)phenyl)-N-(1,1-dioxidothiomorpholino)-4-ethyl-1H-pyrazole-3-carboxamide;
- 5-(4-chlorophenyl)-1-(2,4-dichlorophenyl)-N-(1,1-dioxidothiomorpholino)-4-methyl-1H-pyrazole-3-carboxamide;
- 5-(4-bromophenyl)-1-(2,4-dichlorophenyl)-N-(1,1-dioxidothiomorpholino)-4-methyl-1H-pyrazole-3-carboxamide;
- 1-(2,4-dichlorophenyl)-N-(1,1-dioxidothiomorpholino)-5-(4-iodophenyl)-4-methyl-1H-pyrazole-3-carboxamide;
- 5-(4-chlorophenyl)-1-(2,4-dichlorophenyl)-N-(1,1-dioxidothiomorpholino)-4-ethyl-1H-pyrazole-3-carboxamide;
- 5-(4-bromophenyl)-1-(2,4-dichlorophenyl)-N-(1,1-dioxidothiomorpholino)-4-ethyl-1H-pyrazole-3-carboxamide;
- 1-(2,4-dichlorophenyl)-N-(1,1-dioxidothiomorpholino)-4-ethyl-5-(4-iodophenyl)-1H-pyrazole-3-carboxamide;
- 1-(2-chloro-4-fluorophenyl)-5-(4-chlorophenyl)-N-(1,1-dioxidothiomorpholino)-4-ethyl-1H-pyrazole-3-carboxamide;
- 5-(4-bromophenyl)-1-(2-chloro-4-fluorophenyl)-N-(1,1-dioxidothiomorpholino)-4-ethyl-1H-pyrazole-3-carboxamide;
- 1-(2-chloro-4-fluorophenyl)-N-(1,1-dioxidothiomorpholino)-4-ethyl-5-(4-iodophenyl)-1H-pyrazole-3-carboxamide; and
- 4-(4-(1-(2,4-dichlorophenyl)-3-((1,1-dioxidothiomorpholino)carbamoyl)-4-methyl-1H-pyrazol-5-yl)phenyl)but-3-yn-1-yl nitrate.

18. A compound of claim 1, wherein R3 comprises

wherein G comprises CH or N,
L, K and J each independently comprise $(CH_2)_n$, and at least one of L, K or J is $SO_2$,
n is an integer from 0 to about 7.

19. A compound of claim 1, wherein R3 is

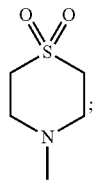

and
R4 is alkyl or CN.

20. A compound of claim 1, wherein R3 is

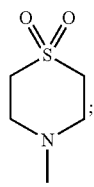

and
Q is C≡C.

* * * * *

UNITED STATES PATENT AND TRADEMARK OFFICE
CERTIFICATE OF CORRECTION

PATENT NO. : 8,853,205 B2  
APPLICATION NO. : 13/202499  
DATED : October 7, 2014  
INVENTOR(S) : Makriyannis et al.

Page 1 of 5

It is certified that error appears in the above-identified patent and that said Letters Patent is hereby corrected as shown below:

In the Claims

Column 62, line 46:
delete "ON" and insert --CN--

Column 63, line 51:
delete "ON" and insert --CN--

Column 64, line 21:
delete "ON" and insert --CN--

Column 66, line 17:
delete "ON" and insert --CN--

Column 67, line 51:
delete "ON" and insert --CN--

Column 69, line 41:
delete "ON" and insert --CN--

Column 70, line 43:
delete "ON" and insert --CN--

Column 72, line 38:
delete "ON" and insert --CN--

Signed and Sealed this
Twelfth Day of May, 2015

Michelle K. Lee
*Director of the United States Patent and Trademark Office*

Column 74, lines 5-10:
delete " 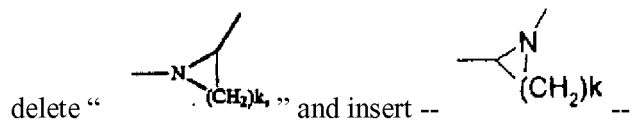 " and insert -- --
Column 74, line 38:
delete "ON" and insert --CN--
Column 76, line 60:
delete " 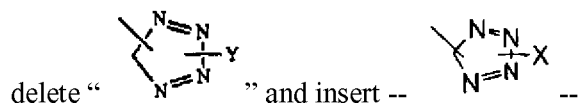 " and insert -- --
Column 76, line 65:
delete " 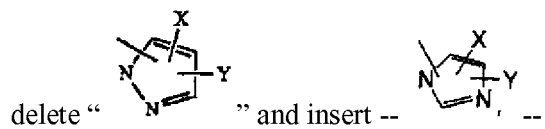 " and insert -- --
Column 78, line 64:
delete "ON" and insert --CN--
Column 80, lines 15-20:
delete " 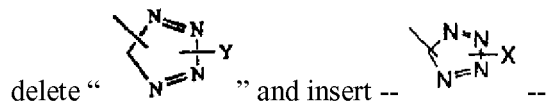 " and insert -- --
Column 80, lines 20-25:
delete " 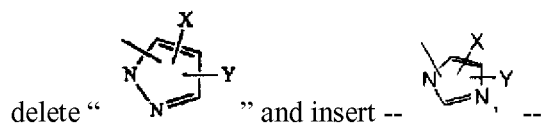 " and insert -- --
Column 81, line 47:
delete "ON" and insert --CN--
Column 82, line 17:
delete "ON" and insert --CN--
Column 83, line 60:
delete " 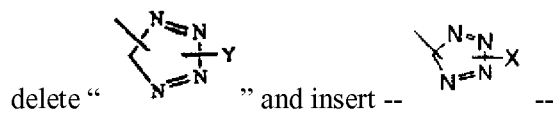 " and insert -- --

Column 83, line 65:
delete " 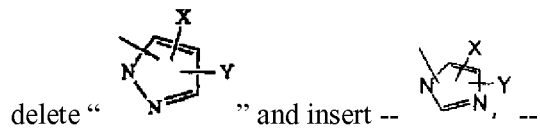 " and insert -- 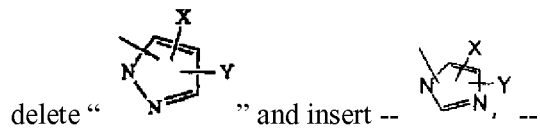 , --
Column 87, line 15:
delete " 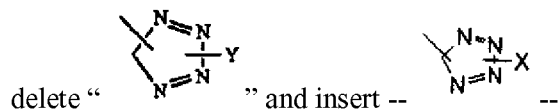 " and insert -- 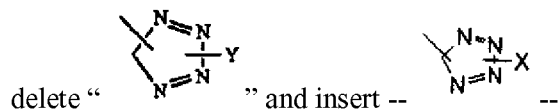 --
Column 87, line 20:
delete " 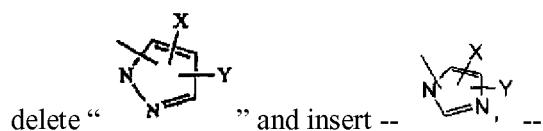 " and insert -- 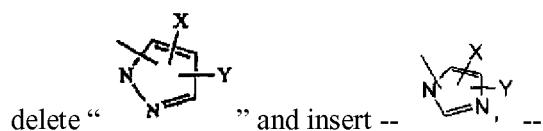 , --
Column 90, line 15:
delete " 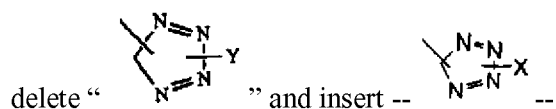 " and insert -- 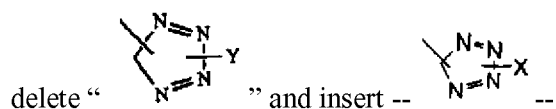 --
Column 90, line 20:
delete " 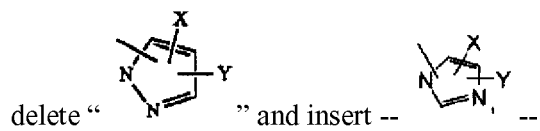 " and insert -- 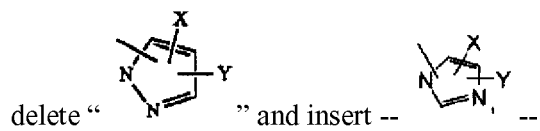 , --
Column 95, line 50:
delete " 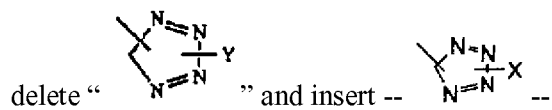 " and insert -- 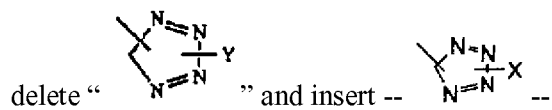 --
Column 95, line 55:
delete " 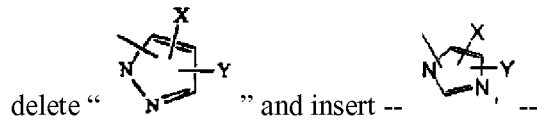 " and insert -- 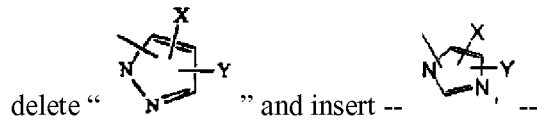 , --

Column 98, between lines 45-65:
delete " 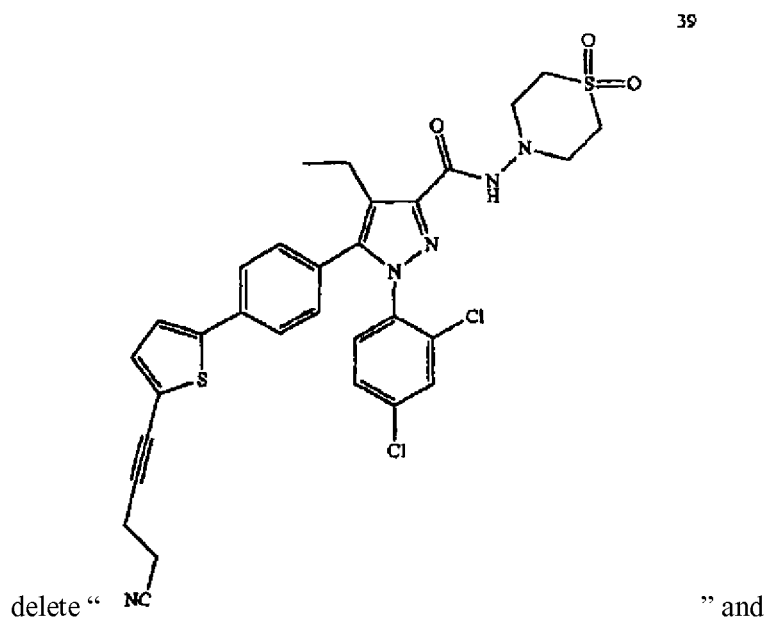 " and
insert -- 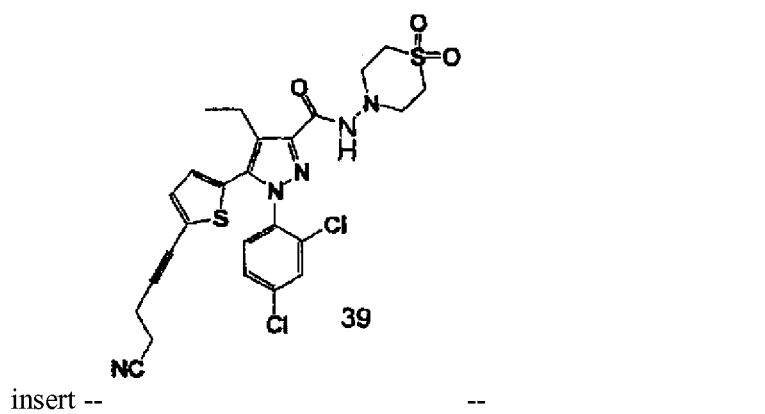 --
Column 99, lines 20-35:
delete " 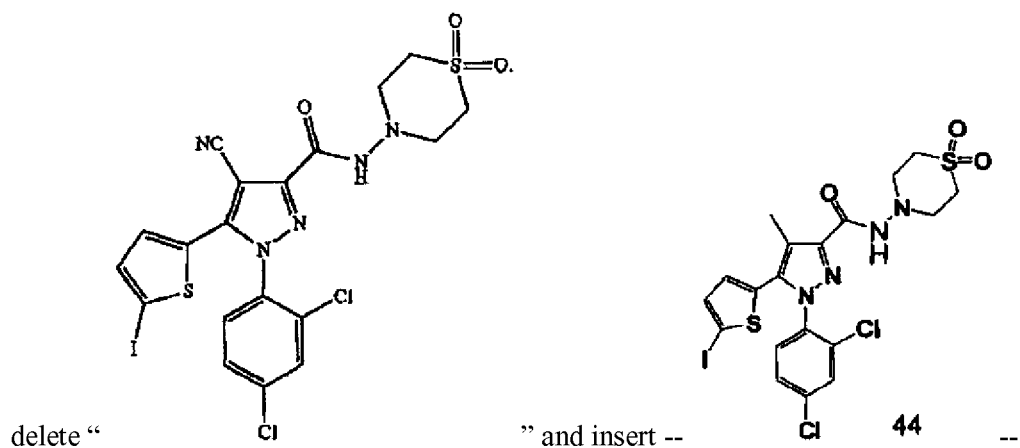 " and insert --
Column 100, line 44:
delete "ON" and insert --CN--

CERTIFICATE OF CORRECTION (continued)
U.S. Pat. No. 8,853,205 B2

Column 102, line 13:
delete "ON" and insert --CN--

Column 103, line 37:
delete "ON" and insert --CN--